United States Patent
De Roos et al.

(10) Patent No.: US 11,208,696 B2
(45) Date of Patent: Dec. 28, 2021

(54) PROGNOSTIC BIOMARKERS FOR TTK INHIBITOR CHEMOTHERAPY

(71) Applicant: NETHERLANDS TRANSLATIONAL RESEARCH CENTER B.V., Oss (NL)

(72) Inventors: Jeroen De Roos, Oss (NL); Joost Cornelis Marinus Uitdehaag, Oss (NL); Adrianus Petrus Antonius De Man, Hurwenen (NL); Rogier Christiaan Buijsman, Berghem (NL); Guido Jenny Rudolf Zaman, Berghem (NL)

(73) Assignee: NETHERLANDS TRANSLATIONAL RESEARCH CENTER B.V., Oss (NL)

( * ) Notice: Subject to any disclaimer, the term of this patent is extended or adjusted under 35 U.S.C. 154(b) by 409 days.

(21) Appl. No.: 15/566,583

(22) PCT Filed: Apr. 14, 2016

(86) PCT No.: PCT/EP2016/058292
§ 371 (c)(1),
(2) Date: Oct. 13, 2017

(87) PCT Pub. No.: WO2016/166255
PCT Pub. Date: Oct. 20, 2016

(65) Prior Publication Data
US 2019/0211401 A1 Jul. 11, 2019

(30) Foreign Application Priority Data
Apr. 17, 2015 (EP) ...................................... 15164133

(51) Int. Cl.
*C12Q 1/6886* (2018.01)
*C07D 213/74* (2006.01)
(Continued)

(52) U.S. Cl.
CPC ......... *C12Q 1/6886* (2013.01); *C07D 213/74* (2013.01); *C07D 239/48* (2013.01);
(Continued)

(58) Field of Classification Search
None
See application file for complete search history.

(56) References Cited

FOREIGN PATENT DOCUMENTS

| WO | 2009/024824 A1 | 2/2009 |
| WO | 2009/032694 A1 | 3/2009 |

(Continued)

OTHER PUBLICATIONS

Muche et al. ("Muche", Anticancer Research. 2014, 34, 4677-4684). (Year: 2014).*

(Continued)

*Primary Examiner* — Karl J Puttlitz
(74) *Attorney, Agent, or Firm* — Oliff PLC

(57) ABSTRACT

A method for identifying a tumor that is susceptible to treatment with a TTK inhibitor, including: a) providing a sample of a tumor; b) determining the presence of a mutated CTNNB1 gene in the sample, wherein the mutation is located in exon 3 of CTNNB1 and the presence of a mutated CTNNB1 gene indicates the tumor is susceptible to treatment with a TTK inhibitor. Alternatively, step b) is replaced by the step of determining the presence of a mutated CTNNB1 protein in the sample, wherein the mutation is located in exon 3 of CTNNB1 and the presence of a mutated CTNNB1 protein indicates the tumor is susceptible to treatment with a TTK inhibitor. In a further alternative, step b) includes determining an altered expression of a CTNNB1 regulated gene, whereby an altered expression of a CTNNB1 regulated gene indicates the tumor is susceptible to treatment with a TTK inhibitor.

21 Claims, 5 Drawing Sheets

Specification includes a Sequence Listing.

(51) Int. Cl.
C07D 239/48 (2006.01)
C07D 471/04 (2006.01)
C07D 471/14 (2006.01)
C07D 473/16 (2006.01)
C07D 487/04 (2006.01)

(52) U.S. Cl.
CPC ......... C07D 471/04 (2013.01); C07D 471/14 (2013.01); C07D 473/16 (2013.01); C07D 487/04 (2013.01); C12Q 2600/106 (2013.01)

(56) References Cited

FOREIGN PATENT DOCUMENTS

| WO | 2009/032703 | A1 | 3/2009 | |
|---|---|---|---|---|
| WO | 2009/156315 | A1 | 12/2009 | |
| WO | 2010/080712 | A2 | 7/2010 | |
| WO | 2010/108921 | A1 | 9/2010 | |
| WO | 2010/111406 | A2 | 9/2010 | |
| WO | 2010/124826 | A1 | 11/2010 | |
| WO | 2011/013729 | A1 | 2/2011 | |
| WO | 2011/016472 | A1 | 2/2011 | |
| WO | 2011/026579 | A1 | 3/2011 | |
| WO | 2011/063907 | A1 | 6/2011 | |
| WO | 2011/063908 | A1 | 6/2011 | |
| WO | 2011/064328 | A1 | 6/2011 | |
| WO | 2011/113862 | A1 | 9/2011 | |
| WO | 2011/123937 | A1 | 10/2011 | |
| WO | 2011/151259 | A1 | 12/2011 | |
| WO | 2011/157688 | A1 | 12/2011 | |
| WO | 2012/013557 | A1 | 2/2012 | |
| WO | 2012/032031 | A1 | 3/2012 | |
| WO | 2012/080228 | A1 | 6/2012 | |
| WO | 2012/080229 | A1 | 6/2012 | |
| WO | 2012/080230 | A1 | 6/2012 | |
| WO | 2012/080232 | A1 | 6/2012 | |
| WO | 2012/080234 | A1 | 6/2012 | |
| WO | 2012/080236 | A1 | 6/2012 | |
| WO | 2012/101029 | A1 | 8/2012 | |
| WO | 2012/101032 | A1 | 8/2012 | |
| WO | 2012/123745 | A1 | 9/2012 | |
| WO | 2012/130905 | A1 | 10/2012 | |
| WO | 2012/136531 | A1 | 10/2012 | |
| WO | 2012/139930 | A1 | 10/2012 | |
| WO | 2012/143329 | A1 | 10/2012 | |
| WO | 2012/168721 | A1 | 12/2012 | |
| WO | 2013/053051 | A1 | 4/2013 | |
| WO | 2013/135612 | A1 | 9/2013 | |
| WO | 2014/009219 | A1 | 1/2014 | |
| WO | 2014/037750 | A1 | 3/2014 | |
| WO | 2014/037751 | A1 | 3/2014 | |
| WO | 2014/056083 | A1 | 4/2014 | |
| WO | 2014/131739 | A2 | 9/2014 | |
| WO | 2014/195274 | A1 | 12/2014 | |
| WO | 2014/195276 | A1 | 12/2014 | |
| WO | 2014/198627 | A1 | 12/2014 | |
| WO | WO-2015155042 | A1 * | 10/2015 | ........... C07D 471/14 |

OTHER PUBLICATIONS

Primdahl et al ("Primdahl", Cancer Res. 1999, 59, 3346-3351) (Year: 1999).*
Higgins et al., "Targeted Therapies for Breast Cancer". The Journal of Clinical Investigation, vol. 121, No. 10, pp. 3797-3803, 2011.
Liu et al., "The MPS1 Family of Protein Kinases". The Annual Review of Biochemistry, pp. 561-585, 2012.
Baker et al., "The Mitotic Checkpoint in Cancer and Aging: What Have Mice Taught Us?". Current Opinion in Cell Biology, vol. 17, pp. 583-589, 2005.
Michel et al., "Complete Loss of the Tumor Suppressor MAD2 Causes Premature Cyclin B Degradation and Mitotic Failure in Human Somatic Cells". PNAS, vol. 101, No. 13, pp. 4459-4464, 2004.

Kops et al., "Lethality To Human Cancer Cells Through Massive Chromosome Loss By Inhibition of the Mitotic Checkpoint". PNAS, vol. 101, No. 23, pp. 8699-8704, 2004.
Daniel et al., "High Levels of The Mps1 Checkpoint Protein are Protective of Aneuploidy in Breast Cancer Cells". PNAS, vol. 108, No. 13, pp. 5384-5389, 2010.
Maire et al., "TTK/hMPS1 Is an Attractive Therapeutic Target for Triple-Negative Breast Cancer". PLoS One, vol. 8, No. 5, pp. 1-15, 2013.
Kilpinen et al., "Analysis of Kinase Gene Expression Patterns Across 5681 Human Tissue Samples Reveals Functional Genomic Taxonomy of the Kinome". PLoS One, vol. 5, No. 12, pp. 1-14, 2010.
Landi et al., "Gene Expression Signature of Cigarette Smoking and Its Role in Lung Adenocarcinoma Development and Survival". PLoS One, vol. 3, No. 2, pp. 1-8, 2008.
Liang et al., "Expression and Function Analysis of Mitotic Checkpoint Genes Identifies TTK as a Potential Therapeutic Target for Human Hepatocellular Carcinoma". PLoS, vol. 9, No. 6, pp. 1-13, 2014.
Mills et al., "Expression of TTK, A Novel Human Kinase, is Associated With Cell Proliferation". The Journal of Biological Chemistry, vol. 267, No. 22, pp. 16000-16006, 1992.
Mir et al., "In Silico Analysis of Kinase Expression Identifies WEE1 as a Gatekeeper Against Mitotic Catastrophe in Glioblastoma". Cancer Cells, vol. 18, pp. 244-257, 2010.
Salvatore et al., "A Cell Proliferation and Chromosomal Instability Signature in Anaplastic Thyroid Carcinoma". The Journal of Cancer Research, vol. 67, No. 21, pp. 10148-10158, 2007.
Slee et al., "Selective Inhibition of Pancreatic Ductal Adenocarcinoma Cell Growth By the Mitotic MPS1 Kinase Inhibitor NMS-P715". Molecular Cancer Therapeutics, vol. 13, No. 2, pp. 307-315, 2014.
Tannous et al., "Effects of the Selective MPS1 Inhibitor MPS1-IN-3 On Glioblastoma Sensitivity To Antimitotic Drugs". JNCI, vol. 105, No. 17, pp. 1322-1331, 2013.
Yuan et al., "Increased Expression of Mitotic Checkpoint Gene in Breast Cancer Cells With Chromosomal Instability". Clinical Cancer Research, vol. 12, No. 2, pp. 405-410, 2006.
Jemaà et al., "Characterization of Novel MPS1 Inhibitors With Preclinical Anticancer Activity". Cell Death and Differentiation, vol. 20, pp. 1532-1545, 2013.
Colombo et al., "Targeting the Mitotic Checkpoint for Cancer Therapy With NMS-P715, an Inhibitor of MPS1 Kinase". American Association for Cancer Research, vol. 70, No. 24, pp. 10255-10264, 2010.
Tardif et al., "Characterization of the Cellular and Antitumor Effects of MPI-0479605, a Small-Molecule Inhibitor of the Mitotic Kinase Mps1". Molecular Cancer Therapeutics, vol. 10, No. 12, 2011.
Naud et al., "Structure-Based Design of Orally Bioavailable 1H-Pyrrolo[3,2-c]Pyridine Inhibitors of Mitotic Kinase Monopolar Spindle 1 (MPS1)". Journal of Medicinal Chemistry, vol. 56, pp. 10045-10065, 2013.
Kusakabe et al., "Discovery Of Imidazo[1,2-b]Pyridazine Derivatives: Selective and Orally Available Mps1 (TTK) Kinase Inhibitors Exhibiting Remarkable Antiproliferative Activity". Journal of Medicinal Chemistry, vol. 58, pp. 1760-1775, 2015.
Liu et al., "The Discovery of Orally Bioavailable Tyrosine Threonine Kinase (TTK) Inhibitors: 3-(4-(Heterocyclyl)Phenyl)-1H-Indazole-5-Carboxamides as Anticancer Agents". Journal of Medicinal Chemistry, vol. 58, pp. 3366-3392, 2015.
Laufer et al., "Discovery of Inhibitors of the Mitotic Kinase TTK Based on N-(3-(3-Sulfamoylphenyl)-1H-Indazol-5-yl)-Acetamides and Carboxamides". Bioorganic and Medicinal Chemistry, vol. 22, pp. 4968-4997, 2014.
Logan et al., "The Wnt Signaling Pathway in Development and Disease". The Annual Review of Cell and Developmental Biology, pp. 781-810, 2004.
Morin et al., "Activation Of β-Catenin-Tcf Signaling in Colon Cancer By Mutations In β-Catenin or APC" Science, vol. 275, pp. 1787-1790, 1997.

(56) References Cited

OTHER PUBLICATIONS

Iwao et al., "Activation of The β-Catenin Gene By Interstitial Deletions Involving Exon 3 In Primary Colorectal Carcinomas Without Adenomatous Polyposis *coli* Mutations". Cancer Research, vol. 58, pp. 1021-1026, 1998.

Sparks et al., "Mutational Analysis of The APC/β-Catenin/Tcf Pathway in Colorectal Cancer". Cancer Research, vol. 58, pp. 1130-1134, 1998.

Miyoshi et al., "Activation of the β-Catenin Gene in Primary Hepatocellular Carcinomas By Somatic Alterations Involving Exon 3". Cancer Research, vol. 58, pp. 2524-2527, 1998.

Chen et al., "p53 Gene and Wnt Signaling in Benign Neoplasms: β-Catenin Mutations in Hepatic Adenoma but Not in Focal Nodular Hyperplasia". Hepatology, vol. 36, No. 4, pp. 927-935, 2002.

Rubinfeld et al., "Stabilization of β-Catenin By Genetic Defects in Melanoma Cell Lines". Science, vol. 275, pp. 1790-1792, 1997.

Zurawel et al., "Sporadic Medulloblastomas Contain Oncogenic β-Catenin Mutations". Cancer Research, vol. 58, pp. 896-899, 1998.

Shigemitsu et al., "Genetic Alteration of The β-Catenin Gene (CTNNB1) in Human Lung Cancer and Malignant Mesothelioma and Identification of a New 3p21.3 Homozygous Deletion". Oncogene, vol. 20, pp. 4249-4257, 2001.

Fukuchi et al., "β-Catenin Mutation in Carcinoma of the Uterine Endometrium". Cancer Research, vol. 58, pp. 3526-3528, 1998.

Liu et al., "Clinical Significance of CTNNB1 Mutation and Wnt Pathway Activation in Endometrioid Endometrial Carcinoma". JNCI, vol. 106, No. 9, pp. 1-8, 2014.

Palacios et al., "Mutations in the β-Catenin Gene (CTNNB1) in Endometrioid Ovarian Carcinomas", Cancer Research, vol. 58, pp. 1344-1347, 1998.

Voeller et al., "β-Catenin Mutatations in Human Prostate Cancer". Cancer Research, vol. 58, pp. 2520-2523, 1998.

Diaz et al., "The Molecular Evolution of Acquired Resistance to Targeted EGFR Blockade in Colorectal Cancers". Nature, vol. 486, pp. 537-540, 2012.

Yan et al., "Elevated Expression of axin2 and hnkd mRNA Provides Evidence That Wnt/β-Catenin Signaling is Activated in Human Colon Tumors". PNAS, vol. 98, No. 26, pp. 14973-14978, 2001.

He et al., "Identification of c-MYC as a Target of the APC Pathway". Science, vol. 281, pp. 1509-1512.

Barker et al., "Identification of Stem Cells in Small Intestine and Colon by Marker Gene Lgr5". Nature, vol. 449. pp. 1003-1007, 2007.

Chan et al., "Targeted Inactivation of CTNNB1 Reveals Unexpected Effects of β-Catenin Mutation". PNAS, vol. 99, No. 12, pp. 8265-8270, 2002.

Benjamini et al., "Controlling the False Discovery Rate: A Practical and Powerful Approach to Multiple Testing". Journal of the Royal Statistical Society. Series B (Methodological), vol. 57, No. 1, pp. 289-300, 1995.

Jul. 15, 2016 International Search Report issued in European Patent Application No. PCT/EP2016/058292.

Jul. 15, 2016 Written Opinion issued in European Patent Application No. PCT/EP2016/058292.

Aarts et al., "Tumour Selective Targeting of Cell Cycle Kinases for Cancer Treatment". Current Opinion in Pharmacology, vol. 13, pp. 529-535, 2013.

Kominami et al., "β-Catenin Mutation in Ovarian Solid Pseudopapillary Neoplasm". Pathology International, vol. 64, pp. 460-464, 2014.

Park et al., "Characterization of Gene Expression and Activated Signaling Pathways in Solid-Pseudopapillary Neoplasm of Pancreas". Modem Pathology, vol. 27, pp. 580-593, 2014.

Kobayashi et al., "Large Solid-Pseudopapillary Neoplasm of the Pancreas With Aberrant Protein Expression and Mutation Of β-Catenin: A Case Report and Literature Review of the Distribution of β-Catenin Mutation". The Japanese Society of Internal Medicine, vol. 52 pp. 2051-2056, 2013.

Jun. 3, 2020 Office Action issued in Japanese Patent Application No. 2017-554071.

Park, C.H. et al., "The inhibitory mechanism of curcumin and its derivative against β-catenin/Tcf signaling", FEBS Letters, 2005, vol. 579, pp. 2965-2971.

Apr. 15, 2021 Office Action issued in Japanese Patent Application No. 2017-554071.

Nollet, F. et al., "Genomic Organization of the Human β-Catenin Gene (CTNNB1)", Genomics, vol. 32, pp. 413-424, 1996.

Nov. 18, 2020 Office Action issued in European Patent Application No. 16 716 563.8.

Zaman, G. J.R. et al. "TTK Inhibitors as a Targeted Therapy for CTNNB1 (β-catenin) Mutant Cancers" Molecular Cancer Therapeutics, 2017, vol. 16, pp. 2609-2617.

* cited by examiner

Figure 1

```
          10          20          30          40          50
  MATQADLMEL  DMAMEPDRKA  AVSHWQQQSY  LDSGIHSGAT  TTAPSLSGKG
          60          70          80          90         100
  NPEEEDVDTS  QVLYEWEQGF  SQSFTQEQVA  DIDGQYAMTR  AQRVRAAMFP
         110         120         130         140         150
  ETLDEGMQIP  STQFDAAHPT  NVQRLAEPSQ  MLKHAVVNLI  NYQDDAELAT
         160         170         180         190         200
  RAIPELTKLL  NDEDQVVVNK  AAVMVHQLSK  KEASRHAIMR  SPQMVSAIVR
         210         220         230         240         250
  TMQNTNDVET  ARCTAGTLHN  LSHHREGLLA  IFKSGGIPAL  VKMLGSPVDS
         260         270         280         290         300
  VLFYAITTLH  NLLLHQEGAK  MAVRLAGGLQ  KMVALLNKTN  VKFLAITTDC
         310         320         330         340         350
  LQILAYGNQE  SKLIILASGG  PQALVNIMRT  YTYEKLLWTT  SRVLKVLSVC
         360         370         380         390         400
  SSNKPAIVEA  GGMQALGLHL  TDPSQRLVQN  CLWTLRNLSD  AATKQEGMEG
         410         420         430         440         450
  LLGTLVQLLG  SDDINVVTCA  AGILSNLTCN  NYKNKMMVCQ  VGGIEALVRT
         460         470         480         490         500
  VLRAGDREDI  TEPAICALRH  LTSRHQEAEM  AQNAVRLHYG  LPVVVKLLHP
         510         520         530         540         550
  PSHWPLIKAT  VGLIRNLALC  PANHAPLREQ  GAIPRLVQLL  VRAHQDTQRR
         560         570         580         590         600
  TSMGGTQQQF  VEGVRMEEIV  EGCTGALHIL  ARDVHNRIVI  RGLNTIPLFV
         610         620         630         640         650
  QLLYSPIENI  QRVAAGVLCE  LAQDKEAAEA  IEAEGATAPL  TELLHSRNEG
         660         670         680         690         700
  VATYAAAVLF  RMSEDKPQDY  KKRLSVELTS  SLFRTEPMAW  NETADLGLDI
         710         720         730         740         750
  GAQGEPLGYR  QDDPSYRSFH  SGGYGQDALG  MDPMMEHEMG  GHHPGADYPV
         760         770         780
  DGLPDLGHAQ  DLMDGLPPGD  SNQLAWFDTD  L
```

PROGNOSTIC BIOMARKERS FOR TTK INHIBITOR CHEMOTHERAPY

FIELD OF THE INVENTION

The present invention relates to methods to detect the mutant status of the CTNNB1 gene or CTNNB1 protein or the altered expression of a CTNNB1 regulated gene to identify tumors that are susceptible to anticancer therapy with a TTK inhibitor. The present invention also relates to methods to predict the outcome, or disease progression, of cancers that are treated with a TTK inhibitor, by detection of the mutant status of the CTNNB1 gene or CTNNB1 protein or the altered expression of a CTNNB1 regulated gene

BACKGROUND OF THE INVENTION

Targeted therapies bring great benefit to cancer patients because they can improve survival rates with fewer side effects than traditional, less selective cytotoxic drugs. Small molecule inhibitors of protein kinases are a prime example of the success of targeted therapy: many of these inhibitors exploit unique features of tumor cells, permitting cancer specificity while having limited effects on healthy cells. A classic example of a targeted therapy is the use of tyrosine kinase inhibitors and antibodies in breast cancer patients with amplification or overexpression of the HER2 gene (Higgins, M. J., and Baselga, J., J. Clin. Invest. 121: 3797; 2011).

To determine whether it is likely that a patient will respond to a certain targeted therapy, it is important to determine the status and presence of biomarkers that correlate with drug sensitivity in specimens of the patient's tumor, before the start of treatment.

The protein kinase TTK (EC 2.7.12.1), commonly referred to as Mps1, is a component of the spindle assembly checkpoint (SAC), a surveillance mechanism that ensures the fidelity of chromosome segregation (Liu, X., and Winey, M., Annu. Rev. Biochem. 81: 561; 2012). Defects in SAC functioning can lead to chromosome segregation errors by allowing mitotic exit in the presence of unattached kinetochores. Complete loss of SAC function is lethal in mice (Baker, D. J., et al., Curr. Opin. Cell Biol. 17, 583; 2005) and incompatible with the viability of human cell lines (Michel, L., et al. Proc. Natl. Acad. Sci. USA 101, 4459; 2004; Kops G. J., et al. Proc. Natl. Acad. Sci. USA 101, 8699; 2004). TTK mRNA levels are elevated in various human cancers, including breast, thyroid papillary carcinoma, hepatocellular carcinoma, pancreatic ductal adenocarcinoma, glioma, gastric, bronchogenic, and lung (Daniel, J., et al. Proc. Natl. Acad. Sci. USA 108: 5384; 2011; Maire, V., et al., PLoS ONE 8(5) e63712; 2013; Kilpinen, S., et al., PLoS ONE 5(12), e15068; 2010; Landi, M. T., et al., PLoS ONE 3(2) e1651; 2008; Liang, X. D., et al. PLoS ONE 9(6), e97739; 2014; Mills, G. B., et al. J. Biol. Chem. 267: 16000; 1992; Mir, S. E., et al., Cancer Cell 18: 244; 2010; Salvatore, G., et al., Cancer Res. 67: 10148; 2007: Slee, R. B., et al., Mol. Cancer Ther. 13: 307; 2014; Tannous, B. A., et al., J. Natl. Cancer Inst. 105: 1322; 2013; Yuan, B., et al., Clin. Cancer Res. 12: 405; 2006). Therefore, chemical compounds that inhibit the activity of TTK are useful in the treatment of a variety of cancers. These compounds may be applied as single agents, or in combination with other anti-cancer agents.

Different compounds have been disclosed which show an inhibitory effect on TTK. AstraZeneca UK Ltd. disclosed 2-anilinopurin-8-ones as inhibitors of TTK in WO2009/024824 A1. In WO2011/013729 A1, fused imidazoles, and in WO2011/016472 A1 pyridine and pyrimidine derivatives are disclosed as inhibitors of TTK by Oncotherapy Science Inc. Indazoles for inhibition of TTK have been disclosed by University Health Network in WO2011/123937 A1, WO2013/053051 A1 and WO2014/056083 A1. Dana Farber Cancer Institute disclosed pyrimido-diazepinones as inhibitors of TTK in WO2010/080712 A1. In WO2009/156315 A1, pyrazolo-quinazolines, in WO2012/101029 A1 tricyclic derivatives, in WO2010/108921 A1, N-aryl-2-(2-arylaminopyrimidin-4-yl)pyrrol-4-carboxamides, in WO2012/013557 A1, isoxazolo-quinazolines, in WO2012/101032 A1, tricyclic pyrrolo derivatives and in WO2012/139930 A1, pyrazolyl-pyrimidines are disclosed as inhibitors of TTK by Nerviano Medical Sciences S.R.L.

Myriad Pharmaceuticals Inc. disclosed purines as inhibitors of TTK in WO2010/111406 A2. Furthermore, Cancer Research Technology Ltd. disclosed pyrrolopyridineamino derivatives in WO2012/123745 A1 and bicycles in WO2014/037750 A1 and in WO2014/037751 A1 as inhibitors of TTK.

In WO2010/124826 A1, imidazoquinoxalines, in WO2011/026579 A1, aminoquinoxalines, in WO2011/063907 A1, WO2011/063908 A1, WO2011/064328 A1, WO2011/157688 A1, WO2012/143329 A1, WO2014/009219 A1, WO2014/195274 A1, WO2014/195276 A1 and WO2014/198647 A1, triazolopyridines, in WO2012/136531 A1, imidazopyridines, in WO2012/130905 A1, substituted benzimidazoles, in WO2012/032031 A1, WO2013/135612 A1 and WO2014/131739 A1, imidazopyridazines, in WO2011/113862 A1, WO2011/151259 A1, WO2012/080228 A1, WO2012/080229 A1, WO2012/080230 A1, WO2012/080232 A1, WO2012/080234 A1 and WO 2012/080236 A1, imidazopyrazines are respectively disclosed as inhibitors of TTK by Bayer Schering Pharma A.G.

Representative compounds of the different chemical classes have been investigated in cell proliferation assays with different human cancer cell lines. A representative TTK inhibitor of the imidazo-pyrazines, Mps-BAY2b, was shown to inhibit the proliferation of twenty-seven human cancer cell lines from different tumor origins with an $IC_{50}$ of 160 nM to 4.3 µM (Jemaa, M., et al., Cell Death Different. 20: 1532; 2013); no correlation was found between the response and the pattern of genomic instability, the activity of several proteins relevant for oncogenesis, or the functionality of the SAC.

NMS-P715, a representative of the pyrazolo-quinazoline class, inhibited the proliferation of a wide range of cell lines in a panel of 127 cancer cell lines (Colombo, R., et al., Cancer Res. 70: 10255; 2010); $IC_{50}$s were close to 1 µM or higher and there was no correlation observed between anti-proliferative effects and cellular doubling time.

MPI-04079605, a TTK inhibitor disclosed by Myriad, was shown to inhibit the growth of fourteen human cancer cell lines from different tumor origins, but only after prolonged incubation time (Tardif, K. D., et al., Mol. Cancer Res. 10: 2267; 2011).

CCT251455, a representative of the 1H-pyrrolo[2,3-c] pyridine class, inhibited the proliferation of HCT116 cells with a $GI_{50}$ of 160 nM (Naud, S., et al., J. Med. Chem. 56: 10045; 2013).

An imidazo[1,2-b]pyridazine-based TTK inhibitor disclosed by Shionogi, was shown to inhibit the proliferation of fourteen human cancer cell lines from different tumor origins with an $IC_{50}$ of 3.3 nM to 320 nM (Kusakabe, K., et al., J. Med. Chem. 58: 1716; 2015); CFI-401870, a representative of the indazoles, inhibited the proliferation of a wide range of cell lines in a panel of 22 cancer cell lines (Liu, Y., et al., J. Med. Chem. 58: ASAP; 2015) with $GI_{50}$s of 8 nM to 70 nM.

Whereas in the above cited profiling experiments, different cancer cell lines showed different relative sensitivities for TTK inhibitors, no genomic or other markers were identified that correlated with sensitivity to TTK inhibitors.

Several TTK inhibitors of the above mentioned chemical classes have been shown to reduce growth of xenografts in mouse models of melanoma (Colombo, R., et al.), colorectal carcinoma (Jemaa, M., et al.; Tardif, et al.; Laufer, R., et al., Bioorg. Med. Chem. 22: 4968; 2014), cervical carcinoma (Jemaa, M., et al.) and glioblastoma cells (Tannous, B. A. et al.), demonstrating the potential use of TTK inhibitors in treatment of various cancers.

In view of the broad activity of TTK inhibitors in many different cell lines and tumor types, there is a clear need for biomarkers that can be used to predict which cancers are most likely to respond to chemotherapeutic treatment with a TTK inhibitor. Such a prognostic drug sensitivity biomarker can be used to identify the most optimal patient population to the application of drug therapy with a TTK inhibitor, or can be used to predict the progression, or outcome of disease treated with a TTK inhibitor.

Statement of the Invention

In accordance with a first aspect of the present invention there is provided a method as defined in claim 1 appended hereto.

The present inventors have surprisingly observed that cancer cells that harbor mutations in the CTNNB1 gene (HUGO name: CTNNB1) are more sensitive to TTK inhibitors than normal cells or cancer cells that do not express mutant CTNNB1 (CTNNB1 proficient cells).

The CTNNB1 gene encodes a dual function protein, β-catenin, which regulates the coordination of cell adhesion and regulates gene transcription in the Wnt signaling pathway (Logan, C. Y., and Nusse, R., Annu. Rev. Cell. Dev. Biol. 896: 1998; 2004). Mutations in the CTNNB1 gene have been found in many cancers, including colorectal (Morin, P. J. et al., Science 275: 1787; 1997; Iwao, K., et al., Cancer Res. 58: 1021; 1998; Sparks, A. B., et al. Cancer Res. 58: 1130; 1998), and hepatocellular carcinoma (Miyoshi, Y., et al., Cancer Res. 58: 2524; 1998; Chen, Y. W., et al., Hepatology 36: 927; 2002), melanoma (Rubinfeld, B., et al., Science 275: 1790; 1997), medulloblastoma (Zurrawel, R. H., et al. Cancer Res. 58: 896; 1998), lung (Shigemitsu, K., et al., Oncogene 20: 4249; 2001), endometrial (Fukuchi, T., et al., Cancer Res. 58: 3526; 1998; Liu, Y., et al., J. Natl. Canc. Inst. 106(9); 2014), ovarium (Palacios, J., and Gamallo, C., Cancer Res. 58: 1344; 1998) and prostate cancer (Voeller, H. J., and Gelmann, E. P., Cancer Res. 58, 2520; 1998).

The activity of β-catenin is regulated by phosphorylation at serine and threonine residues by the protein kinases glycogen synthase kinase 33 (JGSK31) and casein kinase I (CKI), followed by ubiquitination and degradation by the proteasome (Liu, C., et al. Cell 108, 837; 2002). Mutations in the CTNNB1 gene resulting in deletion or substitution of one or more of these serine or threonine residues impairs phosphorylation and degradation, resulting in an overactive β-catenin, and uncontrolled cell growth (Morin, P. J. et al., Science 275: 1787; 1997; Liu, C., et al.).

The present invention provides methods to determine the mutant status of CTNNB1 in tumor derived materials, to determine the susceptibility of said tumors to anticancer therapy with a TTK inhibitor. The present invention also provides methods to determine the mutant status of CTNNB1 to monitor the effectiveness of therapy of proliferative disease with a TTK inhibitor, or to predict the outcome of cancers that are treated with a TTK inhibitor.

The analysis of the mutant status of CTNNB1 may be performed in combination with analyses of the mutant status or expression of other genes and/or proteins, or may be confined to an analysis of only CTNNB1 gene status.

The present invention constitutes a diagnostic method. However, the method is not performed directly on the human or animal body. The diagnostic method may be performed in a laboratory, but provides results that allow a physician to make an accurate prognosis of disease progression in a cancer patient, particularly with respect to whether a patient is likely to respond to chemotherapy with a TTK inhibitor, applied either as a single agent, or in combination with other therapeutic agents or radiotherapy.

More specifically, the present invention provides methods to determine the status of oncogenic CTNNB1 mutations in tumor derived materials to determine the susceptibility of said tumors in anti-cancer therapy with a TTK inhibitor as defined in Formulas I-VIII detailed herein.

Many different mutations in β-catenin have been observed in cancer patients, and these have been categorized in databases such as COSMIC (http://cancer.sanger.ac.uk/cancergenome/projects/cosmic/). The expression of CTNNB1 mutations in human cancers is reported in The Cancer Genome Atlas, which can be accessed at http://www.cancerenome.nih.gov.

A link to the CTNNB1 nucleic acid and protein sequence can be found at http://www.genenames.org/cgi-bin/ene_symbol_report?hgnc_id=2514 the disclosure of which is herein incorporated by reference. The protein sequence and amino acid numbering of CTNNB1 is also given in FIG. 1 appended hereto.

Exon 3 of CTNNB1 contains a hot spot of mutations that affect the ability of kinases to phosphorylate β-catenin (Morin, P. J. et al., 1997). The lack of this phosphorylation results in β-catenin accumulation in the nucleus (Liu, C. et al., 2002). More specifically, mutation or deletion of the serine residues at positions 33, 37 or 45, or mutation or deletion of the threonine residue at position 41 alter the GSK3β phosphorylation motifs which participate in the degradation of β-catenin (Rubinfeld, B., et al.; Morin, P. J., et al.). Consequently, these mutations result in increased oncogenic signaling (Rubinfeld, B., et al.; Morin, P. J., et al.).

In accordance with a further aspect of the invention there is provided a method according to claims 15 to 18 appended hereto. Specifically, a method is described to determine whether a chemical compound is a TTK inhibitor, said method comprising the steps of: a) Providing first and second mammalian cell lines, wherein the first cell line is CTNNB1-mutated and the second cell line is CTNNB1 proficient; b) Contacting said first and second cell lines with a first candidate compound; and, c) Determining by assay the inhibition of cell proliferation of said first and second cell lines. In an important variant of this method, steps b) and c) as mentioned above are repeated with a second candidate compound and a selection of candidate compound is made based on the activity of the respective candidate compounds in the assay with said first cell line.

In an embodiment, the first and second cell lines used in this method may be cancer cell lines. In an alternative embodiment, the first and second cell lines may be isogenic cell lines.

The present inventors have surprisingly observed that expression of three of the mutations described above correlates with increased susceptibility of cancer cells to chemical inhibitors of TTK. Therefore, detection of the mutant status of the CTNNB1 gene at serine 33, threonine 41, or serine 45 can be used to determine the susceptibility of tumors for treatment with TTK inhibitors.

BRIEF DESCRIPTION OF THE FIGURES

The invention will be described with reference to the appended figures in which:

FIG. 1 is the protein sequence and amino acid numbering of CTNNB1 (β-catenin) (UniProt code P35222) (SEQ ID NO: 1). Mutation or deletion of the underlined serine (S) or threonine (T) residues at positions 33, 37, 41 and 45 alter the phosphorylation and degradation of β-catenin (Rubinfeld, B., et al.; Morin, P. J., et al.).

Figure 2A:
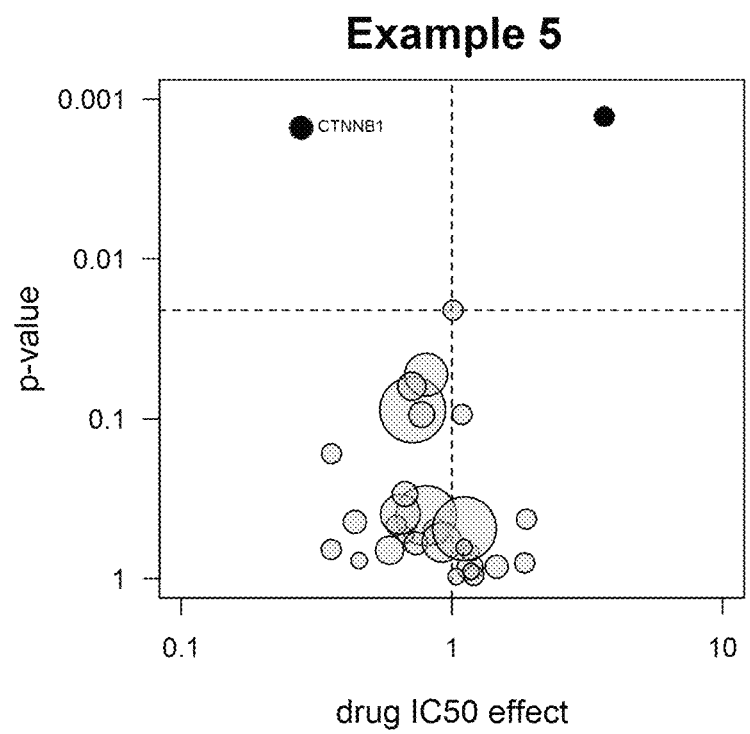
FIGS. 2A-2G represent the volcano plots of cellular profiling in 66 cancer cell lines for Examples 5, 8, 9, 12, 13, 17 and 20.

For completeness, a volcano plot is a graphical representation of an analysis of variance (Anova) of the association of cancer gene mutations present in cell lines and the response of these cell lines in proliferation assays with compounds. The volcano plot shows the average $IC_{50}$ shift between mutant and non-mutant cell lines (x-axis) and the significance from the Anova test (y-axis). Significance was corrected for multiple-testing and all associations above the threshold level (dotted line) are filled in black. Areas of circles are proportional with the number of cell lines carrying mutations. The cancer cell lines used in the drug sensitivity analysis are listed in Table 1 herein below.

DETAILED DESCRIPTION OF THE INVENTION

Methods of obtaining a sample of a tumor for analysis are well known in the art and require no specific elucidation here. The mutant status of the CTNNB1 gene of a tumor from an individual with cancer can be determined by analyzing the DNA sequence of a sample of the tumor, and comparing the tumor DNA sequence with that in healthy tissue, or with the 'wild-type' CTNNB1 sequence, referred to in the UniProt data base as P35222, and displayed in FIG. 1. A DNA sample may be taken directly from a tumor biopsy, or may be derived from circulating tumor DNA (Diaz, L. A., et al., Nature 486: 537; 2012). The mutant status of the CTNNB1 gene may also be determined by sequencing of the mRNA of the tumor sample, or may be determined indirectly by analysis of the amino acid sequence of β-catenin, or by determination of the phosphorylation status of β-catenin using specific antibodies.

As the mutations affect the degradation of β-catenin, they affect the total cellular levels of β-catenin and the amount β-catenin in the nucleus. Therefore, the mutant status of the CTNNB1 gene may also be determined indirectly by determining total or nuclear β-catenin levels in tumor cells.

Alternatively, the mutant status of CTNNB1 may be determined by analyzing the expression of genes that are regulated by β-catenin. The detection of β-catenin-regulated genes may be determined by extracting RNA from a sample of a tumor and measuring gene expression using reverse-transcriptase polymerase chain reaction (RT-PCR) or using microarray analysis. Many genes regulated by β-catenin have been described, and include Axin2 (Yan, D. et al., Proc. Natl. Acad. Sci. USA 98: 14973; 2001), c-myc (He, T. C. et al., Science 281: 1509; 1998) and LGR5 (Barker, N. et al., Nature 499: 1003; 2007). A comprehensive list of β-catenin-regulated genes can be found at the Wnt home page (http://web.stanford.edu/group/nusselab/cgi-bin/wnt/targetgenes) and in scientific articles (Willert, J. et al., BMC Dev. Biol. 2:8; van de Wetering, M et al., Cell 111: 241; 2002).

The expression of β-catenin-regulated genes may also be determined at the protein level, using specific antibodies or mass-spectroscopy-based methods. Since several β-catenin-regulated genes are oncogenes, the mutant status of CTNNB1 can also be determined by measuring oncogenic signaling.

Examples of inhibitors of TTK are chemical compounds belonging to the class of (5,6-dihydro)pyrimido[4,5-e]indolizines according to Formula I or pharmaceutically acceptable salts thereof.

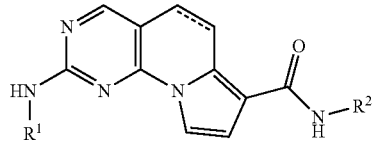

Formula I wherein,
$R^1$ is selected from the group consisting of:

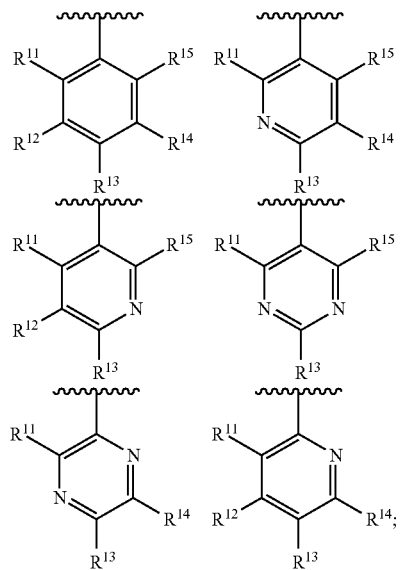

$R^{11}$ is H, halogen, (1-2C)alkyl, (2-3C)alkenyl, (2-3C)alkynyl, (1-2C)alkoxy or $OC_2H_3$, all alkyl and alkoxy groups optionally being substituted with one or more halogen;
$R^{12}$ is H, halogen, (1-2C)alkyl or (1-2C)alkoxy;
$R^{13}$ is $R^{131}CH_2$, $R^{132}O$, $R^{133}R^{134}N$, $R^{135}C(O)$, $R^{136}S$, $R^{136}S(O)$, $R^{136}S(O)(NH)$, $R^{137}SO_2$, (2-7C)heterocycloalkyl, or (1-5C)heteroaryl each heterocycloalkyl or heteroaryl optionally being substituted with (1-2C)alkyl, fluoro, hydroxyl, oxo, (1-2C)alkoxy, (1-6C)alkylcarbonyl, (1-6C)alkylsulfonyl, (1-5C)alkoxycarbonyl, (1-6C)alkylaminocarbonyl, (3-6C)cycloalkylcarbonyl, (2-7C)heterocycloalkylcarbonyl or di[(1-2C)alkyl]amino, each alkylcarbonyl, alkylsulfonyl, alkoxycarbonyl, alkylaminocarbonyl, cycloalkylcarbonyl or heterocycloalkylcarbonyl optionally being substituted with (1-2C) alkyl, fluoro, hydroxyl, cyano, oxo or (1-2C)alkoxy;

$R^{131}$ is (1-6C)alkylcarbonylamino, (3-6C)cycloalkylcarbonylamino or (2-7C)heterocycloalkylcarbonylamino each optionally substituted with one or more groups selected from (1-2C)alkyl, fluoro, hydroxyl or (1-2C)alkoxy;

$R^{132}$ is (1-6C)alkyl, (3-6C)cycloalkyl, (2-7C)heterocycloalkyl, (6-10C)aryl or (1-5C)heteroraryl each optionally substituted with one or more groups selected from (1-2C) alkyl, halogen, hydroxyl, (1-2C)alkoxy, di[(1-2C)alkyl] amino or (2-7C)heterocycloalkyl;

$R^{133}$ is (1-6C)alkyl, (3-6C)cycloalkyl, (2-7C)heterocycloalkyl (1-6C)alkylcarbonyl, (1-5C)alkoxycarbonyl, (3-6C) cycloalkylcarbonyl or (2-7C)heterocycloalkylcarbonyl, each optionally substituted with one or more groups selected from (1-2C)alkyl, halogen, hydroxyl or (1-2C) alkoxy, di[(1-2C)alkyl]amino or (2-7C)heterocycloalkyl;

$R^{134}$ is hydrogen or (1-2C)alkyl;

$R^{135}$ is (2-7C)heterocycloalkyl, (1-6C)alkylamino, di[(1-6C)alkyl]amino, (2-7C)heterocycloalkylamino or (3-6C) cycloalkylamino each optionally substituted with one or more groups selected from (1-2C)alkyl, fluoro, hydroxyl, (1-2C)alkoxy, di[(1-2C)alkyl]amino, (2-7C)heterocycloalkyl, oxo, cyano or amino;

$R^{136}$ is (1-6C)alkyl, (3-6C)cycloalkyl, (2-7C)heterocycloalkyl each optionally substituted with one or more groups selected from (1-2C)alkyl, fluoro, hydroxyl or (1-2C) alkoxy;

$R^{137}$ is (1-6C)alkyl, (3-6C)cycloalkyl, (2-7C)heterocycloalkyl, (1-6C)alkylamino, di[(1-6C)alkyl]amino, (2-7C)heterocycloalkylamino or (3-6C)cycloalkylamino, each optionally substituted with one or more groups selected from (1-2C)alkyl, fluoro, hydroxyl or (1-2C)alkoxy;

$R^{14}$ is H, halogen, (1-2C)alkyl or (1-2C)alkoxy; and $R^{is}$ is H, halogen.

In the above Formula I, $R^2$ is selected from the group consisting of:

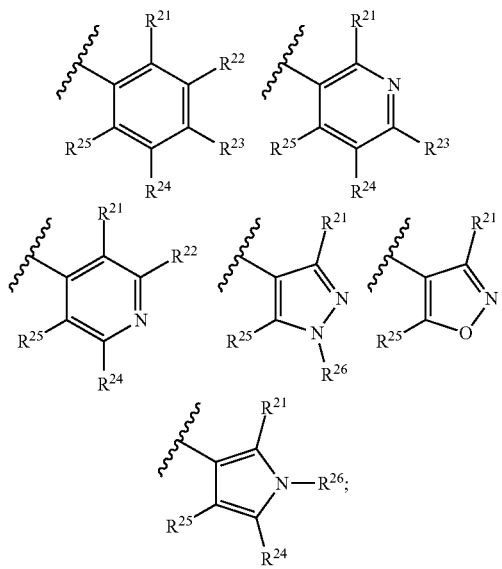

$R^{21}$ is H, halogen, (1-3C)alkyl, (1-2C)alkoxy, hydroxy(1-2C)alkyl, (3-4C)cycloalkyl, (2-3C)alkenyl or cyano;

$R^{22}$ is H, halogen, (1-2C)alkyl or (1-2C)alkoxy;

$R^{23}$ is H, halogen, (1-2C)alkyl, (1-2C)alkoxy, cyano or hydroxy;

$R^{24}$ is H, halogen, (1-2C)alkyl or (1-2C)alkoxy;

$R^{25}$ is H, halogen, (1-3C)alkyl, (1-2C)alkoxy, hydroxy(1-2C)alkyl, (3-4C)cycloalkyl, (2-3C)alkenyl or cyano;

$R^{26}$ is H, (1-6C)alkyl, (3-6C)cycloalkyl, (2-5C)heterocycloalkyl, (1-2C)alkoxy[(2-4C)alkoxy]$_n$(1-6C)alkyl, wherein n represents an integer of 1, 2, 3 or 4, all alkyl, heterocycloalkyl and (1-2C)alkoxy[(2-4C)alkoxy]$_n$(1-6C) alkyl groups optionally substituted with one or more groups selected from (1-2C)alkyl, (1-2C)alkoxy, hydroxyl, oxo, amino, (3-6C)cycloalkyl, di[(1-2C)alkyl] amino or (2-5C)heterocycloalkyl.

In the above Formula I only one of $R^{21}$ and $R^{25}$ in $R^2$ can be H.

Other examples of known TTK inhibitors are chemical compounds belonging to the class of pyrazolo-quinazolines according to Formula II or pharmaceutically acceptable salts thereof as described in WO2009/156315 A1.

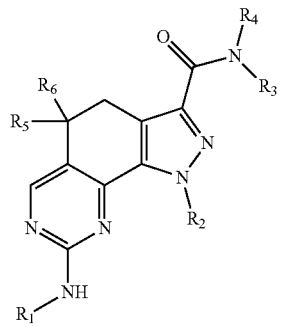

Formula II wherein,
$R^1$ and $R^3$ are independently selected from the group consisting of (6-10C)aryl and (1-5C)heteroaryl, wherein both groups optionally can be substituted;
$R^2$ is selected from the group consisting of (1-6C)alkyl and (2-6C)alkenyl, wherein both groups optionally can be substituted;
$R^4$ is selected from the group consisting of hydrogen and (1-6C)alkyl, wherein both groups optionally can be substituted;
$R^5$ and $R^6$ are independently hydrogen or methyl.

Other, known TTK inhibitors are chemical compounds belonging to the class of imidazo-pyrazines according to Formula III or pharmaceutically acceptable salts thereof as described in WO2011/013729 A1, WO2011/113862 A1, WO2011/151259 A1, WO2012/080228 A1, WO2012/080229 A1, WO2012/080230 A1, WO2012/080232 A1, WO2012/080234 A1 and WO 2012/080236 A1.

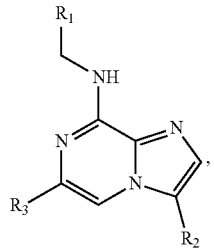

Formula III wherein,
$R^1$ is selected from the group consisting of (1-6C)alkyl, halo(1-6C)alkyl, HO-(1-6C)alkyl, $H_2N$-(1-6C)alkyl, cyano(1-6C)alkyl, (1-6C)alkoxy(1-6C)alkyl, (2-6C)alkenyl, (2-6C)alkynyl, (3-6C)cycloalkyl, (3-7C)heterocycloalkyl, (6-10C)aryl and (1-5C)heteroaryl, wherein said groups optionally can be substituted;

R² is selected from the group consisting of (6-10C)aryl and (1-9C)heteroaryl, wherein both groups optionally can be substituted;

R³ is selected from the group consisting of: (1-6C)alkyl, —(CH₂)ₙ-(3-7C) heterocycloalkyl), —(CH₂)ₙ-(4-8C) heterocycloalkenyl), (3-7C)heterocycloalkyl, (6-10C) aryl, (1-9C)heteroaryl, —(CH₂)ₙ-(6-10C)aryl, —O-(6-10C)aryl, —C(=O)N and cyano, wherein said groups can be substituted and further wherein n is an integer of 0, 1 or 2.

Another example of known TTK inhibitors are chemical compounds belonging to the class of purines according to Formula IV or pharmaceutically acceptable salts thereof as described in WO2010/111406 A1.

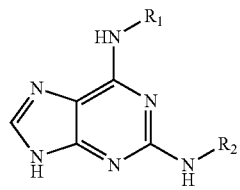

Formula IV wherein,
R¹ is selected from the group consisting of (3-6C)cycloalkyl and (3-7C)heterocycloalkyl, wherein said groups optionally can be substituted; and,
R² is selected from the group consisting of:
a) (6-10C)aryl, and,
b) (1-5C)heteroaryl,
wherein both groups optionally can be substituted.

Yet, other known TTK inhibitors are chemical compounds belonging to the class of imidazopyridazines according to Formula V or pharmaceutically acceptable salts thereof as described in WO2011/013729 A1, WO2012/032031 A1, WO2013/135612 A1 and WO2014/131739 A1.

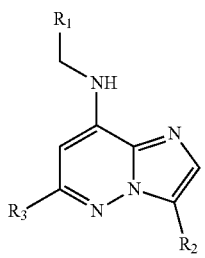

Formula V wherein,
R¹ is selected from the group consisting of hydrogen, (1-6C)alkyl, halo(1-6C)alkyl, HO(1-6C)alkyl, (3-6C) cycloalkyl, (3-7C)heterocycloalkyl and (1-5C)heteroaryl, wherein said groups optionally can be substituted;
R² is (6-10C)aryl or (1-9C)heteroaryl, each of which may be optionally substituted;
R³ is selected from the group consisting of X-(6-10C)aryl or X-(1-9C)heteroaryl, wherein both groups optionally can be substituted, wherein X represents S(=O)ₚ, O, NR⁴, CR⁴ᵃR⁴ᵇ, C=CR⁴ᵃR⁴ᵇ and further wherein p is an integer of 0, 1, 2;
R⁴, R⁴ᵃ, R⁴ᵇ represent independently from each other a hydrogen atom or (1-6C)alkyl.

Other, known TTK inhibitors are chemical compounds belonging to the class of triazolopyridines according to Formula VI or pharmaceutically acceptable salts thereof as described in WO2011/063907 A1, WO2011/063908 A1, WO2011/064328 A1, WO2011/157688 A1, WO2012/143329 A1, WO2014/009219 A1, WO2014/195274 A1, WO2014/195276 and WO2014/198647 A1.

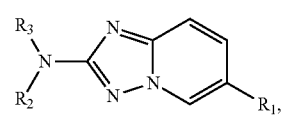

Formula VI wherein,
R¹ represents a phenyl group, a pyridyl group or an indolyl group wherein said groups can optionally be substituted;
R² represents a phenyl group, a pyridyl group or a pyrimidyl group wherein said groups can optionally substituted;
R³ represents a group selected from: hydrogen or —C(=O)—O—(CR⁷R⁸)—O—C(=O)—R⁴ wherein R⁴ represents a group selected from: (1-6C)alkyl, substituted one or more times, identically or differentially, with a group selected from: —NH₂, —N(H)R⁵, —N(R⁵)R⁶, (4-7C)heterocycloalkyl, optionally substituted, one or more times, identically or differentially, with a group selected from —NH₂, —N(H)R⁵, —N(R⁵)R⁶.
R⁵ and R⁶, independently from each other, represent a group selected from a hydrogen atom and (1-3C)alkyl.
R⁷ represents a group selected from a hydrogen atom and (1-3C)alkyl.
R⁸ represents a hydrogen atom Another example of known TTK inhibitors are chemical compounds belonging to the class of pyrrolopyridines according to Formula VII or pharmaceutically acceptable salts thereof as described in WO2009/032694 A1, WO2009/032703 A1 and Nature Chemical Biology 6 (2010), 359.

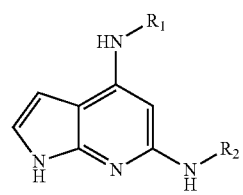

Formula VII wherein,
R¹ is selected from the group consisting of (6-10C)aryl, wherein said group optionally can be substituted;
R² is selected from the group consisting of (6-10C)aryl, wherein said group optionally can be substituted.

Yet, another example of known TTK inhibitors are chemical compounds belonging to the class of aminoyridines and aminopyrimidines according to Formula VIII or pharmaceutically acceptable salts thereof as described in WO2011/

016472 A1, ACS Med. Chem. Letters 3 (2012), 560 and Bioorg. Med. Chem. Letters 23 (2015), 2247.

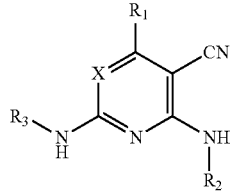

Formula VIII wherein,
$R^1$ is selected from the group consisting of hydrogen atom or amino;
$R^2$ is selected from the group consisting of (6-10C)aryl, (1-5C)heteroaryl, (1-6C)alkyl, (3-6C)cycloalkyl and (3-7C)heterocycloalkyl, wherein said groups optionally can be substituted;
$R^3$ is selected from the group consisting of (6-10C)aryl, wherein said groups optionally can be substituted;
X is C or N.

The terms as used herein refer to the following:
Halogen means fluorine, chlorine, bromine or iodine.
(1-2C)Alkyl means an alkyl group having 1 to 2 carbon atoms, being methyl or ethyl. A methyl group may be indicated as Me or $CH_3$.
(1-3C)Alkyl means a branched or unbranched alkyl group having 1-3 carbon atoms, being methyl, ethyl, propyl or isopropyl.
(1-4C)Alkyl means a branched or unbranched alkyl group having 1-4 carbon atoms, being methyl, ethyl, propyl, isopropyl, butyl, isobutyl, sec-butyl or tert-butyl, (1-3C) alkyl groups being preferred.
(1-5C)Alkyl means a branched or unbranched alkyl group having 1-5 carbon atoms, for example methyl, ethyl, propyl, isopropyl, butyl, isobutyl, sec-butyl, tert-butyl, pentyl and isopentyl, (1-4C)alkyl groups being preferred.
(1-6C)Alkyl means a branched or unbranched alkyl group having 1-6 carbon atoms, for example methyl, ethyl, propyl, isopropyl, butyl, tert-butyl, n-pentyl and n-hexyl. (1-5C)alkyl groups are preferred, (1-4C)alkyl being more preferred.
(1-2C)Alkoxy means an alkoxy group having 1-2 carbon atoms, the alkyl moiety having the same meaning as previously defined.
(2-4C)Alkoxy means an alkoxy group having 2-4 carbon atoms, for example ethoxy, propyloxy, butyloxy, isopropyloxy, isobutyloxy, and tertbutyloxy. Ethyloxy and propyloxy being preferred. Ethyloxy groups being more preferred.
(1-3C)Alkoxy means an alkoxy group having 1-3 carbon atoms, the alkyl moiety having the same meaning as previously defined. (1-2C)Alkoxy groups are preferred.
(1-4C)Alkoxy means an alkoxy group having 1-4 carbon atoms, the alkyl moiety having the same meaning as previously defined. (1-3C)alkoxy groups are preferred, (1-2C)alkoxy groups being most preferred.
(1-5C)Alkoxy means an alkoxy group having 1-5 carbon atoms, the alkyl moiety having the same meaning as previously defined. (1-4C)Alkoxy groups are preferred, (1-3C)alkoxy groups being more preferred.
(2-3C)Alkenyl means a branched or unbranched alkenyl group having 2-3 carbon atoms, such as ethenyl or 2-propenyl.
(2-3C)Alkynyl means ethynyl or 2-propynyl.

(3-4C)Cycloalkyl means a cycloalkyl group having 3-4 carbon atoms, being cyclopropyl or cyclobutyl.
(3-6C)cycloalkyl means a cycloalkyl group having 3-6 atoms. Examples of "cycloalkyl" include, but are not limited to, cyclopropyl, cyclobutyl, cyclopentyl or cyclohexyl.
(2-5C)Heterocycloalkyl means a heterocycloalkyl group having 2-5 carbon atoms, preferably 3-5 carbon atoms; and one or two heteroatoms selected from N, O and/or S, which may be attached via a heteroatom if feasible, or a carbon atom. Preferred heteroatoms are N or O. Preferred are oxetanyl, azetidinyl, piperidinyl, morpholinyl, pyrrolidinyl and piperazinyl. Most preferred (2-5C)heterocycloalkyl are oxetanyl and azetidinyl.
(2-7C)Heterocycloalkyl means a heterocycloalkyl group having 2-7 carbon atoms, preferably 2-5 carbon atoms, and one or two heteroatoms selected from N, O and/or S. Preferred heteroatoms are N or O. Preferred (2-7C)heterocycloalkyl groups are azetidinyl, pyrrolidinyl, piperidinyl, piperazinyl, homopiperidinyl, morpholinyl or thiomorpholinyl. The heterocycloalkyl group may be attached via a heteroatom if feasible.
(6-10C)Aryl means an aromatic hydrocarbon group having 6-10 carbon atoms. Examples of "(6-10C)aryl" include, but are not limited to, phenyl, naphthyl, tetrahydronaphthyl or indenyl.
(1-5C)Heteroaryl means a substituted or unsubstituted aromatic group having 1-5 carbon atoms and 1-4 heteroatoms selected from N, O and/or S. The (1-5C)heteroaryl may optionally be substituted. Examples of "(1-5C)heteroaryl" include, but are not limited to, tetrazolyl, imidazolyl, pyridyl, pyrimidyl, triazinyl, thienyl furyl, pyrolyl or pyrazolyl.
(3-6C)Cycloalkylamino means an amino group, monosubstituted with an cycloalkyl group containing 3-6 carbon atoms having the same meaning as previously defined.
(1-6C)Alkylamino means an amino group, monosubstituted with an alkyl group containing 1-6 carbon atoms having the same meaning as previously defined. Preferred (1-6C) alkylamino group is methylamino.
Di[(1-2C)alkyl]amino means an amino group, disubstituted with alkyl group(s), each independently containing 1-2 carbon atoms and having the same meaning as previously defined. Preferred di[(1-2C)alkyl]amino group is dimethylamino.
Di[(1-6C)alkyl]amino means an amino group, disubstituted with alkyl group(s), each independently containing 1-6 carbon atoms and having the same meaning as previously defined. Preferred di[(1-6C)alkyl]amino group is N-methylpropan-1-amino.
(2-7C)Heterocycloalkylamino means an amino group, monosubstituted with a (2-7)heterocycloalkyl group containing 2-7 carbon atoms having the same meaning as previously defined.
(1-6C)Alkylaminocarbonyl means a carbonyl group substituted with an amino group. Said amino group being monosubstituted with an alkyl group having 1-6 carbon atoms and having the same meaning as previously defined.
(2-7C)Heterocycloalkylcarbonyl means a carbonyl group substituted with an (2-7C)heterocycloalkyl group having 2-7 carbon atoms and having the same meaning as previously defined.
(1-5C)Alkoxycarbonyl means a carbonyl group substituted with an alkoxy group the alkyl moiety of which having 1-6 carbon atoms as previously defined.

(1-6C)Alkylsulfonyl means a sulfonyl group substituted with an (1-6C)alkyl group having 1-6 carbon atoms and having the same meaning as previously defined.

(1-6C)Alkylcarbonyl means a carbonyl group substituted with an (1-6C)alkyl group having 1-6 carbon atoms and having the same meaning as previously defined.

(3-6C)Cycloalkylcarbonyl means a carbonyl group substituted with an (3-6C)cycloalkyl group having 3-6 carbon atoms and having the same meaning as previously defined.

(1-6C)Alkylaminocarbonyl means a carbonyl group substituted with an amino group. Said amino group being monosubstituted with an alkyl group having 1-6 carbon atoms and having the same meaning as previously defined.

(1-6C)Alkylcarbonylamino means an amino group substituted with a carbonyl group. Said carbonyl group being monosubstituted with an alkyl group having 1-6 carbon atoms and having the same meaning as previously defined.

(3-6C)Cycloalkylcarbonylamino means an amino group substituted with a carbonyl group. Said carbonyl group being monosubstituted with a cycloalkyl group having 3-6 carbon atoms and having the same meaning as previously defined.

(2-7C)Heterocycloalkylcarbonylamino means an amino group substituted with a carbonyl group. Said carbonyl group being monosubstituted with a (2-7C)heterocycloalkyl group having 2-7 carbon atoms and having the same meaning as previously defined.

Hydroxy(1-2C)alkyl means a (1-2C)alkyl group having 1-2 carbon atoms with the same meaning as previously defined, substituted with a hydroxyl group.

(1-2C)Alkoxy[(2-4C)alkoxy]$_n$(1-6C)alkyl means a (1-6C) alkyl group having 1-6 carbon atoms with the same meaning as previously defined, substituted with one or more (2-4C)alkyloxy groups, wherein n represents an integer of 1, 2, 3 or 4, the alkoxy groups being linearly connected one to another. The last (2-4C)alkyloxy group being substituted with an (1-2C)alkyloxy group. In the (1-2C)alkoxy[(2-4C)alkoxy]$_n$(1-6C)alkyl group, the preferred (1-2C)alkoxy group is methoxy, the preferred (2-4C)alkoxy is ethoxy, and the preferred (1-6C)alkyl is ethyl, preferably n is 1,2,3,4, n is 1 or 2 being most preferred.

(1-9C)heteroaryl means a substituted or unsubstituted aromatic group having 1-9 carbon atoms and 1-4 heteroatoms selected from N, O and/or S. The (1-9C)heteroaryl may optionally be substituted. Examples of "(1-9C)heteroaryl" include, but are not limited to, quinolone, isoquinoline, indazole benzisoxazole and indole.

(2-6C)alkenyl means a branched or unbranched alkenyl group having 2-6 carbon atoms. Examples of "(2-6C) alkenyl" include, but are not limited to, ethenyl, 2-butenyl and n-pentenyl.

(2-6C)alkynyl means a branched or unbranched alkynyl group having 2-6 carbon atoms, Examples of "(2-6C) alkynyl" include, but are not limited to, ethynyl, propynyl, n-butynyl, n-pentynyl, isopentynyl, isohexynyl or n-hexynyl.

(3-7C)heterocycloalkyl means a heterocycloalkyl group having 3-7 carbon atoms, preferably 3-5 carbon atoms, and one or two heteroatoms selected from N, O and/or S. Examples of "heterocycloalkyl" include, but are not limited to, azetidinyl, pyrrolidinyl, piperidinyl, homopiperidinyl or morpholinyl.

(4-8C)heterocycloalkenyl) means a heterocycloalkenyl group having 4-8 carbon atoms, preferably 3-5 carbon atoms having a double bond therein; and 1 heteroatom selected from N, O and/or S. Examples of "heteroalkenyl" include, but are not limited to, oxycyclohexenyl and azacyclohexenyl.

Halo(1-6C)alkyl means a branched or unbranched alkyl group having 1-6 carbon atoms, in which from one up to all hydrogen atoms are replaced by a halogen as defined herein. Examples of such branched or straight chain haloalkyl groups useful in the present invention include, but are not limited to, methyl, ethyl, propyl, isopropyl, isobutyl and n-butyl substituted independently with one or more halogen atoms, e.g., fluoro, chloro, bromo and iodo. Specific examples of "haloalkyl include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

HO(1-6C)alkyl means a branched or unbranched alkyl group having 1-6 carbon atoms, in which one, two or three hydrogen atoms are replaced by a hydroxyl group. Examples of "HO(1-6C)alkyl" include, but are not limited to, hydroxymethyl, 1-hydroxyethyl, 2-hydroxyethyl, and 1,2-dihydroxyethyl.

$H_2N$(1-6C)alkyl means a branched or unbranched alkyl group having 1-6 carbon atoms, in which one, two or three hydrogen atoms are replaced by an amino group. Examples of "$H_2N$(1-6C)alkyl" include, but are not limited to, aminomethyl, 1-aminoethyl, 2-aminoethyl, and 1,2-di-aminoethyl.

Cyano(1-6C)alkyl means a branched or unbranched alkyl group having 1-6 carbon atoms, in which one, two or three hydrogen atoms are replaced by a cyano group. Examples of "cyano(1-6C)alkyl" include, but are not limited to, cyanomethyl, 1-cyanoethyl, 2-cyanoethyl, and 1,2-dicyanoethyl.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds.

"Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The present invention will now be described in the following examples. These examples are intended to be illustrative of the invention, and are not intended to be limiting of the invention.

EXAMPLES

Methods

Cancer Cell Lines

To determine whether sensitivity of cancer-derived cells to TTK inhibitors correlates with the presence of a specific genomic marker, various TTK inhibitors were profiled in parallel on a panel of sixty-six cancer cell lines derived from different tumor origins and that have been characterized with respect to the expression and mutant status of various oncogenes and tumor suppressor genes (Uitdehaag, J. C. M., et al., PLoS ONE 9(3), e92146; 2014). The cancer cell lines used are listed in Table 1. All cell lines were purchased from the American Type Culture Collection (ATCC) (Manassas, Va., U.S.A.).

Cell Proliferation Assays

All cell lines were cultured in the media as recommended by ATCC. The culture media were purchased from Life Technologies (Bleiswijk, The Netherlands). Proliferation assays were carried out as described (Uitdehaag J. C. M., et al.) in 384-well plates with incubation with compound for 120 hours. Effects of TTK inhibitors were measured in a 9-point dilution series in duplicate. The final DMSO concentration during incubation was 0.4% (v/v) in all wells. As readout, intracellular ATP content was used as an indirect measure of cell number, using ATPlite™ 1 Step solution (Perkin Elmer, Groningen, The Netherlands). The effect of the compounds on cell growth was calculated relative to control wells containing only 0.4% (v/v) DMSO. Half maximum inhibitory potencies ($IC_{50}$s) were fitted by non-linear regression using XLfit™ 5 (ID Business Solutions, Ltd., Surrey, U.K.).

TABLE 1

Cancer cell lines used in drug sensitivity analysis.

| 769-P | AN3 CA | Daoy | KU812 | OVCAR-3 | SUP-T1 |
|---|---|---|---|---|---|
| 786-0 | AsPC-1 | DLD-1 | LNCaP FGC | PA-1 | SW48 |
| A-172 | AU-565 | DoTc2 4510 | LoVo | RKO | SW480 |
| A-204 | BT-20 | DU145 | LS 174T | RPMI-7951 | SW620 |
| A375 | BT-549 | FaDu | MCF7 | RT4 | SW948 |
| A388 | BxPC-3 | HCT116 | MeWo | SHP-77 | T24 |
| A-427 | C-33A | HCT-15 | MG-63 | SJRH30 | T986 |
| A-498 | CAL27 | HS 578T | MIA PaCa-2 | SK-N-AS | TT |
| A-549 | CCRF-CEM | J82 | MOLT-4 | SK-N-FI | U-2 OS |
| A-707 | COLO205 | Jurkat E6-1 | NCI-H460 | SNU-C2B | U-87 MG |
| ACHN | COLO829 | K-562 | NCI-H82 | SR | WA-ES-BJ |

The genetic status of the thirty-one most frequently changed cancer genes in the cell line panel has been established as either 'mutant' or 'wild-type' from public sequencing data (Garnett, M. J., et al., Nature 483: 570; 2012). In Table 2 the cell lines are listed that have CTNNB1 gene mutations. A427, LS 174T, HCT116 and SW48 have mutations in the serine or threonine residues that regulates the stability of β-catenin via phosphorylation at specific serine and threonine residues (Polakis, P., Curr. Opin. Gen. Dev. 9: 15; 1999). The other cell lines listed in the table and the cell lines from the sixty-six cancer cell line panel that are not mentioned, either have CTNNB1 mutations that are not implicated in regulation of protein stability, or do not have any CTNNB1 gene mutation.

Analysis of Cell Panel Response Data

Analysis of variance (Anova) was used to determine whether there was a statistical correlation between a particular genetic change in the panel of cell lines and drug sensitivity. The mutations and the $^{10}$log $IC_{50}$ from the cell proliferation assays were analyzed with a type II Anova

TABLE 2

CTNNB1 gene mutations in cancer cell lines included in the drug sensitivity analysis.

| Cell line | Codon change | Amino acid change | Zygosity | Literature reference | Mutations in regulatory domain |
|---|---|---|---|---|---|
| A427 | 121A > G | T41A | homozygous | 1,2 | Yes |
| LS 174T | 134C > T | S45F | | 2,3 | Yes |
| HCT 116 | 131-133delCTT | S45del | heterozygous | 1,2,4,5 | Yes |
| SW48 | 98C > A | S33Y | heterozygous | 1,2,4,5 | Yes |
| Other | | | | | |
| C33A | 1216G > A | P406I | heterozygous | 1 | no |
| DU145 | 914C > G | A305G | homozygous | 1,4 | no |
| LNCap | 1154T > A | I385H | heterozygous | 1 | no |
| T98G | 526C > T | B176Y | heterozygous | 1 | no |
| U2OS | 1584-1G > A (intronic substitution) | | heterozygous | 1 | no |
| COLO205 | E562 splice | | diploid | 4 | no |

Figure 2B:
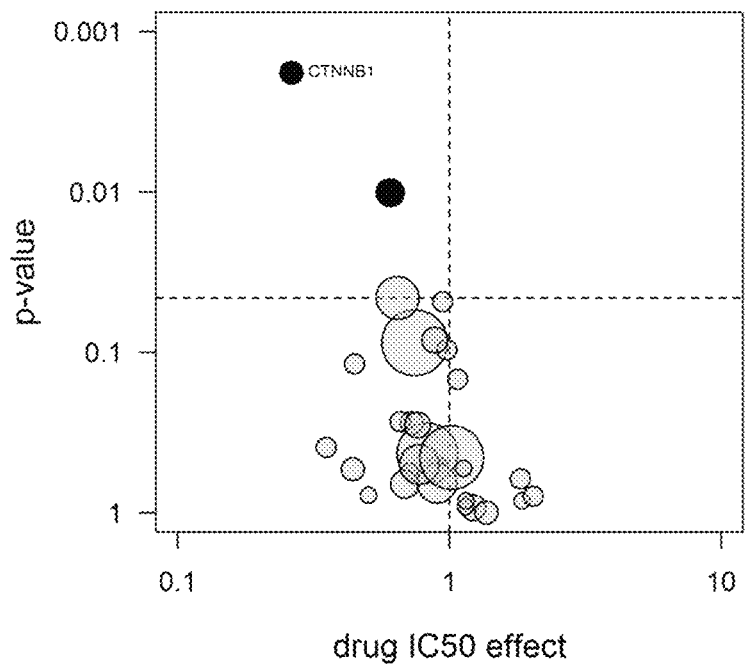
Figure 2C:
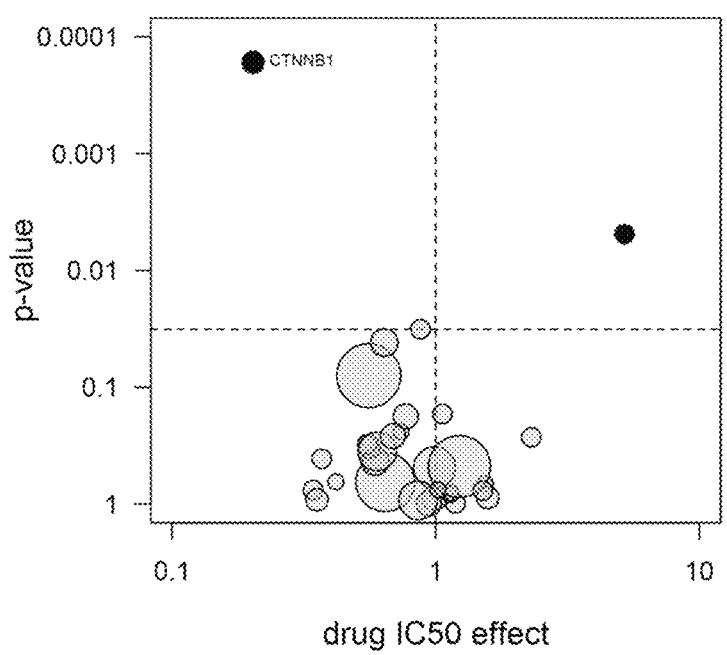
Figure 2D:
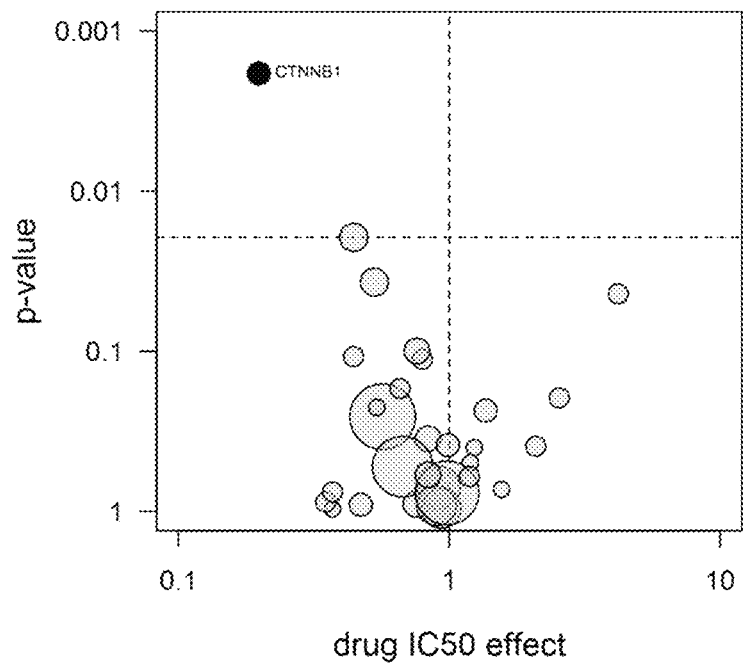
Figure 2E:
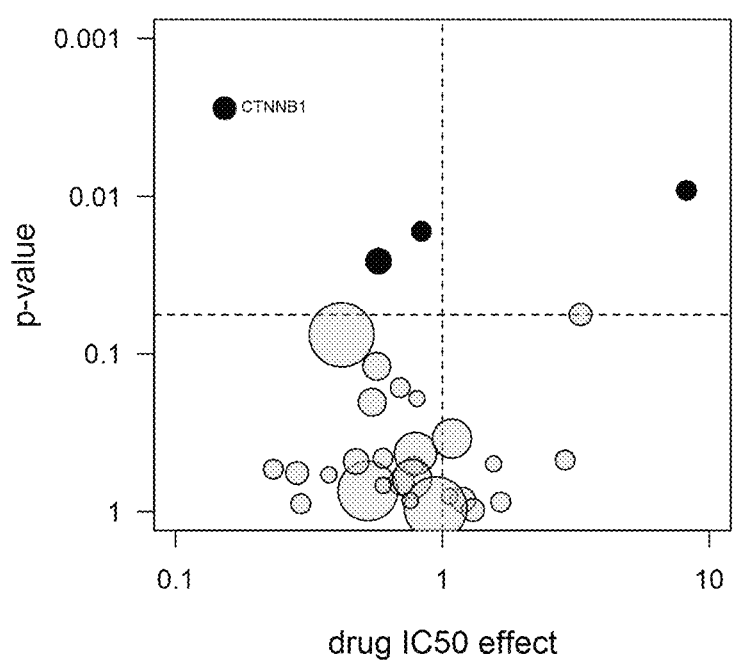
Figure 2F:
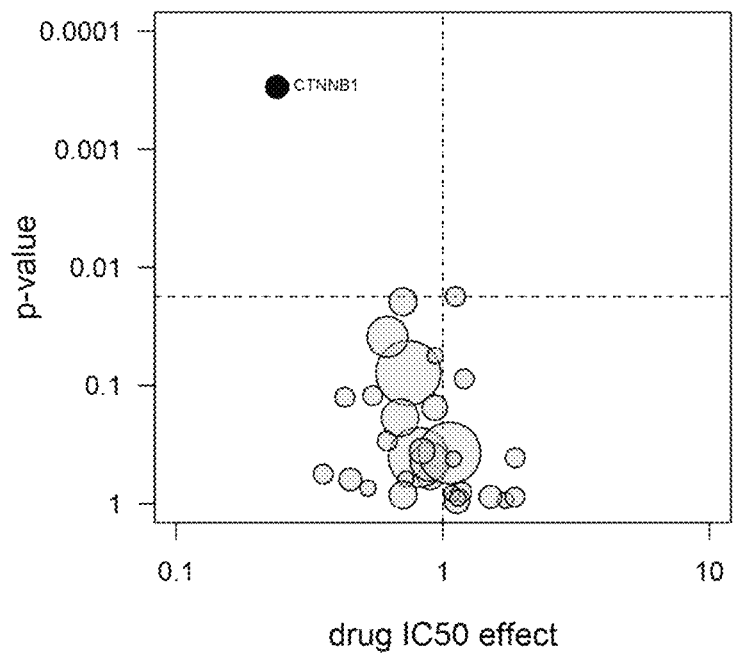
Figure 2G:
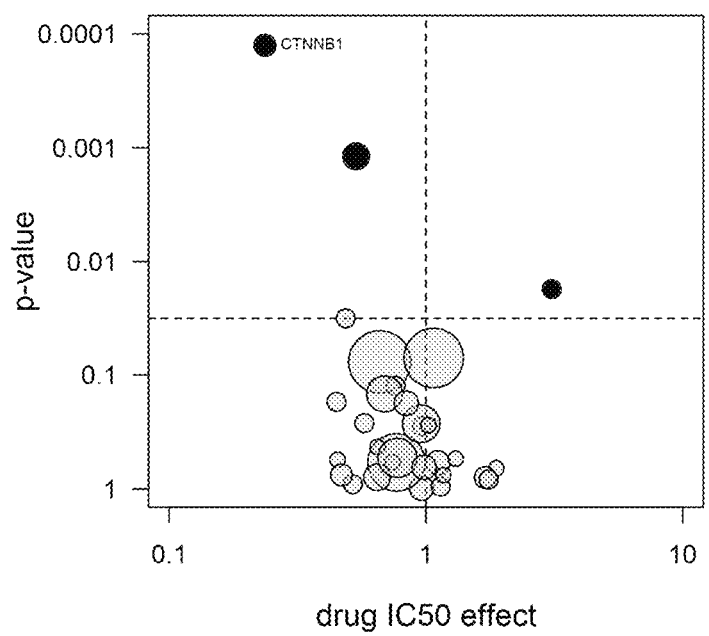

References
1. Cosmic Cell Lines project, status Feb. 2$^{nd}$, 2015
2. Garnett, M. J., et al.
3. Wang, Z., et al., Cancer Res. 63: 5234; 2003
4. Cancer Cell Line Encyclopedia, status Feb. 2$^{nd}$, 2015
5. Morin, et al., 1997; Ilyas, M., et al., Proc. Natl. Acad. Sci. USA 94: 10330; 1997 analysis using the statistical program R (R Foundation for statistical computing, Vienna, Austria) and displayed in volcano plots such as shown in FIGS. 2A-2G. The p-value (y-axis in the volcano plot) indicates the confidence level for genetic association of mutations in a particular gene with a $IC_{50}$ shift. The average factor with which the $IC_{50}$ shifts is indicated on the x-axis. The areas of the circles are proportional to the number of mutants in the cell panel (each mutation is present at least twice). To compute significance, p-values were subjected to a Benjamini-Hochberg multiple testing correction (Benjamini, Y., and Hochberg, Y., J. Royal. Statistic. Soc. B 57:289; 1995). Genetic associations with a<20% false discovery rate were considered significant.

Statistical Analysis of Difference in Sensitivity

To quantify differences in sensitivity between CTNNB1-mutant and CTNNB1 proficient, the inhibitory potency of the TTK inhibitors was expressed as $pIC_{50}$ ($-^{10}\log IC_{50}$). A two-tailed Student's t-test was performed to determine whether differences in sensitivity ($\Delta pIC_{50}$) between CTNNB1 mutant and CTNNB1 proficient cells were statistically significant (i.e., p<0.05).

Comparison of Sensitivity in Isogenic Cell Lines

To determine whether mutated CTNNB1 was sufficient to confer increased sensitivity to TTK inhibitors, proliferation assay were performed with a pair of isogenic cell lines. Parental HCT116 cells harbor a deletion of three base pairs in one copy of the CTNNB1 gene, resulting in deletion of the regulatory serine residue at position 45 (S45del) of β-catenin (Table 2). Parental HCT116 cells are furthermore heterozygous regarding mutation in the CTNNB1 gene, i.e., the genotype of parental HCT116 regarding CTNNB1 is S45del/+. An isogenic cell line derived from HCT116 lacking the mutated CTNNB1 gene copy (+/−) was purchased from Horizon Discovery (Cambridge, U.K.) (Chan, T. A., et al., Proc. Natl. Acad. Sci. USA 99: 8265; 2002). HCT116 parental and isogenic derivatives were cultured in identical media, as recommended by the supplier. Proliferation assays were carried out as described for cancer cell lines (Uitdehaag J. C. M., et al.). Dose response curves were plotted, $IC_{50}$, $pIC_{50}$ and maximum percentage effect (efficacy) were calculated using XLfit™ 5. Difference in sensitivity of the parental and the isogenic derivative were expressed as difference in $pIC_{50}$ ($\Delta pIC_{50}$) and difference in efficacy ($\Delta$efficacy).

TTK Inhibitors (Examples 1 to 31)

The following examples are illustrative embodiments of the invention, not limiting the scope of the invention in any way. Reagents are either commercially available or are prepared according to procedures in the literature.

Method LCMS (A)

| | | |
|---|---|---|
| Method name | NTRC_C18_Short.M | |
| Column | Waters XTerra C18-MS, 50 × 4.6 mm ID, 2.5 μm | |
| Flow | 0.5 ml/min. | |
| Temperature | 40° C. | |
| Detector DAD | 210, 254, 280 nm | |
| Detector MSD | API-ES | |
| MSD signal | 1 | 2 |
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |
| Sample preparation | N/A | |
| Concentration | 1 mg/ml in MeOH or CAN | |
| Injection volume | 1.0 μl | |
| Eluent | A | B |
| Time [min] | % 0.1% Formic Acid | % 0.05% Formic Acid in Acetonitrile |
| 0 | 90 | 10 |
| 0.3 | 90 | 10 |
| 7.0 | 10 | 90 |
| 7.1 | 90 | 10 |
| 10.0 | 90 | 10 |
| Post time | 0.2 min     Stop time | 10 min |

Method LCMS (B)

| | | |
|---|---|---|
| Method name | NTRC_C18.M | |
| Column | Waters XTerra C18-MS, 50 × 4.6 mm ID, 2.5 μm | |
| Flow | 0.5 ml/min. | |
| Temperature | 40° C. | |
| Detector DAD | 210, 254, 280 nm | |
| Detector MSD | API-ES | |
| MSD signal | 1 | 2 |
| Mode | Scan | Scan |
| Polarity | Positive | Negative |

-continued

| | | |
|---|---|---|
| Mass Range | 100-1000 m/z | 100-1000 m/z |
| Fragmentor | 70 | 70 |
| Cycle Time | 50% | 50% |

| | | |
|---|---|---|
| Sample preparation | N/A | |
| Concentration | 1 mg/ml in MeOH or CAN | |
| Injection volume | 1.0 µl | |

| Eluent | A | B |
|---|---|---|
| Time [min] | % 0.1% Formic Acid | % 0.05% Formic Acid in Acetonitrile |
| 0 | 90 | 10 |
| 1 | 90 | 10 |
| 22.0 | 10 | 90 |
| 22.1 | 90 | 10 |
| 30.0 | 90 | 10 |
| Post time | 0.2 min   Stop time | 30 min |

Method LCMS (C)

| | |
|---|---|
| LC System | HP1200SL |
| Column | Agilent Eclipse plus C18 150 mm × 2.1 mm ID 3.5 µm |
| Column temperature | 40° C. |
| Sample(s) | ca 1 mg/mL |
| Autosampler temperature | 20° C. |
| Injection volume | 5 µl |
| Flow | 0.5 ml/min |
| Type of Pump | Binary |
| Eluent | A = MilliQ + 0.1% Formic Acid |
| | B = Acetonitrile |

| | time (min) | % A | % B |
|---|---|---|---|
| Gradient | 0 | 90 | 10 |
| | 1 | 90 | 10 |
| | 22 | 10 | 90 |
| | 22.1 | 90 | 10 |
| | 30 | 90 | 10 |

| | |
|---|---|
| Next Injection delay | 0 min |
| UV detection | UV 210, 240, 280 nm |
| Flowcell DAD | 10 mm |

| | |
|---|---|
| MS system | Agilent 6130 single Quad MS |
| Source | ESI |
| Mode | Positive (+) |
| Mass range | 100-1000 Da |
| Flow | The total flow was split to a suitable flow infused directly in the APCI/ESI multimode source of the Agilent 6130 |

Method Preparative HPLC

| | |
|---|---|
| LC System | Waters Prep System |
| Column | Phenomenex Luna, C18(2) 100 A, 150 mm × 21.2 mm, 5 µm |
| Column Temp | 20° C. |
| Sample(s) | 10-50 mg |
| Autosamp. Temp | 20° C. |
| Injection volume | 500-950 µL |
| Flow | 15 ml/min |
| Eluent | A = MilliQ + MeCN (9/1) |
| | B = Acetonitrile |

| | time (min) | % A | % B | % C |
|---|---|---|---|---|
| Gradient | 0 | 97 | 0 | 3 |
| | 20 | 37 | 60 | 3 |
| | 25 | 37 | 60 | 3 |

| | 25.1 | 97 | 0 | 3 |
| | 30 | 97 | 0 | 3 |
| UV detection | | Photo Diode Array | | |

The following abbreviations are used throughout the application with respect to chemical terminology:
TFA Trifluoracetic acid
HATU O-(7-Azabenzotriazol-1-yl)-1,1,3,3-tetramethyluroniumhexafluorophosphate
DMF N,N-Dimethylformamide
THF Tetrahydrofuran
MeOH Methanol
EtOAc Ethyl acetate
DCM Dichloromethane
$Na_2SO_4$ Sodium sulfate
TMS-Cl Chlorotrimethylsilane
DiPEA N,N-Diisopropylethylamine
EtOH Ethanol
10% Pd/C 10% Palladium on charcoal
HPLC High Performance Liquid Chromatography
LCMS Liquid Chromatography with Mass Spectrometry detection
NaOH Sodium hydroxide
KOH Potassium hydroxide
HCl Hydrogen chloride
$NaHCO_3$ Sodium bicarbonate
4-DMAP 4-Dimethylamino pyridine
Boc tert-Butyloxycarbonyl
Cbz Benzyloxycarbonyl
$HNO_3$ Nitric acid
LiHMDS Lithium bis(trimethylsilyl)amide
DDQ 2,3-Dichloro-5,6-dicyano-p-benzoquinone
DEAD Diethyl azodicarboxylate
o/n overnight The names of the final products in the examples are generated using Accelrys Draw (version 4.1).

Example 1 (WITJ0018D)

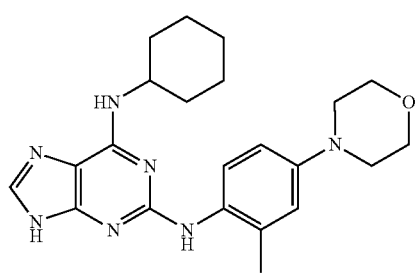 [SMILES: Cc1cc(N2CCOCC2)ccc1Nc1nc(NC2CCCCC2)c2nc[nH]c2n1]

N6-cyclohexyl-N2-(2-methyl-4-morpholino-phenyl)-9H-purine-2,6-diamine

This compound was prepared as described in WO2010/111406 A2 and Bioorg. Med. Chem. Letters 22 (2012) 4377. Purification was performed using preparative HPLC to afford the title compound (338 mg). Data: LCMS (C) $R_t$: 10.995 min; m/z 408.3 $(M+H)^+$.

Example 2 JGS0282C)

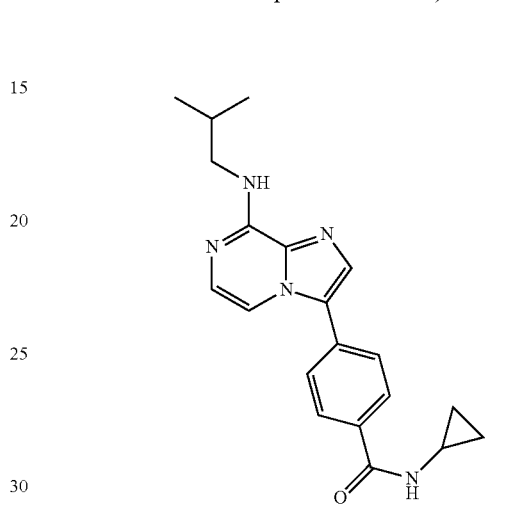

N-cyclopropyl-4-[8-(isobutylamino)imidazo[1,2-a]pyrazin-3-yl]benzamide

This compound was prepared as described in WO2012/080229 A1 and Cell Death and Differentiation 20 (2013), 1532. Purification was performed using preparative HPLC to afford the title compound (47 mg). Data: LCMS (B) $R_t$: 8.088 min; m/z 350.2 $(M+H)^+$.

Example 3 (BTHO238B)

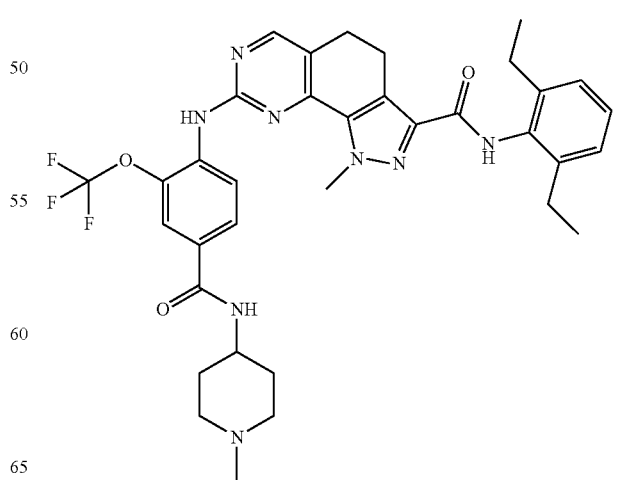

23

N-(2,6-diethylphenyl)-1-methyl-8-[4-[(1-methyl-4-piperidyl)carbamoyl]-2-(trifluoromethoxy)anilino]-4,5-dihydropyrazolo[4,3-h]quinazoline-3-carboxamide This compound was prepared as described in WO2009/156315 A1 and Cancer Res. 70 (2010), 10255. Purification was performed using preparative HPLC to afford the title compound (191 mg). Data: LCMS (A) $R_t$: 5.810 min; m/z 677.6 (M+H)$^+$.

Example 4 (WITJ113B)

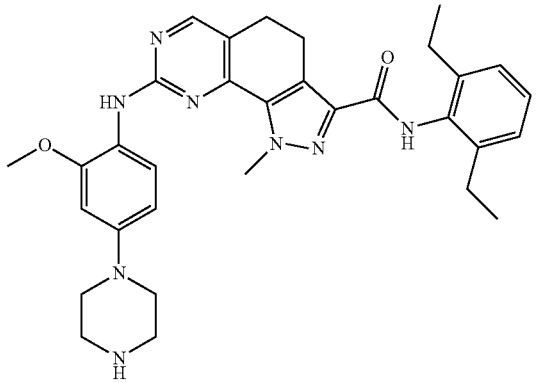 [SMILES: CCc1cccc(CC)c1NC(=O)c1nn(C)c2c1CCc1cnc(Nc3ccc(N4CCNCC4)cc3OC)nc1-2]

N-(2,6-diethylphenyl)-8-(2-methoxy-4-piperazin-1-yl-anilino)-1-methyl-4,5-dihydropyrazolo[4,3-h]quinazoline-3-carboxamide This compound was prepared as described in WO2009/156315 A1. Purification was performed using preparative HPLC to afford the title compound (7.3 mg). Data: LCMS (C) $R_t$: 12.954 min; m/z 567.3 (M+H)$^+$.

Example 5 (JGS0716D)

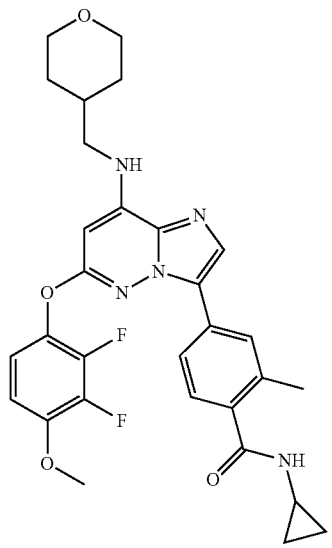 [SMILES: COc1ccc(Oc2cc(NCC3CCOCC3)c3ncc(-c4ccc(C(=O)NC5CC5)c(C)c4)n3n2)c(F)c1F]

24

N-cyclopropyl-4-[6-(2,3-difluoro-4-methoxy-phenoxy)-8-(tetrahydropyran-4-ylmethylamino)imidazo[1,2-b]pyridazin-3-yl]-2-methyl-benzamide This compound was prepared as described in WO 2014/131739 A1. Purification was performed using preparative HPLC to afford the title compound (90 mg). Data: LCMS (B) $R_t$: 13.496 min; m/z 564.5 (M+H)$^+$.

Example 6 (JGS0728A)

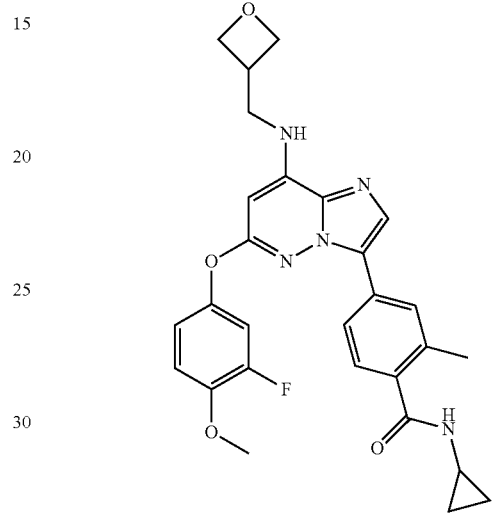

N-cyclopropyl-4-[6-(3-fluoro-4-methoxy-phenoxy)-8-(oxetan-3-ylmethylamino)imidazo[1,2-b]pyridazin-3-yl]-2-methyl-benzamide This compound was prepared as described in WO 2014/131739 A1. Purification was performed using preparative HPLC to afford the title compound (45 mg). Data: LCMS (B) $R_t$: 11.640 min; m/z 518.4 (M+H)$^+$.

Intermediate 1

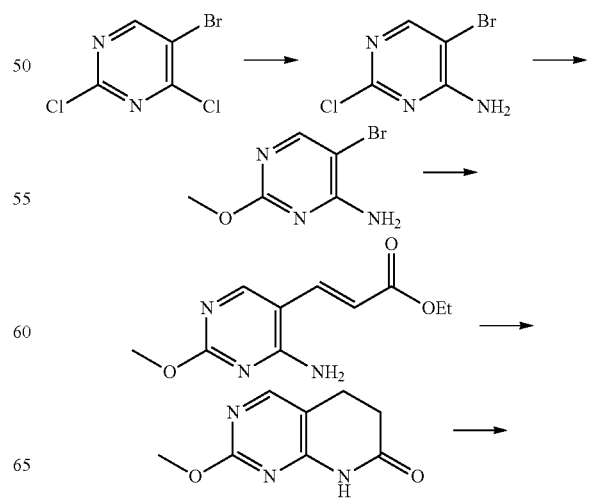

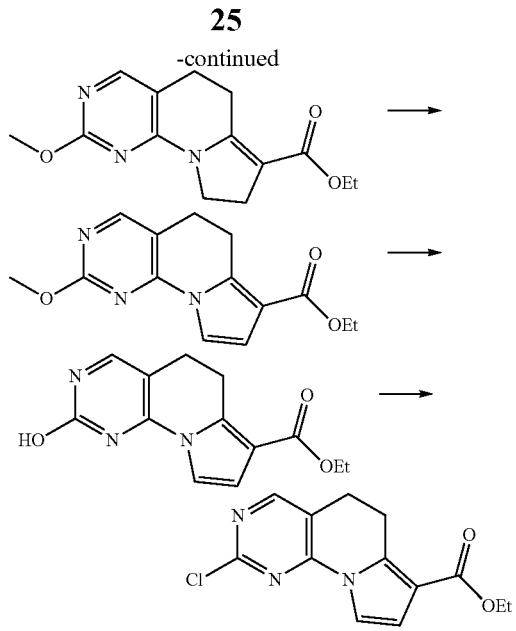

Ethyl 2-chloro-5,6-dihydropyrimido[4,5-e]indolizine-7-carboxylate (a) 5-Bromo-2-chloro-pyrimidin-4-amine (WITJ0221)

To a solution of 5-bromo-2,4-dichloro-pyrimidine (150 g; 658 mmol) in THF (445 mL) was added ammonium hydroxide (25% in water, 250 mL) and the resulting reaction mixture was stirred at room temperature for 90 min. The mixture was subsequently concentrated in vacuo to a small volume and partitioned between ethyl acetate and water. The organic phase was separated and washed with water and brine, dried over sodium sulfate, filtered and concentrated to give 137.3 g (quant. yield) of 5-bromo-2-chloro-pyrimidin-4-amine.

(b) 5-Bromo-2-methoxy-pyrimidin-4-amine (WITJ0223)

To a suspension of 5-bromo-2-chloro-pyrimidin-4-amine (137.3 g, 658 mmol) in methanol (1 L) was added portionwise sodium methoxide (83.5 g; 1.54 mol). The reaction mixture was stirred for 2 h. at reflux. The reaction mixture was concentrated to a small volume (~400 mL) and poured into a saturated solution of ammonium chloride in water (1.2 L). This mixture was allowed to stir for 15 min, after which the water layer was extracted with ethyl acetate. The combined ethyl acetate layers were washed with brine, dried over sodium sulfate, filtered and concentrated to yield 5-bromo-2-methoxypyrimidin-4-amine (133.7 g, 99.4%).

(c) Ethyl (E)-3-(4-amino-2-methoxy-pyrimidin-5-yl)prop-2-enoate 256) (WITJ0256)

Palladium(II) acetate (1.21 g, 5.5 mmol) and triphenylphosphine (3.40 g, 13.0 mmol) were dissolved in anhydrous and oxygen-free DMF (53 mL) and stirred for 5 min at 30° C. to give an orange suspension. To this suspension was added a solution of 5-bromo-2-methoxypyrimidin-4-amine (44.1 g, 216 mmol) in DMF (270 mL), triethylamine (60.2 mL, 432 mmol) and a solution of ethyl acrylate (23.5 mL, 216 mmol) in DMF (50 mL). The reaction mixture was stirred at 100° C. o/n under a nitrogen atmosphere. The reaction mixture was evaporated to a small volume. Water (300 mL) and brine (300 mL) were added to the mixture, followed by an extraction with ethyl acetate (300 mL, twice). The combined organic layers were washed with water, brine, dried over sodium sulfate and concentrated in vacuo. The crude product was purified by silica column chromatography (ethyl acetate:heptane=2:1 v/v %) to yield the title compound (38.2 g, 77%).

(d) 2-Methoxy-6,8-dihydro-5H-pyrido[2,3-d]pyrimidin-7-one (WITJ0262)

To a stirred solution of ethyl (E)-3-(4-amino-2-methoxy-pyrimidin-5-yl)prop-2-enoate (12.52 g, 56.1 mmol) in methanol (250 mL) was added a suspension of 10% Pd on charcoal (1.19 g) in methanol/ethanol=3/1 v/v % (30 mL). The reaction mixture was stirred at room temperature for 15 min under nitrogen atmosphere. Then, ammonium formate (35.3 g, 561 mmol) was added and the resulting reaction mixture was refluxed o/n. After cooling of the reaction mixture, a fresh portion of ammonium formate (20 g, 317 mmol) was added and stirring was continued an additional night at reflux. The reaction mixture was filtered over Decalite® and the Pd—C/Decalite® residue was washed with dichloromethane/methanol=8/2 v/v % and the filtrate was concentrated in vacuo. The residue was dissolved in dichloromethane and washed with water, dried over sodium sulfate, filtered and concentrated in vacuo to obtain 9.4 g (94%) of 2-methoxy-6,8-dihydro-5H-pyrido[2,3-d]pyrimidin-7-one.

(e) Ethyl 2-methoxy-5,6,8,9-tetrahydropyrimido[4,5-e]indolizine-7-carboxylate (JGS0241)

2-Methoxy-6,8-dihydro-5H-pyrido[2,3-d]pyrimidin-7-one (4.79 g, 26.8 mmol) was suspended in THF (200 mL) in a three-necked flask (500 mL), equipped with a mechanical stirrer, a thermometer and a reflux condenser. The mixture was cooled to 0° C. and sodium hydride (60% dispersion in oil, 1.18 g, 29.4 mmol) was added in two batches. The mixture was stirred at 0° C. for 30 min. (1-ethoxycarbonyl-cyclopropyl)triphenylphosphonium tetrafluoroborate (13.6 g, 29.4 mmol) was added and the resulting suspension was heated to reflux and kept at reflux temperature for 3 days. The reaction mixture was cooled to room temperature and poured in a 1/1/1 mixture of brine/water/EtOAc (450 mL). The water layer was extracted with ethyl acetate (2×). The combined organic layers were washed with water and brine, dried over sodium sulfate, filtered and concentrated in vacuo to give 18.05 g of an orange oil. The crude product was used directly in the next step without purification.

(f) Ethyl 2-methoxy-5,6-dihydropyrimido[4,5-e]indolizine-7-carboxylate (JGS244)

To a stirred solution of ethyl 2-methoxy-5,6,8,9-tetrahydropyrimido[4,5-e]indolizine-7-carboxylate (18.05 g, 26.2 mmol) in dichloromethane (100 mL) was added acetic acid (3.15 g, 3 mL) and lead(IV)acetate (13.9 g, 31.4 mmol). The reaction mixture was stirred for 2 h at room temperature then filtered over a PE filter to remove Pb-salts and the Pb-residue was washed with 2×30 mL DCM. The filtrate was concentrated in vacuo and the resulting residue was dissolved in ethyl acetate (300 mL). A solution of sodium bicarbonate (5%) was added until pH~8.5. Both the organic and the water layers were filtered over Decalite® to remove any remaining salts. The water layer was subsequently extracted with EtOAc (2×50 mL). The combined organic layers were washed with 5% sodium bicarbonate-solution (100 mL), water (100 mL), brine (50 mL), dried (Na$_2$SO$_4$), filtered and concentrated in vacuo. The crude product was purified by column chromatography on silica (heptane: ethyl acetate=I/O to 1/1 v/v %) to yield the title compound (4.74 g, 66% over two steps).

(g) Ethyl 2-hydroxy-5,6-dihydropyrimido[4,5-e]indolizine-7-carboxylate (JGS0245)

Sodium iodide (7.83 g, 52.2 mmol) was added to a stirred solution of ethyl 2-methoxy-5,6-dihydropyrimido[4,5-e]indolizine-7-carboxylate (4.74 g, 17.3 mmol) in acetonitrile (150 mL). Trimethylsilyl chloride (5.64 g, 6.59 mL) dissolved in acetonitrile (30 mL) was added drop-wise to the reaction mixture and the mixture was stirred at room temperature o/n. NaI (1 eq) was added and additional TMS-Cl (0.94 g, 1.1 mmol) in acetonitrile (6 mL) was added drop-wise and the reaction was stirred for 3 days at room temperature. The mixture was concentrated and the residue was suspended in 200 mL DCM/MeOH (4/1) and extracted with a mixture of saturated solution of sodium thiosulfate (200 mL) and water (200 mL). The water layer was extracted with 3×150 mL DCM/MeOH (4/1). The combined organic layers were dried over sodium sulfate, filtered and the solvent was removed under reduced pressure to give a yellow solid. The residue was dried at 40° C. under vacuum for 18h to give 3.89 g ethyl 2-hydroxy-5,6-dihydropyrimido[4,5-e]indolizine-7-carboxylate (86%).

(h) Ethyl 2-chloro-5,6-dihydropyrimido[4,5-e]indolizine-7-carboxylate (Intermediate 1) (JGS0278)

N,N-dimethylaniline (182 mg, 191 uL, 1.50 mmol) was added to a solution of ethyl 2-hydroxy-5,6-dihydropyrimido[4,5-e]indolizine-7-carboxylate (3.89 g, 15.0 mmol) in acetonitrile (100 mL). A solution of phosphorus(V) oxychloride (11.5 g, 7.00 mL, 75.0 mmol) in acetonitrile (15 mL) was added drop-wise to the reaction mixture. The yellow suspension was heated for 4 hours to 65° C. during which the suspension turned into a clear solution. After cooling, the mixture was slowly poured in a stirred mixture of 25% aq. ammonia (200 mL, 86.7 eq.) and ice-water (250 mL) keeping the temperature below 10° C. in 15-20 minutes. After stirring for another 15 minutes the solids were filtered. The solids were dissolved in 200 mL EtOAc and washed with brine (20 mL). The organic layer was dried over sodium sulfate, and concentrated in vacuo to give an off-white solid. The crude product was purified by column chromatography on silica (heptane/ethyl acetate=1/0 to 1/1 v/v %) to yield the title compound (3.05 g, 73%).

Intermediate A

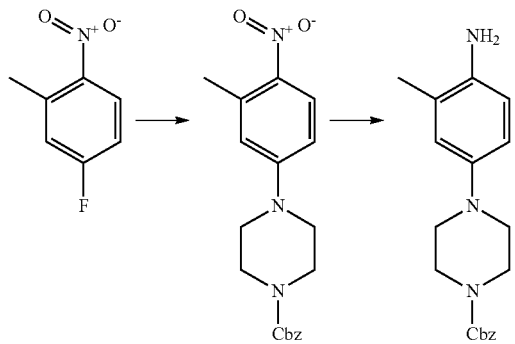

Benzyl 4-(4-amino-3-methyl-phenyl)piperazine-1-carboxylate

(a) Benzyl 4-(3-methyl-4-nitro-phenyl)piperazine-1-carboxylate (WITJ404)

Benzyl piperazine-1-carboxylate (1.05 mL, 5.25 mmol) and potassium carbonate (1.38 g, 10 mmol) were added to a solution of 4-fluoro-2-methyl-1-nitro-benzene (776 mg, 5 mmol) in DMF (10 mL) and the resulting mixture was stirred at 100° C. for 18 h. Water was added to the reaction mixture and extraction performed with ethyl acetate. The combined organic layers were washed with brine, dried over sodium sulfate and concentrated in vacuo. The crude product was purified by silica column chromatography (heptane/ethyl acetate=I/O to 6/4 v/v %) to yield the title compound (1.75 g, 98%).

(b) Benzyl 4-(4-amino-3-methyl-phenyl) piperazine-1-carboxylate (Intermediate A) (WITJ406)

Benzyl 4-(3-methyl-4-nitro-phenyl)piperazine-1-carboxylate (355 mg, 1 mmol) was dissolved in THF (5 mL) and acetic acid (1.1 mL) was added. The mixture was cooled to 0° C. and zinc (1.31 g, 20 mmol) was added in small portions to keep the temperature below 20° C. The reaction mixture was stirred at room temperature o/n. After TLC analysis indicated a complete conversion of the starting material, the mixture was filtered over Decalite® and the Zn-Decalite® residue was washed with EtOAc (20 mL). The combined filtrates were washed with a 1N NaOH-solution (25 mL), followed by water (25 mL) and brine (25 mL). The organic layer was dried (Na$_2$SO$_4$), filtered and concentrated in vacuo to give benzyl 4-(4-amino-3-methyl-phenyl)piperazine-1-carboxylate (327 mg, quantitative).

Intermediate 2

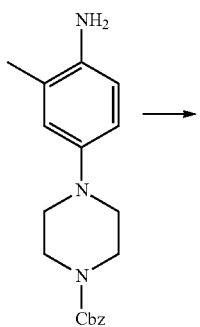

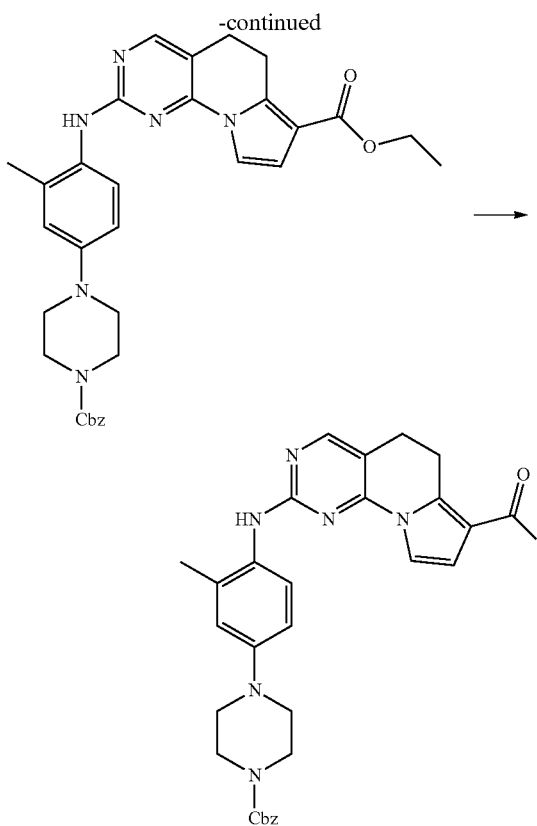

Benzyl 4-[4-[(7-chlorocarbonyl-5,6-dihydropyrimido[4,5-e]indolizin-2-yl)amino]-3-methyl-phenyl]piperazine-1-carboxylate (a) Ethyl 2-[4-(4-benzyloxycarbonylpiperazin-1-yl)-2-methyl-anilino]-5,6-dihydropyrimido[4,5-e]indolizine-7-carboxylate (WITJ407)

To a suspension of ethyl 2-chloro-5,6-dihydropyrimido[4,5-e]indolizine-7-carboxylate (Intermediate 1, 292 mg, 1.05 mmol) in n-butanol (8 mL) was added benzyl 4-(4-amino-3-methyl-phenyl)piperazine-1-carboxylate (Intermediate A, 327 mg, 1.0 mmol) and trifluoroacetic acid (153 L 2.0 mmol). The reaction mixture was heated for 12 hours at 120° C. under microwave radiation. The reaction mixture was concentrated in vacuo and the residue was dissolved in ethyl acetate. The organic layer was washed with a saturated solution of sodium bicarbonate, dried over sodium sulfate, filtered and concentrated in vacuo. The crude product was purified by silica column chromatography (heptane/ethyl acetate=4/6 to 0/1 v/v %). Fractions containing product were collected and evaporated to afford ethyl 2-[4-(4-benzyloxycarbonylpiperazin-1-yl)-2-methyl-anilino]-5,6-dihydropyrimido[4,5-e]indolizine-7-carboxylate (423 mg, 75% yield).

(b) Benzyl 4-[4-[(7-chlorocarbonyl-5,6-dihydropyrimido[4,5-e]indolizin-2-yl)amino]-3-methyl-phenyl]piperazine-1-carboxylate (Intermediate 2) (WITJ408/WITJ414)

To a solution of ethyl 2-[4-(4-benzyloxycarbonylpiperazin-1-yl)-2-methyl-anilino]-5,6-dihydropyrimido[4,5-e]indolizine-7-carboxylate (423 mg, 0.75 mmol) in 15 mL absolute ethanol was added a 2M NaOH-solution (935 µL (2.5 eq). 1.87 mmol). The reaction mixture was heated at 65° C. o/n. Reaction mixture was evaporated to dryness and dried under high vacuum. The resulting residue was dissolved in water, stirred o/n at room temperature and lyophilised to yield the crude sodium 2-[4-(4-benzyloxycarbonylpiperazin-1-yl)-2-methyl-anilino]-5,6-dihydropyrimido[4,5-e]indolizine-7-carboxylate.

Thionyl chloride (561 µL, 7. mmol) was added to a cold (0° C.) suspension of the crude sodium 2-[4-(4-benzyloxycarbonylpiperazin-1-yl)-2-methyl-anilino]-5,6-dihydropyrimido[4,5-e]indolizine-7-carboxylate (217 mg, 0.39 mmol theor.) in dichloromethane (8 mL). The resulting slurry was stirred at room temperature o/n. The reaction mixture was concentrated in vacuo and the residue was co-evaporated with toluene (2×10 mL) to give of benzyl 4-[4-[(7-chlorocarbonyl-5,6-dihydropyrimido[4,5-e]indolizin-2-yl)amino]-3-methyl-phenyl]piperazine-1-carboxylate as a yellow/brown powder (261 mg, quant. crude yield).

Example 7 (WITJ0416/WITJ429A)

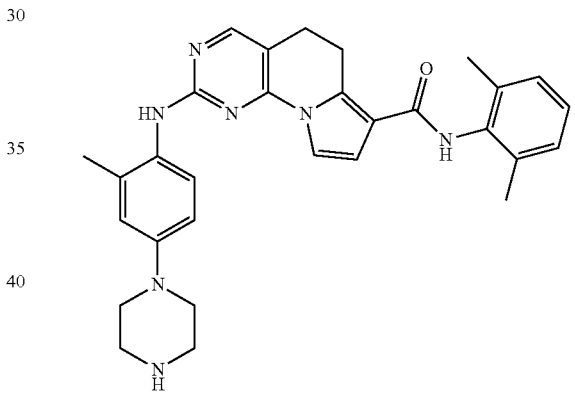

N-(2,6-dimethylphenyl)-2-(2-methyl-4-piperazin-1-yl-anilino)-5,6-dihydropyrimido[4,5-e]indolizine-7-carboxamide To a suspension of benzyl 4-[4-[(7-chlorocarbonyl-5,6-dihydropyrimido[4,5-e]indolizin-2-yl)amino]-3-methyl-phenyl]piperazine-1-carboxylate (Intermediate 2, 45 mg, 0.081 mmol theor.) in acetonitrile (3 mL) was added 2,6-dimethylaniline (15 µL, 0.12 mmol) and a catalytic amount of 4-DMAP. The reaction mixture was stirred at 50° C. for 1 h. After evaporation of the solvent, the Cbz-group was de-protected using TFA/thioanisole and the crude product was purified by preparative HPLC. Fractions containing product were collected and concentrated in vacuo. The residue was partitioned between dichloromethane and 5% NaHCO$_3$-solution. The organic phase was separated over a PE-filter and evaporated to afford the title compound (20 mg, 64%). Data: LCMS (B) R$_t$: 9.706 min; m/z 508.3 (M+H)$^+$.

Example 8 (JGS439C)

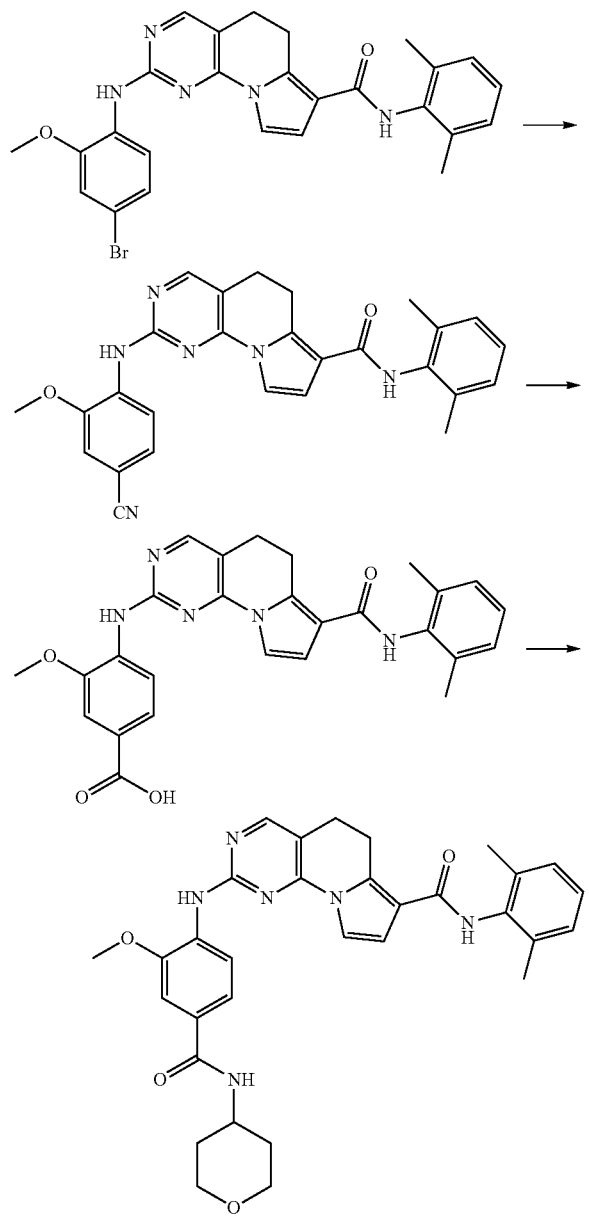

N-(2,6-dimethylphenyl)-2-[2-methoxy-4-(tetrahydropyran-4-ylcarbamoyl)anilino]-5,6-dihydropyrimido[4,5-e]indolizine-7-carboxamide (a) 2-(4-Bromo-2-methoxy-anilino)-N-(2,6-dimethylphenyl)-5,6-dihydropyrimido[4,5-e]indolizine-7-carboxamide (JGS453)

This compound was prepared from its corresponding acid chloride, using the same sequence of reactions, as described for Intermediate 2, using commercially available 4-bromo-2-methoxyaniline as starting material. The acid chloride was subsequently reacted with 2,6-dimethylaniline according to procedures described in Example 7 to afford the title compound (1.35 g, 84%).

(b) 2-(4-Cyano-2-methoxy-anilino)-N-(2,6-dimethylphenyl)-5,6-dihydropyrimido[4,5-e]indolizine-7-carboxamide (JGS455)

To a solution of 2-(4-bromo-2-methoxy-anilino)-N-(2,6-dimethylphenyl)-5,6-dihydropyrimido[4,5-e]indolizine-7-carboxamide (1.35 g, 2.6 mmol) and zinc cyanide (321 mg, 2.73 mmol) in DMF (4 mL) was added tetrakis(triphenylphosphine)palladium(0) (300 mg, 0.26 mmol). The reaction mixture was heated for 30 minutes at 170° C. under microwave radiation. After cooling to ambient temperature, the mixture was concentrated and the residue was diluted with ethyl acetate, washed with water and brine, dried over sodium sulfate, filtered and concentrated in vacuo to afford the crude title compound (1.05 g, 87%).

(c) 4-[[7-[(2,6-Dimethylphenyl)carbamoyl]-5,6-dihydropyrimido[4,5-e]indolizin-2-yl]amino]-3-methoxy-benzoic acid (JGS0457)

To a stirred suspension of 2-(4-cyano-2-methoxy-anilino)-N-(2,6-dimethylphenyl)-5,6-dihydropyrimido[4,5-e]indolizine-7-carboxamide (750 mg, 1.61 mmol) in MeOH (25 mL) was added a solution of potassium hydroxide (453 mg, 8.07 mmol) in water (12.5 mL). The reaction mixture was heated for 2 hours at 120° C. under microwave radiation. After evaporation of the methanol fraction, the resulting water layer was acidified by addition of 2N HCl-solution until pH-2. After extraction with dichloromethane, the combined organic layers were filtered over a PE-filter to give 330 mg of the title compound (yield: 42%).

(d) N-(2,6-dimethylphenyl)-2-[2-methoxy-4-(tetrahydropyran-4-ylcarbamoyl)anilino]-5,6-dihydropyrimido[4,5-e]indolizine-7-carboxamide (JGS439C)

4-[[7-[(2,6-Dimethylphenyl)carbamoyl]-5,6-dihydropyrimido[4,5-e]indolizin-2-yl]amino]-3-methoxy-benzoic acid (30 mg, 0.062 mmol) was dissolved in N,N-dimethylformamide (3 ml). HATU (25.9 mg, 0.068 mmol) and N,N-diisopropylethylamine (43.1 µL, 0.25 mmol) were subsequently added and the mixture was stirred for 10 min at room temperature. 4-Aminotetrahydropyran hydrochloride (12.8 mg, 0.093 mmol) was added and the mixture was stirred at room temperature o/n. The mixture was poured into a mixture ethyl acetate/water/brine (1/1/1) and stirred for 15 min. The organic layer was separated, washed with brine, dried over sodium sulphate filtered and concentrated in vacuo. Purification was performed using preparative HPLC to afford the title compound (5 mg, 18%). Data: LCMS (B) $R_t$: 14.407 min; m/z 567.3 (M+H)⁺.

Intermediate B (NV0068/NV0076)

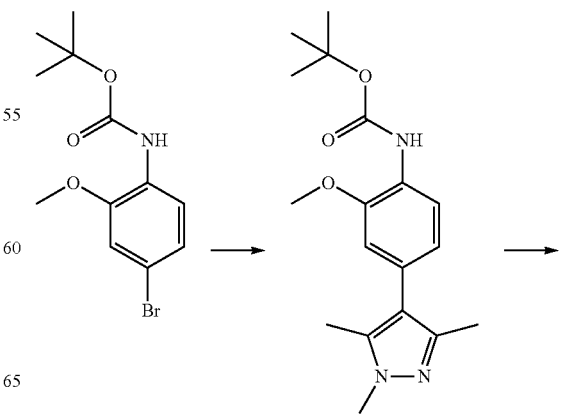

-continued

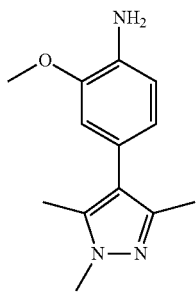

2-Methoxy-4-(1,3,5-trimethylpyrazol-4-yl)aniline (a) tert-Butyl N-[2-methoxy-4-(1,3,5-trimethylpyrazol-4-yl)phenyl]carbamate (NV0068)

A mixture of tert-butyl N-(4-bromo-2-methoxy-phenyl) carbamate (150 mg, 0.5 mmol), 1,3,5-trimethyl-4-(4,4,5,5-tetramethyl-1,3,2-dioxaborolan-2-yl)pyrazole (118 mg, 0.5 mmol), tetrakis(tri-phenylphosphine)palladium(0) (58 mg, 0.05 mmol) and potassium carbonate (207 mg, 1.5 mmol) in dioxane (4 mL) was heated at 100° C. under microwave irradiation for 20 minutes in a sealed tube. After cooling to ambient temperature, the mixture was concentrated and the residue was diluted with ethyl acetate, washed with water and brine, dried over sodium sulfate, filtered and concentrated in vacuo. The residue was purified by column chromatography (heptane/ethyl acetate=100/0 to 25/75 v/v %) to afford tert-butyl N-[2-methoxy-4-(1,3,5-trimethylpyrazol-4-yl)phenyl]carbamate (126.8 mg, 77%).

(b) 2-Methoxy-4-(1,3,5-trimethylpyrazol-4-yl)aniline (Intermediate B) (NV0076)

tert-Butyl N-[2-methoxy-4-(1,3,5-trimethylpyrazol-4-yl)phenyl]carbamate (127 mg, 0.38 mmol) was dissolved in DCM (2 mL). TFA (3 mL) was added and the reaction mixture was stirred for 1 hour at room temperature. The mixture was concentrated in vacuo to give a brown oil (313 mg) that was used without further purification.
Intermediate C (JDM0438/JDM035)

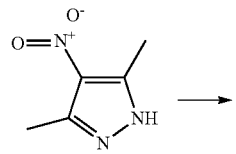

-continued

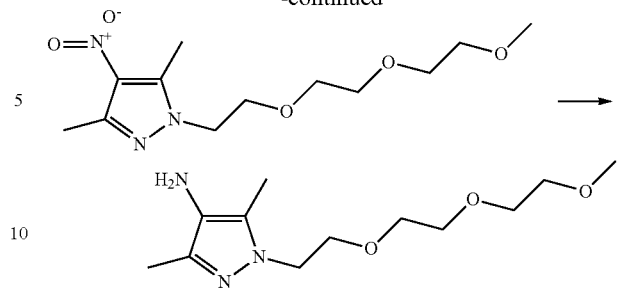

1-[2-[2-(2-Methoxyethoxy)ethoxy]ethyl]-3,5-dimethyl-pyrazol-4-amine (a) 1-[2-[2-(2-Methoxyethoxy)ethoxy]ethyl]-3,5-dimethyl-4-nitro-pyrazole To a cold (0° C.) solution of 3,5-dimethyl-4-nitro-1H-pyrazole (250 mg, 1.77 mmol), triethylene glycol monomethylether (482 µL, 3.01 mmol) and triphenylphosphine (789 mg, 3.01 mmol) in THF (10 mL) was added dropwise a solution of 40% DEAD in toluene (1.31 mL, 3.01 mmol) The reaction mixture was allowed to warm to room temperature and was stirred for 3 h. Ethyl acetate was added and washed with a 10% NaCl-solution. The organic layer was dried (Na₂SO₄), filtered and concentrated. The residue was purified by column chromatography (DCM/MeOH=99/1 to 95/5 v/v %) to afford 1-[2-[2-(2-methoxyethoxy)ethoxy]ethyl]-3,5-dimethyl-4-nitro-pyrazole (1.7 g, crude) which was used without purification in the next step.

(b) 1-[2-[2-(2-methoxyethoxy)ethoxy]ethyl]-3,5-dimethyl-pyrazol-4-amine (Intermediate C)

1-[2-[2-(2-Methoxyethoxy)ethoxy]ethyl]-3,5-dimethyl-4-nitro-pyrazole (1.5 g, 1.77 mmol theor.) was dissolved in THF (15 mL) and acetic acid (1.6 mL) was added. The mixture was cooled to 0° C. and zinc (2.3 g, 35.4 mmol) was added in small portions keeping the temperature below 20° C. The reaction mixture was stirred at room temperature o/n. After TLC analysis indicated a complete conversion of the starting material, the mixture was filtered over Decalite® and the Zn-Decalite® residue was washed with ethyl acetate. The combined filtrates were washed with a 1N NaOH-solution, followed by water and brine. The organic layer was dried (Na₂SO₄), filtered and concentrated in vacuo. The residue was dissolved in methanol and then filtered over a SCX-2 column. After rinsing the column with methanol, the desired product was eluted with an 0.7 N ammonia/methanol solution to give the title compound (340.1 mg, 74.7%).

Example 9 (JDM0641A)

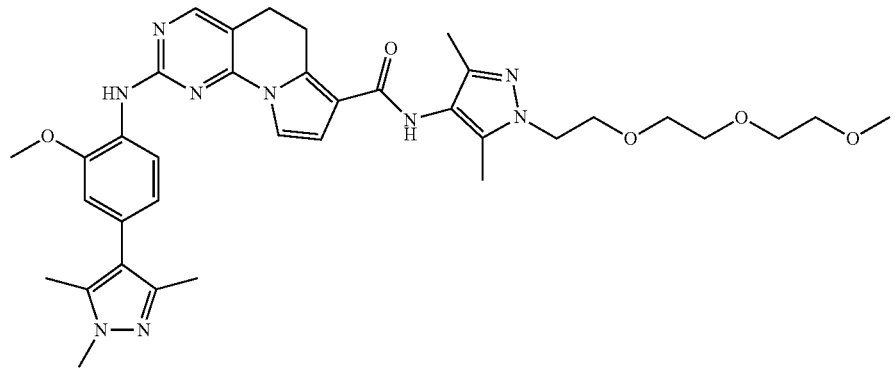

N-[1-[2-[2-(2-methoxyethoxyethoxy]ethyl]-3,5-dimethyl-pyrazol-4-yl]-2-[2-methoxy-4-(1,3,5-trimethylpyrazol-4-yl) anilino]-5,6-dihydropyrimido[45-e]indolizine-7-carboxamide This compound was prepared from its corresponding acid, using the same sequence of reactions, as described for Intermediate 2b, using Intermediate B as starting material. The carboxylic acid was subsequently reacted with Intermediate C in an analogous manner as described for Example 8d. Purification was performed using preparative HPLC to afford the title compound (19.5 mg, 42.6%). Data: LCMS (B) $R_t$: 10.946 min; m/z 684.7 (M+H).

Intermediate D (JGS88/92)

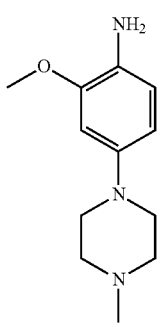

2-Methoxy-4-(4-methylpiperazin-1-yl)aniline

This compound was prepared in an analogous manner as described for Intermediate A, starting from N-methylpiperazine and 2-methoxy-4-fluoronitrobenzene to afford the title compound (1.38 g, 94%).

Example 10 (JDM0443A)

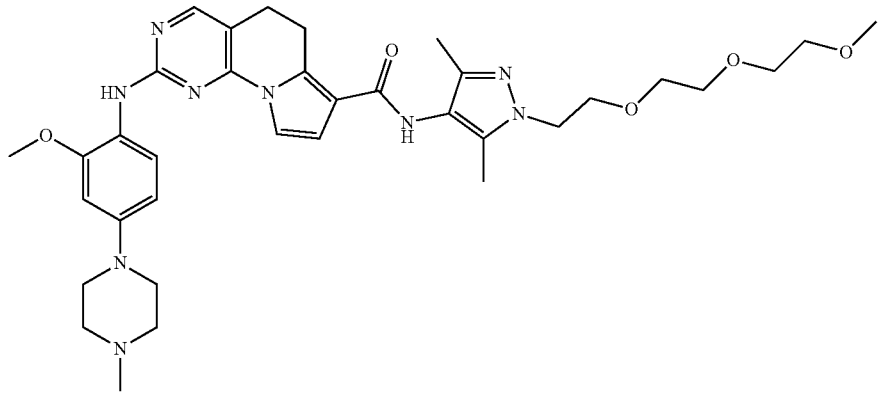

N-[1-[2-[2-(2-methoxyethoxy)ethoxy]ethyl]-3,5-dimethyl-pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate D as starting material. The acid chloride was subsequently reacted with Intermediate C according to procedures described in Example 8d. Purification was performed using preparative HPLC to afford the title compound (11.6 mg, 28.6%). Data: LCMS (B) $R_t$: 6.985 min; m/z 674.3 (M+H)$^+$.

Example 11 (JGS79C)

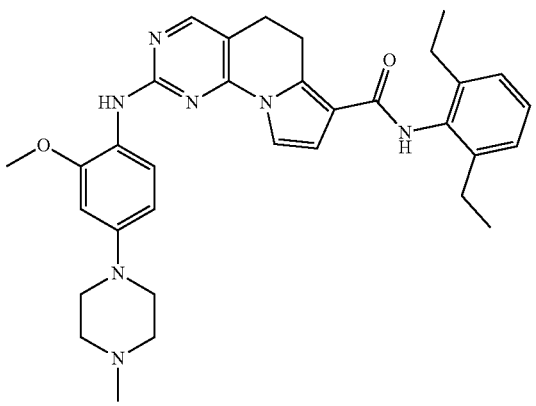 [SMILES: CCc1cccc(CC)c1NC(=O)c1ccn2c1CCc1cnc(Nc3ccc(N4CCN(C)CC4)cc3OC)nc1-2]

N-(2,6-diethylphenyl)-2-[2-methoxy-4-(4-methylpiperazin-1-yl)anilino]-5,6-dihydropyrimido[4,5-e]indolizine-7-carboxamide This compound was prepared from its corresponding ester, using the same sequence of reactions as described for Intermediate 2a using Intermediate D as starting material. LiHDMS (1M in THF/ethylbenzene, 412 μL, 0.412 mmol) was added to a cold (0° C.) solution of 2,6-diethylaniline (50.8 μL, 0.31 mmol) in THF (1 mL). After 15 minutes of stirring at 0° C., ethyl 2-[2-methoxy-4-(4-methylpiperazin-1-yl)anilino]-5,6-dihydropyrimido[4,5-e]indolizine-7-carboxylate (48 mg, 0.103 mmol) in THF (2 mL) was added drop-wise to the reaction mixture and stirring was continued for 90 min at 0° C. Additional LiHMDS (100 μL) was added drop-wise at room temperature and stirring was continued for 2 hours at room temperature. The reaction mixture was quenched with 20 mL saturated solution of ammonium chloride and extracted with ethyl acetate. The combined organic layers were washed with water, brine, dried over sodium sulfate, filtered and concentrated under reduced pressure. Purification was performed using preparative HPLC to afford the title compound (13.5 mg, 23.2%). Data: LCMS (C) $R_t$: 12.686 min; m/z 566.4 (M+H)$^+$.

Intermediate E (/WITJ437WITJ438/WITJ440)

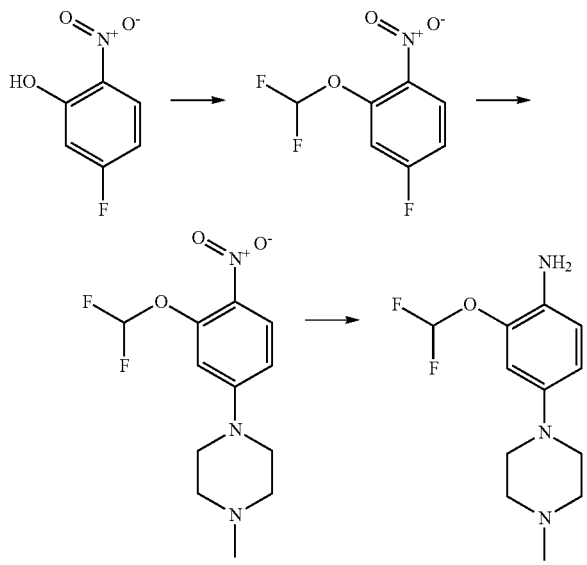

2-(Difluoromethoxy)-4-(4-methylpiperazin-1-yl)
aniline

To a solution of 5-fluoro-2-nitro-phenol (500 mg, 3.18 mmol) in DMF (6 ml) was added sodium 2-chloro-2,2-difluoro-acetate (970 mg, 6.36 mmol) and disodium carbonate (405 mg, 3.82 mmol). The reaction mixture was stirred at 100° C. for 3.5 hours and subsequently at room temperature for 3 days. A 4M HCl-solution was added until a clear solution was obtained and the mixture was stirred for 2 h at room temperature. The reaction mixture was diluted with water and extracted with EtOAc. The combined organic layers were washed with 1M NaOH-solution, brine, dried over sodium sulphate, filtered and concentrated in vacuo. The residue was purified by column chromatography (heptane/ethyl acetate=10/0 to 8/2 v/v %) to afford 2-(difluoromethoxy)-4-fluoro-1-nitro-benzene (493 mg, 75%).

The title compound was prepared in an analogous manner as described for Intermediate A, starting from N-methylpiperazine and 2-(difluoromethoxy)-4-fluoro-1-nitro-benzene to afford 180 mg (80%).

Intermediate F (JDM300/WITJ410/WITJ411/WITJ413)

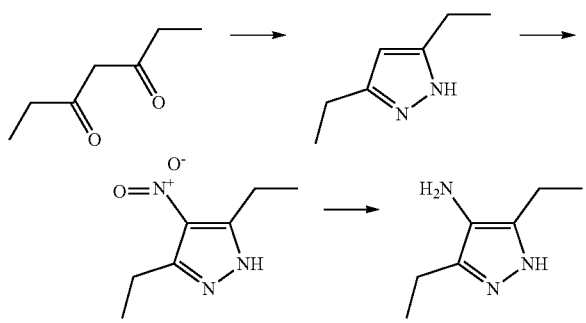

3,5-Diethyl-1H-pyrazol-4-amine (a) 3,5-Diethyl-1H-pyrazole

To a solution of 3,5-heptanedione (2 g, 15.6 mmol) and hydrazine hydrate (0.77 g, 15.8 mmol) in water (10 mL) was added acetic acid (1 drop) and the reaction mixture was heated to reflux for 1 h. The reaction mixture was then cooled, and concentrated under reduced pressure to provide 1.8 g of the title compound. This compound was used directly in the next step without purification.

(b) 3,5-Diethyl-4-nitro-1H-pyrazole

To a cold (0° C.) mixture of 3,5-diethyl-1H-pyrazole (1.8 g, 14.5 mmol) and concentrated sulphuric acid (1.5 ml) was added slowly, under vigorous stirring, fuming $HNO_3$ (4.35 ml). The reaction mixture was stirred overnight at 60° C. The mixture was subsequently cooled to room temperature, then carefully added to an ice-cold saturated solution of sodium bicarbonate and stirred for 15 min. The mixture was then extracted three times with EtOAc and combined organic layers were washed with brine, dried over sodium sulphate, filtered and evaporated in vacuo to give: 2.52 g 3,5-diethyl-4-nitro-1H-pyrazole.

(c) 3,5-Diethyl-1H-pyrazol-4-amine (Intermediate F)

The title compound was prepared in an analogous manner as described for Intermediate C, starting from 3,5-diethyl-4-nitro-1H-pyrazole to give 3,5-diethyl-1H-pyrazol-4-amine (174 mg, 71%).

Example 12 (WITJ453B)

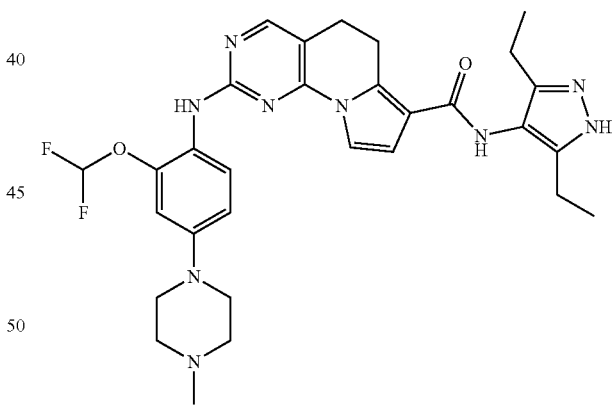

N-(3,5-diethyl-1H-pyrazol-4-yl)-2-[2-(difluoromethoxy)-4-(4-methylpiperazin-1-yl)anilino]-5,6-dihydropyrimido[4,5-e]indolizine-7-carboxamide This compound was prepared from its corresponding carboxylic acid, using the same sequence of reactions as described for Intermediate 2b, using Intermediate E as starting material. The carboxylic acid was subsequently reacted with Intermediate F in an analogous manner as described for Example 8d. Purification was performed using preparative HPLC to afford the title compound (9.6 mg, 23%). Data: LCMS (B) $R_t$: 8.864 min; m/z 592.3 (M+H)+.

Intermediate G (JDM617/JDM622/JDM630)

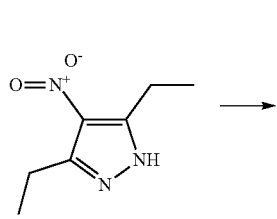

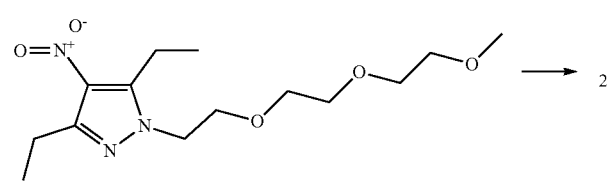

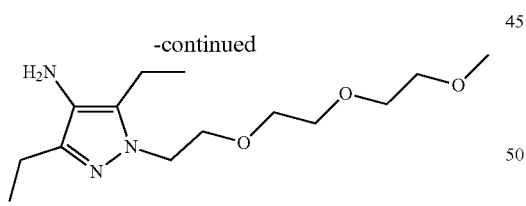

3,5-Diethyl-1-[2-[2-(2-methoxyethoxy)ethoxy]ethyl]pyrazol-4-amine

The title compound was prepared in an analogous manner as described for Intermediate C, starting from 3,5-diethyl-4-nitro-1H-pyrazole (Intermediate Fb) and triethylene glycol monomethyl ether to give 660 mg of 3,5-diethyl-1-[2-[2-(2-methoxyethoxy)ethoxy]ethyl]pyrazol-4-amine (41.7%).

Intermediate M (WITJ461/WITJ4587)

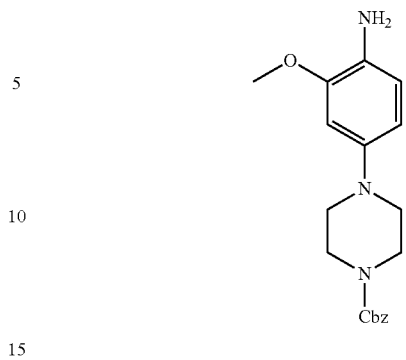

Benzyl 4-(4-amino-3-methoxy-phenyl)piperazine-1-carboxylate

This compound was prepared in an analogous manner as described for Intermediate A, starting from benzyl piperazine-1-carboxylate and 2-methoxy-4-fluoronitrobenzene to afford the title compound (1.2 g, 95%).

Example 13 (JDM0684A)

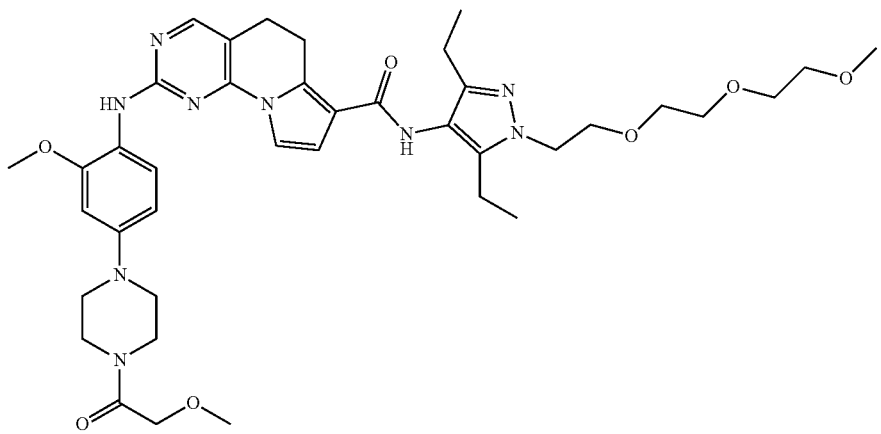

N-[3,5-diethyl-1-[2-[2-(2-methoxyethoxy) ethoxy] ethyl]pyrazol-4-yl]-2-[2-methoxy-4-[4-(2-methoxyacetyl)piperazin-1-yl]anilino]-5,6-dihydropyrimido[4,5-e]indolizine-7-carboxamide This compound was prepared from its corresponding amine (prepared as described for Example 7 starting from Intermediate 1 and Intermediate M) and methoxyacetic acid, using standard HATU-coupling procedures as described in Example 8d. Purification was performed using preparative HPLC to afford the title compound (17.8 mg, 57.1%). Data: LCMS (B) $R_t$: 9.908 min; m/z 760.8 (M+H)$^+$.

Intermediate H (JDM221/JDM0222/JDM393)

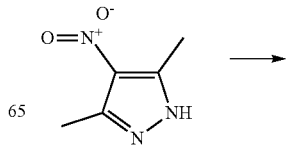

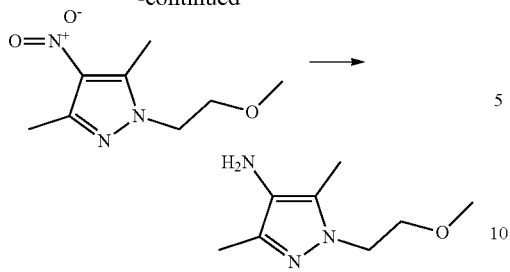

1-(2-Methoxyethyl)-3,5-dimethyl-pyrazol-4-amine

(a) 1-(2-Methoxyethyl)-3,5-dimethyl-4-nitro-pyrazole

To a solution of 3,5-dimethyl-4-nitro-1H-pyrazole (2.5 g, 17.7 mmol) and caesium carbonate (6.06 g, 18.6 mmol) in DMF (50 mL) was added 2-bromoethyl methyl ether (2.59 g, 1.75 mL, 18.6 mmol). The mixture was heated at 100° C. for 3.5 h. After cooling to room temperature, the mixture was poured into water and extracted with ethyl acetate (3×50 mL). The combined organic layers were washed with brine (50 mL), dried over sodium sulfate, filtered and concentrated under reduced pressure. The residue was purified by column chromatography (EtOAc/heptanes=1/4 v/v %) to afford 1-(2-methoxyethyl)-3,5-dimethyl-4-nitro-pyrazole (2.66 g, 75.4%) as a white crystalline solid.

(b) 1-(2-Methoxyethyl)-3,5-dimethyl-pyrazol-4-amine 1-(2-Methoxyethyl)-3,5-dimethyl-4-nitro-pyrazole (245 mg, 1.22 mmol) was dissolved in methanol (25 mL). The resulting solution was hydrogenated using a H-Cube continuous-flow hydrogenation reactor, 10% Pd/C, at 30° C., 8-10 bar, 1 mL/min, full H$_2$ modus. The resulting solution was concentrated in vacuo to yield 208 mg (quant. yield) of the title compound as a light-brown oil.

Intermediate I (JDM464/JDM450)

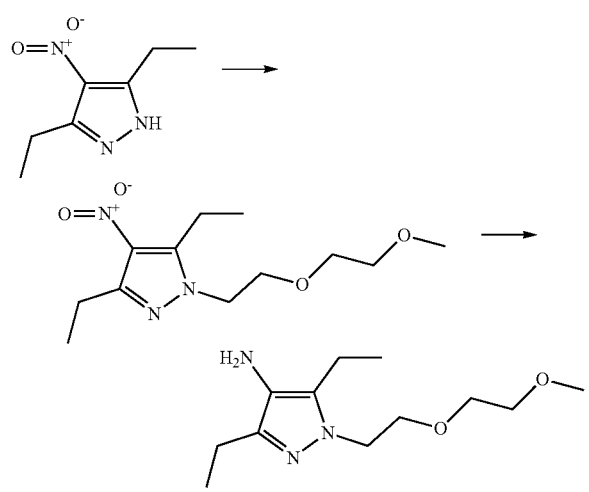

3,5-Diethyl-1-[2-(2-methoxyethoxy)ethyl]pyrazol-4-amine

The title compound was prepared in an analogous manner as described for Intermediate H, starting from 3,5-diethyl-4-nitro-1H-pyrazole (Intermediate Fb) and 1-bromo-2-(2-methoxyethoxy)-ethane to give 290 mg of 3,5-diethyl-1-[2-(2-methoxyethoxy)ethyl]pyrazol-4-amine (72.2%.).

Example 14 (JDM0466A)

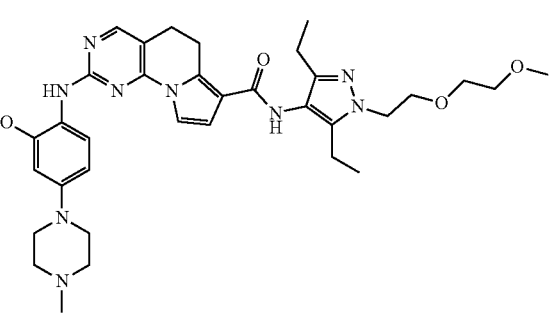

N-[3,5-diethyl-1-[2-(2-methoxy)ethyl]pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate D as starting material. The acid chloride was subsequently reacted with Intermediate I according to procedures described in Example 7. Purification was performed using preparative HPLC to afford the title compound (22 mg, 54.4%). Data: LCMS (B) R$_t$: 7.845 min; m/z 658.3 (M+H).

Intermediate J (WITJ277/WITJ84)

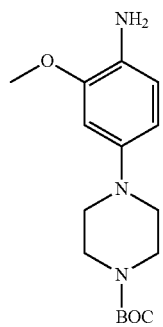 [SMILES: COc1cc(N2CCN(C(=O)OC(C)(C)C)CC2)ccc1N]

tert-Butyl 4-(4-amino-3-methoxy-phenyl)piperazine-1-carboxylate

This compound was prepared in an analogous manner as described in Intermediate A, starting from tert-butyl piperazine-1-carboxylate and 2-methoxy-4-fluoronitrobenzene to afford the title compound (245 mg, 91%).

Example 15 (WITJ349B)

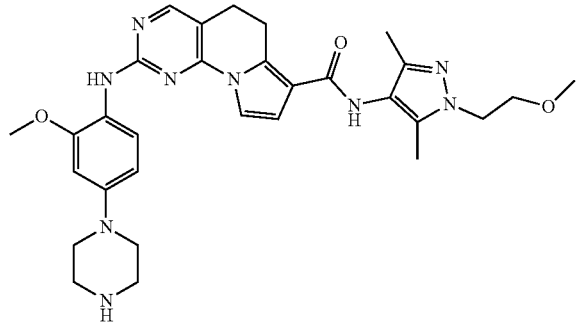

N-[1-(2-methoxyethyl-3,5-dimethyl-pyrazol-4-yl]-2-(2-methoxy-4-piperazin-1-yl-anilino)-5,6-dihydropyrimido[4,5-e]indolizine-7-carboxamide Ethyl 2-chloro-5,6-dihydropyrimido[4,5-e]indolizine-7-carboxylate (Intermediate 1, 296 mg, 1.07 mmol), tert-Butyl 4-(4-amino-3-methoxy-phenyl)piperazine-1-carboxylate (Intermediate J, 328 mg, 1.07 mmol) and cesium carbonate (1.39 g, 4.27 mmol) were suspended in dioxane (25 mL). Nitrogen was bubbled through the mixture at 30° C. for 5 minutes followed by the addition of 9,9-bis-dimethyl-4,5-bis(diphenylphosphino)xanthene (62 mg, 0.11 mmol) and tris(dibenzylideneacetone)dipalladium(0) (49 mg, 53 µmol). The reaction mixture was stirred at 80° C. for 20 hours under a flow of nitrogen gas.

Ethyl acetate/water/brine (1/1/1 v/v %, 50 mL) were added to the reaction mixture and stirring was continued for 15 min. After filtration over Decalite® the water layer was separated and extracted with ethyl acetate (2×20 mL). The combined organic layers were subsequently washed with water (40 mL), brine (20 mL), dried over sodium sulphate, filtered and concentrated in vacuo. The crude product was purified by column chromatography on silica (Heptane/Ethyl acetate=1/0 to 0/1 v/v %) to ethyl 2-[4-(4-tert-butoxycarbonylpiperazin-1-yl)-2-methoxy-anilino]-5,6-dihydropyrimido[4,5-e]indolizine-7-carboxylate (115 mg, 20%).

The thus obtained ethyl ester was subsequently hydrolysed using conditions described for Intermediate 2b. The sodium salt of the corresponding carboxylic acid was subsequently reacted with Intermediate H in an analogous manner as described for Example 8d. After de-protection of the Boc-group, purification was performed using preparative HPLC to afford the title compound (5.2 mg, 28%). Data: LCMS (B) R$_t$: 8.140 min; m/z 572.3 (M+H)$^+$.

Intermediate K (JDM25/JDM302)

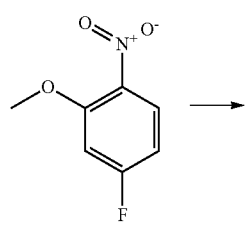

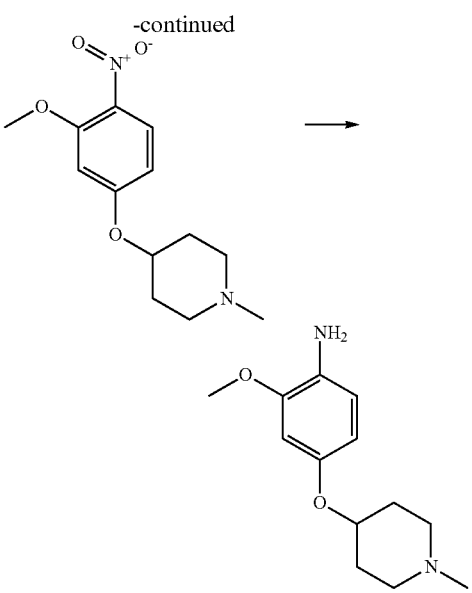

2-Methoxy-4-[1-methyl-4-piperidyloxy]aniline (a) 4-(3-Methoxy-4-nitro-phenoxy)-1-methyl-piperidine To a solution of 4-fluoro-2-methoxy-1-nitro-benzene (750 mg, 4.38 mmol) in toluene (10 mL) were added 10 mL of a 25% KOH-solution, 4-hydroxy-N-methylpiperidine (1009 mg, 8.76 mmol) and tetra-n-butyl ammonium bromide (282 mg, 0.876 mmol). The mixture was heated at 60° C. o/n. The reaction mixture was then diluted with ethyl acetate and the water layer was extracted with ethyl acetate. The combined organic layers were washed with brine, dried over sodium sulfate and evaporated. The residue was purified by flash chromatography on silica gel (dichloromethane/methanol=99/1 to 9/1 v/v %) to obtain the title compound. (650 mg, 55.7%)

(b) 2-Methoxy-4-[(1-methyl-4-piperidyl)oxy]aniline (Intermediate K)

10% Pd/C (20 mg) was added as a suspension in ethanol to a solution of 4-(3-methoxy-4-nitro-phenoxy)-1-methyl-piperidine (200 mg, 0.75 mmol) in ethanol (5 mL). The resulting mixture was stirred for 15 min at room temperature. Ammonium formate (473 mg, 7.5 mmol) was added and the reaction mixture was stirred for 1 hour at reflux under nitrogen atmosphere. The reaction mixture was cooled to room temperature and filtered over Decalite®. The filtrate was concentrated in vacuo, after which dichloromethane was added and the organic phase was washed with 5% solution of NaHCO$_3$. The organic phase was dried over sodium sulfate, filtered and concentrated in vacuo to yield 2-methoxy-4-[(1-methyl-4-piperidyl)oxy]aniline (169.5 mg, 95.6%).

Intermediate L (JDM221J/JDM0222)

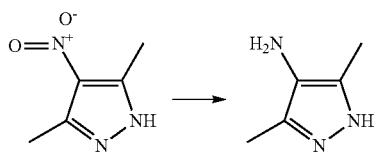

3,5-Dimethyl-1H-pyrazol-4-amine

The title compound was prepared in an analogous manner as described for Intermediate Hb, starting from 3,5-dimethyl-4-nitro-1H-pyrazole to give 110 mg 3,5-dimethyl-1H-pyrazol-4-amine (quant.).

Example 16 (JDM323A)

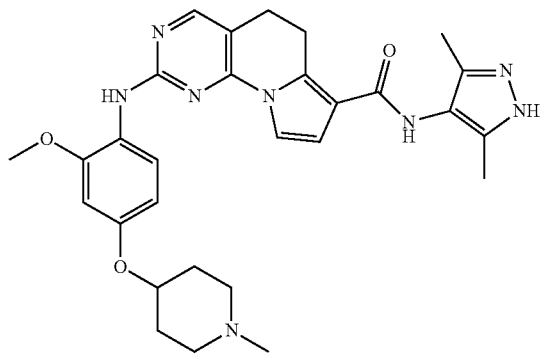 [SMILES: COc1cc(OC2CCN(C)CC2)ccc1Nc1ncc2c(n1)-n1ccc(C(=O)Nc3c(C)n[nH]c3C)c1CC2]

N-(3,5-dimethyl-1H-pyrazol-4-=(1-2-[2-methoxy-4-[(1-methyl-4-piperidyl)oxy]anilino]-5,6-dihydropyrimido[4,5-e]indolizine-7-carboxamide This compound was prepared from its corresponding acid chloride, using the same sequence of reactions, as described for Intermediate 2, using Intermediate K as starting material. The acid chloride was subsequently reacted with Intermediate L according to procedures described in Example 7. Purification was performed using preparative HPLC to afford the title compound (14.1 mg, 37%). Data: LCMS (B) $R_t$: 7.902 min; m/z 543.2 (M+H).

Example 17 (WITJ0529B)

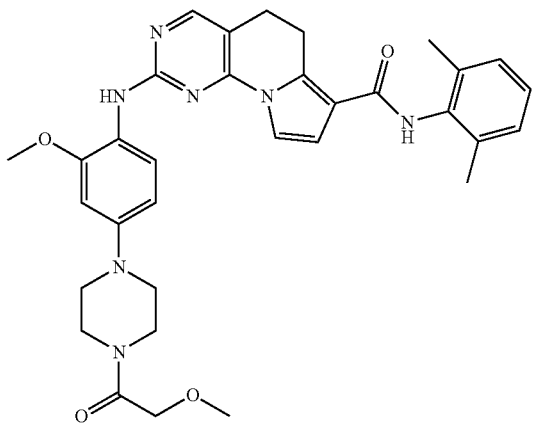 [SMILES: COCC(=O)N1CCN(c2ccc(Nc3ncc4c(n3)-n3ccc(C(=O)Nc5c(C)cccc5C)c3CC4)c(OC)c2)CC1]

N-(2,6-dimethylphenyl)-2-[2-methoxy-4-[4-(2-methoxyacetyl)piperazin-1-yl]anilino]-5,6-dihydropyrimido[4,5-e]indolizine-7-carboxamide This compound was prepared from its corresponding amine (prepared as described for Example 7 starting from Intermediate 1 and Intermediate M) and methoxyacetic acid, using standard HATU-coupling procedures as described in Example 8d. Purification was performed using preparative HPLC to afford the title compound (10 mg, 49%). Data: LCMS (B) $R_t$: 12.973 min; m/z 596.3 (M+H)+.

Intermediate 3

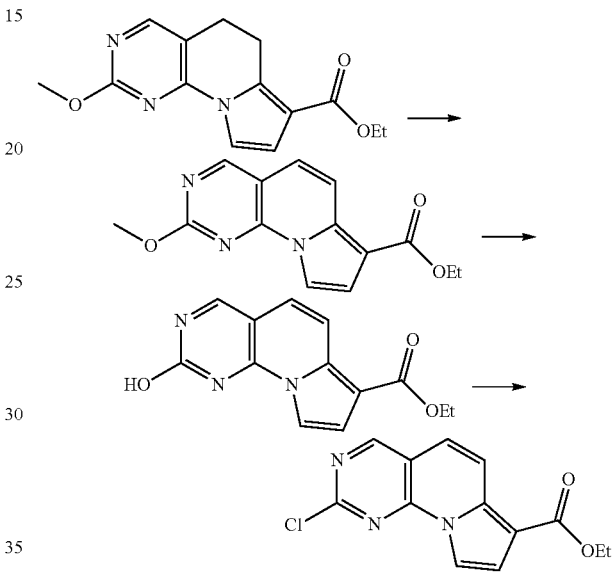

Ethyl 2-chloropyrimido[4,5-e]indolizine-7-carboxylate (a) Ethyl 2-methoxypyrimido[4,5-e]indolizine-7-carboxylate (JGS362)

DDQ (1.53 g, 6.76 mmol) was added to a stirred solution of ethyl 2-methoxy-5,6-dihydropyrimido[4,5-e]indolizine-7-carboxylate (1.54 g, 5.63 mmol) in DCM (50 mL). The reaction mixture stirred for 3 days at room temperature. An additional amount of 200 mg DDQ was added and the reaction mixture was stirred for another 7 days at room temperature. The mixture was filtered and concentrated in vacuo to a small volume. The crude product was purified by column chromatography on silica (heptane/ethyl acetate=I/O to 1/1 v/v %) to yield the title compound (750 mg, 50%).

(b) Ethyl 2-hydroxypyrimido[4,5-e]indolizine-7-carboxylate (JGS377)

Sodium iodide (1.24 g, 8.29 mmol) was added to a stirred solution of ethyl 2-methoxy-pyrimido[4,5-e]indolizine-7-carboxylate (750 mg, 2.76 mmol) in acetonitrile (19 mL). A solution of trimethylsilyl chloride (896 mg, 1.05 mL) in acetonitrile (3 mL) was added drop-wise to the reaction mixture. The mixture was stirred at room temperature o/n. Additional sodium iodide (3.33 g) TMS-Cl (2.4 g, 2.8 mL) in acetonitrile (6 mL) were added drop-wise and the reaction was stirred for 3 days at room temperature. The mixture was concentrated under reduced pressure. The residue was suspended in 200 mL DCM/MeOH (4/1) and extracted with a mixture of a saturated solution of sodium thiosulfate (50 mL) and water (100 mL). The water layer was extracted with DCM/MeOH (4/1, 2×150 mL). The combined organic layers were dried over sodium sulfate, filtered and the solvent was removed under reduced pressure to give a solid. The solid was triturated in boiling ethyl acetate (50 mL). After cooling the solid was stirred 1h at room temperature and filtered. The residue was dried at 40° C. under vacuum to give 1.0 g crude ethyl 2-hydroxy-5,6-dihydropyrimido[4,5-e]indolizine-7-carboxylate (quant. yield).

(c) Ethyl 2-chloropyrimido[4,5-e]indolizine-7-carboxylate (Intermediate 3) (JGS380)

N,N-Dimethylaniline (47 mg, 50 µL, 1.50 mmol) was added to a solution of ethyl 2-hydroxypyrimido[4,5-e]indolizine-7-carboxylate (1.0 g, 3.89 mmol) in acetonitrile (30 mL). A solution of phosphorous(V) oxychloride (2.99 g, 1.81 mL, 19.5 mmol) in acetonitrile (4 mL) was added drop-wise to the reaction mixture. The brown/red suspension was heated to 65° C. for 4 hours. After cooling, the mixture was slowly poured in a stirred mixture of 25% aq. ammonia (50 mL) and ice-water (100 mL) keeping the temperature below 10° C. After stirring for another 15 minutes the mixture was extracted with ethyl acetate. The combined organic layers were subsequently washed with water (50 mL), 0.2 N HCl (50 mL), brine (25 mL), dried (Na₂SO₄), filtered and concentrated in vacuo. The crude product was purified by column chromatography on silica (heptane/ethyl acetate=1/0 to 1/1 v/v %) to yield 200 mg of the title compound.

Example 18 (WITJ490B)

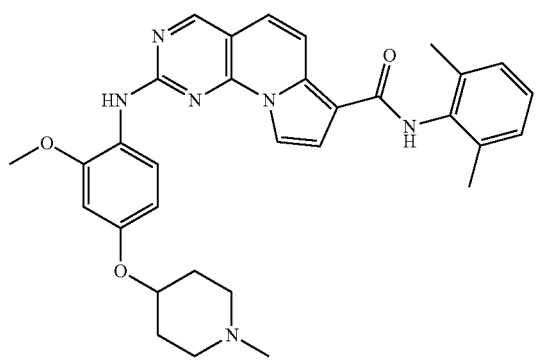 [SMILES: COc1cc(OC2CCN(C)CC2)ccc1Nc1ncc2ccc3c(C(=O)Nc4c(C)cccc4C)ccn3c2n1]

N-(2,6-dimethylphenyl)-2-[2-methoxy-4-[(1-methyl-4-piperidyloxy]anilino]pyrimido[4,5-e]indolizine-7-carboxamide This compound was prepared from its corresponding acid chloride, using the same sequence of reactions as described for Intermediate 2, starting from Intermediate 3 and Intermediate K as starting material. The acid chloride was subsequently reacted with 2,6-dimethylaniline according to procedures described in Example 7. Purification was performed using preparative HPLC to afford the title compound (30 mg, 45%). Data: LCMS (B) $R_t$: 12.491 min; m/z 551.3 (M+H)⁺.

Intermediate N (JDM618/JDM626/JDM634)

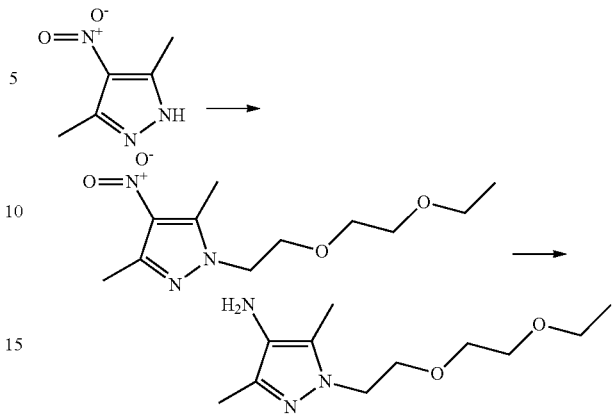

1-[2-(2-Ethoxyethoxy)ethyl]-3,5-diethyl-pyrazol-4-amine

(a) 2-(2-Ethoxyethoxy)ethyl 4-methylbenzenesulfonate

To a solution of di(ethylene glycol)ethyl ether (4.92 ml, 36.2 mmol) in 15 mL of THF, cooled at 0° C., was added NaOH (2.46 g. 61.5 mmol) dissolved in 15 mL of water with vigorous stirring. To this mixture was added dropwise a solution of tosyl chloride (8.28 g. 43.4 mmol) in 15 mL of THF over 10 min at 0° C. The reaction mixture was then raised to rt and stirred for 1 h under nitrogen. The mixture was then extracted twice with 50 mL of diethyl ether, and the organic layer was washed with 1 M aq NaOH and water and dried over sodium sulfate. Solvent was removed under reduced pressure to yield 2-(2-ethoxyethoxy)ethyl 4-methylbenzenesulfonate as a colorless liquid (10 g. 95.8%).

(b) 1-[2-(2-Ethoxyethoxyl)ethyl]-3,5-dimethyl-4-nitro-pyrazole

To a solution of 3,5-dimethyl-4-nitro-1H-pyrazol (1 g. 7.08 mmol) and cesium carbonate (2.31 g. 7.08 mmol) in DMF (10 mL) was added 2-(2-ethoxyethoxy)ethyl 4-methylbenzenesulfonate (2.04 g. 7.08 mmol). The mixture was heated at 100° C. for 1 h. After cooling to room temperature, the mixture was poured into water/brine and extracted with ethyl acetate (100 mL). The combined organic layer was washed with brine, dried over sodium sulfate, filtered and concentrated under reduced pressure to yield 1.69 g of the title compound (92.8%).

(c) 1-[2-(2-Ethoxyethoxy)ethyl]-3,5-dimethyl-pyrazol-4-amine (Intermediate N)

To a stirred solution of 1-[2-(2-ethoxyethoxy)ethyl]-3,5-dimethyl-4-nitro-pyrazole (1.69 g, 6.57 mmol) in methanol (25 mL) was added a suspension of 10% Pd on charcoal (200 mg) in ethanol (1 mL). The reaction mixture was stirred at room temperature for 15 min under a nitrogen atmosphere. Then, ammonium formate (4.14 g, 65.7 mmol) was added and the reaction mixture was heated to reflux temperature for 15 min. The reaction mixture was cooled, filtered over Decalite® and concentrated in vacuo. The residue was dissolved in methanol and then filtered over an SCX-2 column. After rinsing the column with methanol, the desired product was eluted with an 0.7N ammonia/methanol solution. The resulting eluate was concentrated in vacuo to give the title compound (520 mg, 34.8%).

Example 19 (JDM640A)

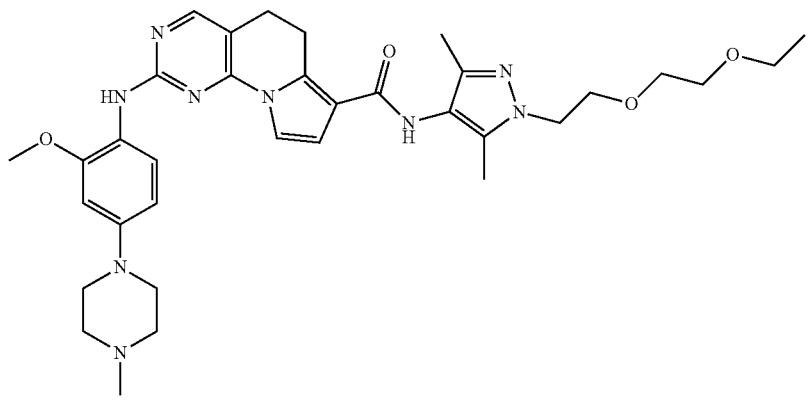 [SMILES: CCOCCOCCn1nc(C)c(NC(=O)c2ccn3c2CCc2cnc(Nc4ccc(N5CCN(C)CC5)cc4OC)nc2-3)c1C]

N-[1-[2-(2-ethoxyethoxy)ethyl]-3,5-dimethyl-pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid, using the same sequence of reactions, as described for Intermediate 2b, using Intermediate D as starting material. The carboxylic acid was subsequently reacted with Intermediate N in an analogous manner as described for Example 8d. Purification was performed using preparative HPLC to afford the title compound (32.3 mg, 53.9%). Data: LCMS (B) $R_t$: 7.432 min; m/z 644.6 (M+H)$^+$.

Example 20 (JDM677A)

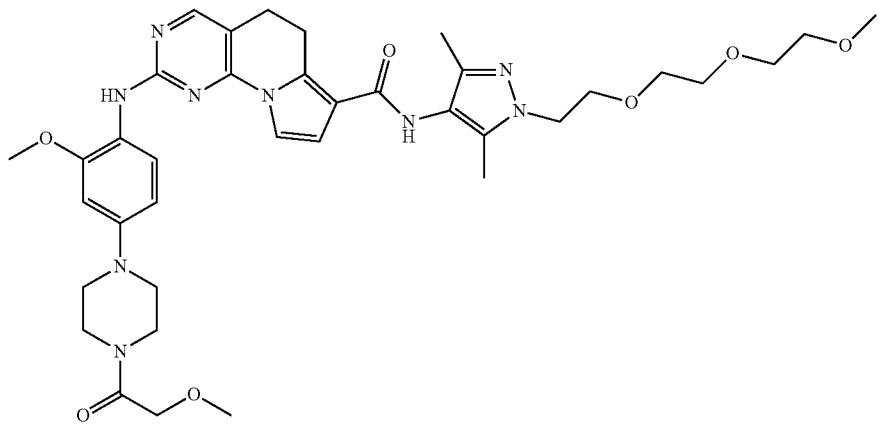

N-[1-[2-[2-(2-methoxyethoxy)ethoxyethyl]-3,5-dimethyl]-pyrazol-4-yl]-2-[2-methoxy-4-[4-(2-methoxyacetyl)piperazin-1-yl]anilino]-5,6-dihydropyrimido[4,5-e]indolizine-7-carboxamide This compound was prepared from its corresponding acid, using the same sequence of reactions, as described for Intermediate 2b, using Intermediate M as starting material. The carboxylic acid was subsequently reacted with Intermediate C in an analogous manner as described for Example 8d. The corresponding amine was obtained after deprotection of the Cbz-group and methoxyacetic acid was introduced, using standard HATU-coupling procedures as described in Example 8d. Purification was performed using preparative HPLC to afford the title compound (19.0 mg, 63.4%). Data: LCMS (B) $R_t$: 8.815 min; m/z 732.7 (M+H)$^+$.

Example 21 (JDM711A)

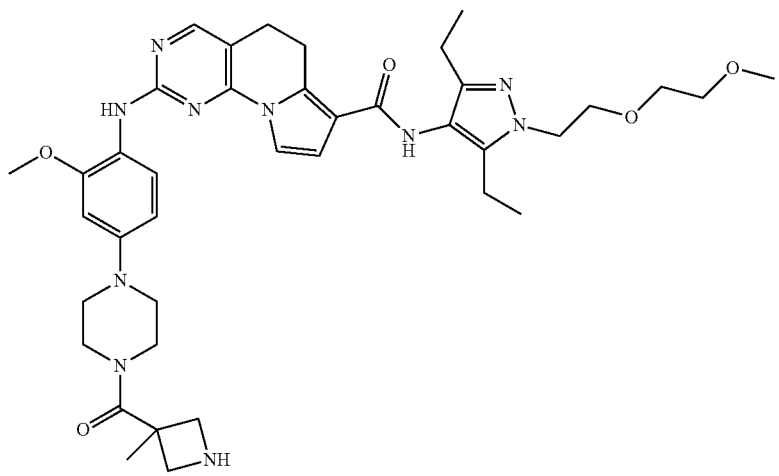

N-[3,5-diethyl-1-[2-(2-methoxyethoxy ethyl]pyrazol-4-yl]-2-[2-methoxy-4-[4-(3-methylazetidine-3-carbonyl)piperazin-1-yl]anilino]-5,6-dihydropyrimido[4,5-e]indolizine-7-carboxamide This compound was prepared from its corresponding acid, using the same sequence of reactions, as described for Intermediate 2b, using Intermediate M as starting material. The carboxylic acid was subsequently reacted with Intermediate I in an analogous manner as described for Example 8d. The corresponding amine was obtained after deprotection of the Cbz-group and 1-(tert-butoxycarbonyl)-3-methylazetidine-3-carboxylic acid was introduced, using standard HATU-coupling procedures as described in Example 8d. Purification was performed, after deprotection of the Boc-group, using preparative HPLC to afford the title compound (16.3 mg, 55%). Data: LCMS (B) R$_t$: 8.107 min; m/z 741.8 (M+H)$^+$.

Intermediate O (JDM618/JDM625/JDM633)

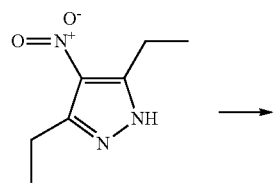

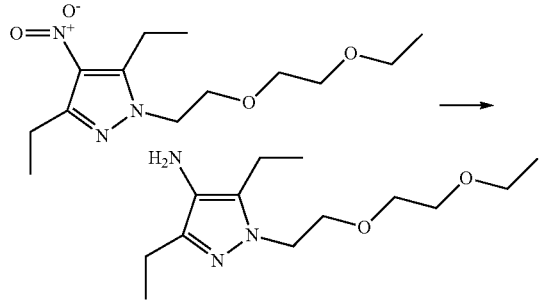

1-[2-(2-Ethoxyethoxy)ethyl]-3,5-diethyl-pyrazol-4-amine

The title compound was prepared in an analogous manner as described for Intermediate N, starting from 3,5-diethyl-4-nitro-1H-pyrazole (Intermediate Fb) and di(ethylene glycol)ethyl ether to give 550 mg of 1-[2-(2-ethoxyethoxy)ethyl]-3,5-diethyl-pyrazol-4-amine (79.8%.).

Example 22 (JDM713A)

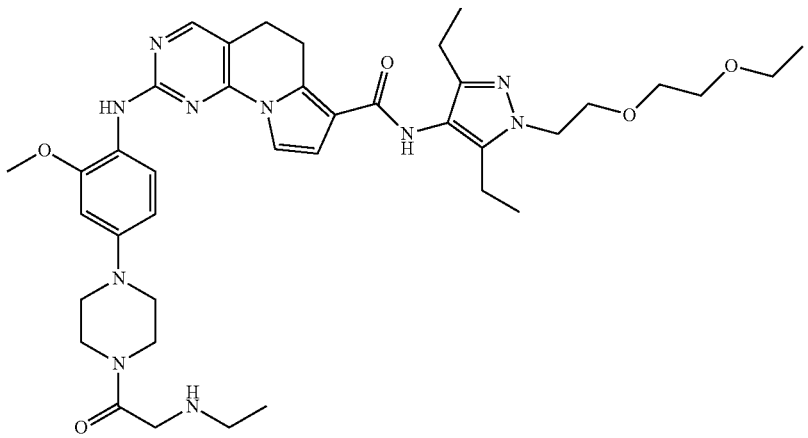 [SMILES: CCNCC(=O)N1CCN(c2ccc(Nc3ncc4c(n3)-n3ccc(C(=O)Nc5c(CC)nn(CCOCCOCC)c5CC)c3CC4)c(OC)c2)CC1]

N-[3,5-diethyl-1-[2-(2-methoxyethoxy)ethyl]pyrazol-4-yl]-2-[2-methoxy-4-[4-(3-methylazetidine-3-carbonyl)piperazin-1-yl]anilino]-5,6-dihydropyrimido[4,5-e]indolizine-7-carboxamide This compound was prepared from its corresponding acid, using the same sequence of reactions, as described for Intermediate 2b, using Intermediate M as starting material. The carboxylic acid was subsequently reacted with Intermediate O in an analogous manner as described for Example 8d. The corresponding amine was obtained after deprotection of the Cbz-group and Boc-N-ethyl-glycine was introduced, using standard HATU-coupling procedures as described in Example 8d. Purification was performed, after deprotection of the Boc-group, using preparative HPLC to afford the title compound (15 mg, 53.1%). Data: LCMS (B) $R_t$: 8.619 min; m/z 743.8 (M+H)$^+$.

Example 23 (JDM697A)

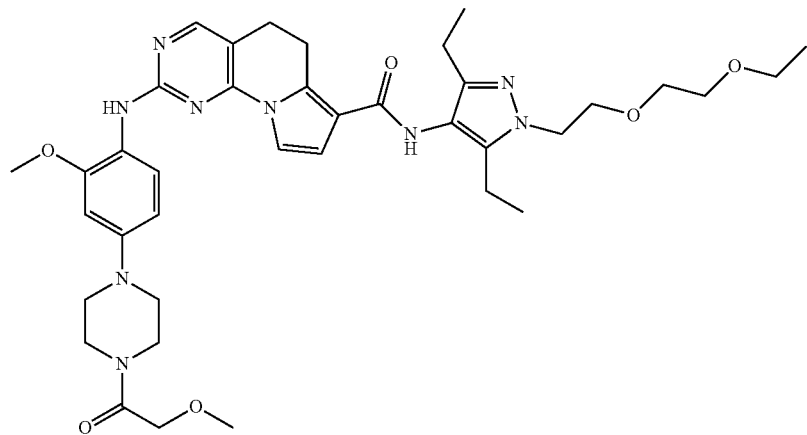 [SMILES: CCOCCOCCn1nc(CC)c(NC(=O)c2ccn3c2CCc2cnc(Nc4ccc(N5CCN(C(=O)COC)CC5)cc4OC)nc2-3)c1CC]

N-[1-[2-(2-ethoxyethoxy)ethyl]-3,5-diethyl-pyrazol-4-yl]-2-[2-methoxy-4-[4-(2-methoxyacetyl)piperazin-1-yl]anilino]-5,6-dihydropyrimido[45-e]indolizine-7-carboxamide This compound was prepared from its corresponding acid, using the same sequence of reactions, as described for Intermediate 2b, using Intermediate M as starting material. The carboxylic acid was subsequently reacted with Intermediate O in an analogous manner as described for Example 8d. The corresponding amine was obtained after deprotection of the Cbz-group and methoxyacetic acid was introduced, using standard HATU-coupling procedures as described in Example 8d. Purification was performed using preparative HPLC to afford the title compound (17.0 mg, 61.4%). Data: LCMS (B) $R_t$:10.554 min; m/z 730.7 (M+H)$^+$.

Example 24 (JDM636A)

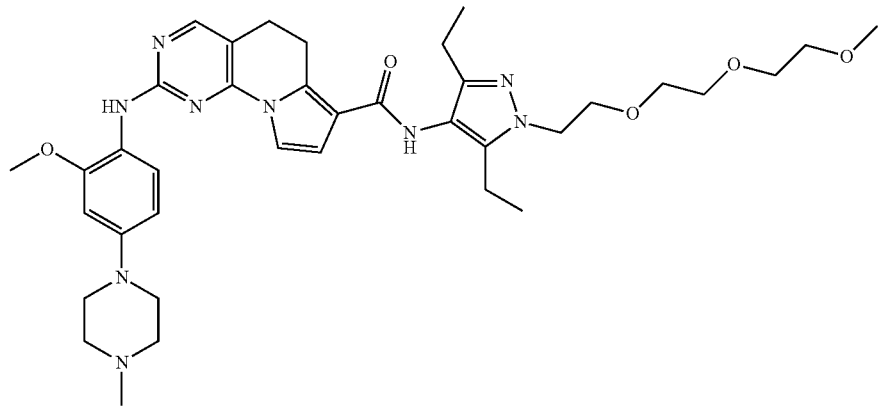

N-[3,5-diethyl-1-[2-[2-(2-methoxyethoxy) ethoxy] ethyl]pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid, using the same sequence of reactions, as described for Intermediate 2b, using Intermediate D as starting material. The carboxylic acid was subsequently reacted with Intermediate G in an analogous manner as described for Example 8d. Purification was performed using preparative HPLC to afford the title compound (22.5 mg, 34.5%). Data: LCMS (B) $R_t$: 7.879 min; m/z 702.7 (M+H).

Example 25 (JDM703A)

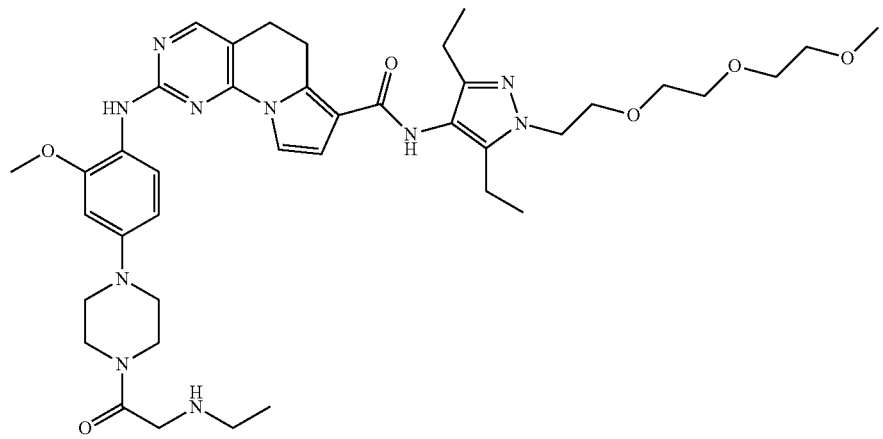

N-[3,5-diethyl-1-[2-[2-(2-methoxyethoxy)ethoxy]ethyl]pyrazol-4-yl]-2-[4-[4-[2-(ethylamino)acetyl]piperazin-1-yl]-2-methoxy-anilino]-5,6-dihydropyrimido[4,5-e]indolizine-7-carboxamide This compound was prepared from its corresponding acid, using the same sequence of reactions, as described for Intermediate 2b, using Intermediate M as starting material. The carboxylic acid was subsequently reacted with Intermediate G in an analogous manner as described for Example 8d. The corresponding amine was obtained after deprotection of the Cbz-group and Boc-N-ethyl-glycine was introduced, using standard HATU-coupling procedures as described in Example 8d. Purification was performed, after deprotection of the Boc-group, using preparative HPLC to afford the title compound (18.4 mg, 59.4%). Data: LCMS (B) $R_t$: 8.194 min; m/z 773.8 (M+H)$^+$.

Example 26 (JDM709A)

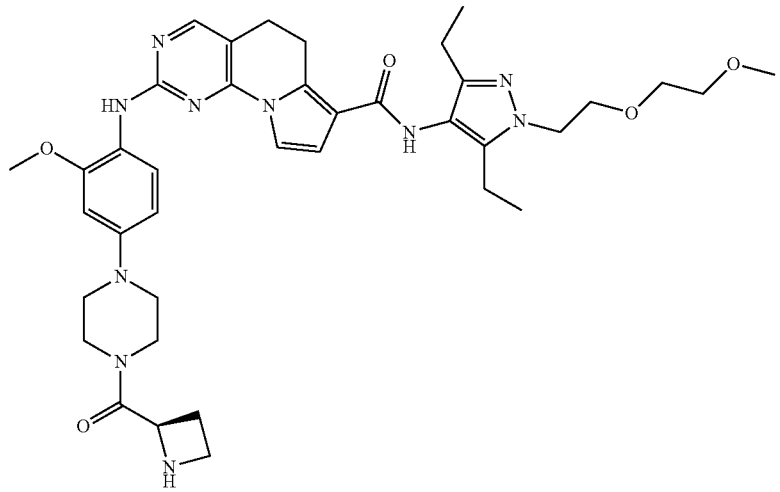

2-[4-[4-[(2R)-azetidine-2-carbonyl]piperazin-1-yl]-2-methoxy-anilino]-N-[3,5-diethyl-1-[2-(2-methoxy-ethoxy)ethyl]pyrazol-4-yl]-5,6-dihydropyrimido[4,5-e]indolizine-7-carboxamide This compound was prepared from its corresponding acid, using the same sequence of reactions, as described for Intermediate 2b, using Intermediate M as starting material. The carboxylic acid was subsequently reacted with Intermediate I in an analogous manner as described for Example 8d. The corresponding amine was obtained after deprotection of the Cbz-group and (R)—N-Boc-azetidine-2-carboxylic acid was introduced, using standard HATU-coupling procedures as described in Example 8d. Purification was performed, after deprotection of the Boc-group, using preparative HPLC to afford the title compound (16.8 mg, 57.7%). Data: LCMS (B) $R_t$: 8.017 min; m/z 727.9 (M+H)$^+$.

Example 27 (JDM666A)

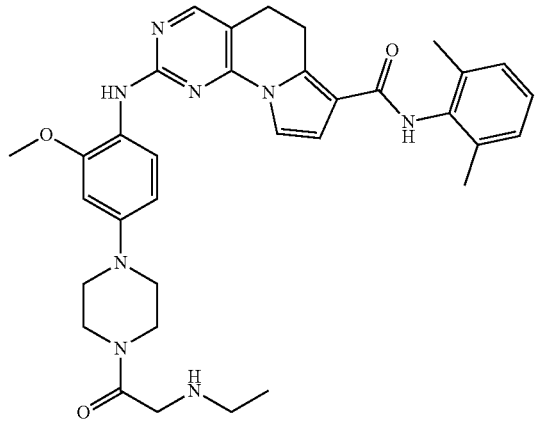 [SMILES: CCNCC(=O)N1CCN(c2ccc(Nc3ncc4c(n3)-n3ccc(C(=O)Nc5c(C)cccc5C)c3CC4)c(OC)c2)CC1]

N-(2,6-dimethylphenyl-2-[4-[4-[2-ethylamino)acetyl]piperazin-1-yl]-2-methoxy-anilino]-5,6-dihydropyrimido[4,5-e]indolizine-7-carboxamide This compound was prepared from its corresponding acid chloride, using the same sequence of reactions, as described for Intermediate 2, using Intermediate M as starting material. The acid chloride was subsequently reacted with 2,6-dimethylaniline in an analogous manner as described for Example 7. The corresponding amine was obtained after deprotection of the Cbz-group and Boc-N-ethyl-glycine was introduced, using standard HATU-coupling procedures as described in Example 8d. Purification was performed, after deprotection of the Boc-group, using preparative HPLC to afford the title compound (1 mg, 13.2%). Data: LCMS (B) $R_t$: 9.388 min; m/z 609.6 (M+H)$^+$.

Example 28 (JGS0715B)

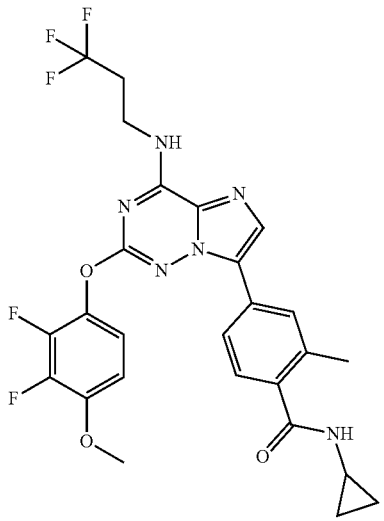 [SMILES: COc1ccc(Oc2nc(NCCC(F)(F)F)c3ncc(-c4ccc(C(=O)NC5CC5)c(C)c4)n3n2)c(F)c1F]

N-cyclopropyl-4-[6-(2,3-difluoro-4-methoxy-phenoxy)-8-(3,3,3-trifluoropropylamino)imidazo[1,2-b]pyridazin-3-yl]-2-methyl-benzamide This compound was prepared as described in WO 2014/131739 A1. Purification was performed using preparative HPLC to afford the title compound (30 mg). Data: LCMS (B) $R_t$: 14.958 min; m/z 562.5 (M+H)$^+$.

Example 29 (JDM943D)

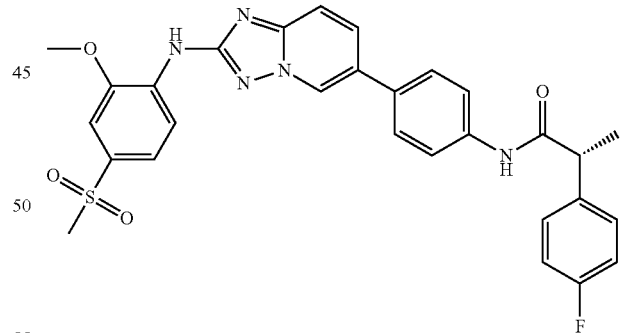

(2R)-2-(4-fluorphenyl)-N-[4-[2-(2-methoxy-4-methylsulfonyl-anilino)-[1,2,4]triazolo-[1,5-a]pyridin-6-yl]phenyl]propanamide This compound was prepared as described in WO 2014/009219 A1. Purification was performed using preparative HPLC to afford the title compound (107.1 mg). Data: LCMS (B) $R_t$: 13.703 min; m/z 558.0 (M–H)$^-$.

Example 30 (JDM969A)

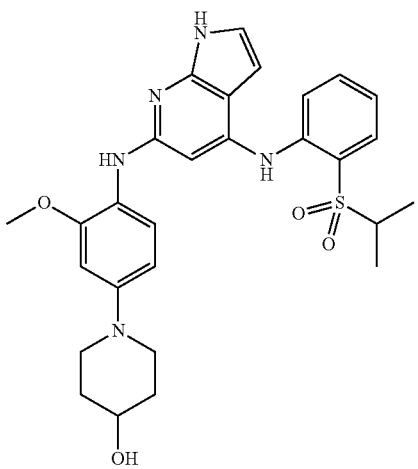 [SMILES: COc1cc(N2CCC(O)CC2)ccc1Nc1cc(Nc2ccccc2S(=O)(=O)C(C)C)c2cc[nH]c2n1]

1-[4-[[4-(2-Isopropylsulfonylanilino)-1H-pyrrolo[2,3-b]pyridin-6-yl]amino]-3-methoxy-phenyl]piperidin-4-ol (Mps1-IN-1)

This compound was purchased from Tocris.

Example 31 (JDM969B)

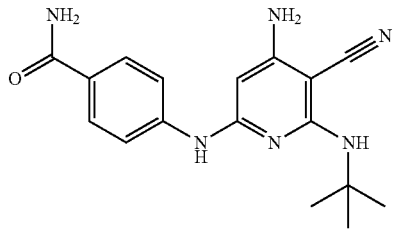 [SMILES: CC(C)(C)Nc1nc(Nc2ccc(C(N)=O)cc2)cc(N)c1C#N]

4-[[4-Amino-6-(tert-butylamino)-5-cyano-2-pyridyl]amino]benzamide (TC Mps1 12)

This compound was purchased from Tocris.

TTK Enzyme Assay

The inhibitory activity of compounds on biochemically purified full-length TTK (Life Technologies, Madison, Wis., U.S.A.) was determined in the IMAP® assay (Molecular Devices, Sunnyvale, Calif., U.S.A.). Compounds were dissolved in 100% dimethylsulfoxide (DMSO). At the day of the experiment, the compound stock was diluted in 3.16 fold steps in 100% DMSO, to obtain a 10-point dilution series, followed by further dilution in IMAP reaction buffer, which consists of 10 mM Tris-HCl, pH 7.5, 10 mM $MgCl_2$, 0.01% Tween-20, 0.1% $NaN_3$ and 1 mM freshly prepared dithiothreitol. Compound solution was mixed with an equal volume of full-length TTK enzyme in IMAP reaction buffer. After pre-incubation of 1 hour in the dark at room temperature, fluorescein-labeled MBP-derived substrate peptide (Molecular Devices) was added and ATP to start the reaction. Final enzyme concentration was 3.9 nM, final substrate concentration 50 nM, and final ATP concentration was 5 µM. The reaction was allowed to proceed for 2 hours at room temperature in the dark. The reaction was stopped by quenching with IMAP progressive binding solution according to the protocol of the manufacturer (Molecular Devices). Fluorescein polarization was measured on an Envision multimode reader (Perkin Elmer, Waltham, Mass., USA). Dose-response curves were fitted to a four-parameter logarithmic equation in XLfit™ 5 (ID Business Solutions, Ltd., Guildford, U.K.). Table 3 show the half-maximum inhibitory potency of a number of TTK inhibitors from different chemical classes in an enzyme assay for TTK.

TABLE 3

Activity of small molecule TTK inhibitors in TTK enzyme assay.

| Example nr. | $IC_{50}$ (nM) |
| --- | --- |
| Example 1 | 2.6 |
| Example 2 | 4.1 |
| Example 3 | 0.63 |
| Example 4 | 0.49 |
| Example 5 | 0.65 |
| Example 6 | 0.6 |
| Example 7 | 0.7 |
| Example 8 | 0.6 |
| Example 9 | 0.73 |
| Example 10 | 0.93 |
| Example 11 | 0.6 |
| Example 12 | 0.97 |
| Example 13 | 0.43 |
| Example 14 | 0.98 |
| Example 15 | 1.1 |
| Example 16 | 1.0 |
| Example 17 | 1.0 |
| Example 18 | 1.4 |
| Example 19 | 1.14 |
| Example 20 | 0.62 |
| Example 21 | 0.96 |
| Example 22 | 0.71 |
| Example 23 | 0.41 |
| Example 24 | 0.91 |
| Example 25 | 0.43 |
| Example 26 | 0.66 |
| Example 27 | 0.41 |
| Example 28 | 0.79 |
| Example 29 | 2.55 |
| Example 30 | 37.5 |
| Example 31 | 7.0 |

In order to identify genomic biomarkers that correlate with the sensitivity of cancer cells to the TTK inhibitors, the compounds were tested in proliferation assays with sixty-six different, genetically well-characterized cancer cell lines.

Statistical analysis of the anti-proliferative activity of the inhibitors with the presence of specific cancer gene mutations in the cell lines revealed that TTK inhibitors preferentially kill cells that harbor mutation in the CTNNB1 gene known to be involved in regulation of the stability of the CTNNB1-encoded protein β-catenin.

FIGS. 2A-2G show the volcano plot of the Anova analysis of Examples 5, 8, 9, 12, 13 and 17. To verify if a TTK inhibitor was significantly more potent in cell lines expressing mutant CTNNB1 in comparison to cell lines not harboring mutation in CTNNB1, a one-sided Student's t-test was carried out. Table 4 shows the difference in sensitivity ($\Delta pIC_{50}$) of a number of representative TTK inhibitors from different chemical classes. A negative $\Delta pIC_{50}$ value indicates that CTNNB1 mutant cell lines are more sensitive to the inhibitor than cell lines not harboring mutations in the regulatory domain of the CTNNB1 gene (Table 2). A p value <0.05 indicates that the difference is significant.

TABLE 4

Difference in sensitivity of CTNNB1-mutant and non-mutant cell lines for TTK inhibitors

| | pIC50 average[1] | | | significance |
|---|---|---|---|---|
| Example nr. | Wild type[3] | Mutant[3] | Δ pIC50 | p-value[2] |
| Example 1 | 6.15 | 6.78 | −0.63 | 5.0E−03 |
| Example 2 | 5.73 | 5.98 | −0.25 | 3.6E−02 |
| Example 3 | 5.68 | 6.01 | −0.33 | 2.4E−02 |
| Example 4 | 7.21 | 7.64 | −0.43 | 3.3E−02 |
| Example 5 | 7.06 | 7.60 | −0.54 | 1.2E−02 |
| Example 6 | 6.93 | 7.64 | −0.71 | 8.8E−03 |
| Example 7 | 7.47 | 7.92 | −0.45 | 2.6E−02 |
| Example 8 | 7.38 | 7.96 | −0.57 | 1.3E−02 |
| Example 9 | 7.50 | 8.18 | −0.68 | 1.9E−02 |
| Example 10 | 6.86 | 7.41 | −0.55 | 1.4E−02 |
| Example 11 | 6.99 | 7.48 | −0.49 | 2.7E−02 |
| Example 12 | 6.96 | 7.65 | −0.69 | 6.5E−03 |
| Example 13 | 7.82 | 8.60 | −0.79 | 7.1E−03 |
| Example 14 | 7.47 | 8.01 | −0.54 | 1.8E−02 |
| Example 15 | 6.60 | 7.28 | −0.69 | 3.9E−03 |
| Example 16 | 6.46 | 7.22 | −0.76 | 4.6E−03 |
| Example 17 | 7.72 | 8.33 | −0.61 | 1.7E−02 |
| Example 18 | 7.53 | 8.13 | −0.60 | 2.9E−02 |
| Example 19 | 7.20 | 7.72 | −0.53 | 9.3E−03 |
| Example 20 | 7.28 | 7.90 | −0.2 | 8.7E−03 |
| Example 21 | 7.19 | 7.98 | −0.79 | 1.2E−02 |
| Example 22 | 7.70 | 8.34 | −0.65 | 9.1E−03 |
| Example 23 | 7.97 | 8.55 | −0.59 | 2.0E−02 |
| Example 24 | 7.59 | 8.09 | −0.50 | 2.5E−02 |
| Example 25 | 7.62 | 8.37 | −0.75 | 3.2E−03 |
| Example 26 | 7.28 | 7.96 | −0.68 | 9.9E−03 |
| Example 27 | 7.60 | 8.17 | −0.57 | 1.9E−02 |
| Example 28 | 7.00 | 7.47 | −0.47 | 1.1E−02 |
| Example 29 | 6.40 | 6.72 | −0.31 | 1.8E−02 |
| Example 30 | 5.17 | 5.39 | −0.23 | 1.0E−01 |
| Example 31 | 6.02 | 6.36 | −0.34 | 2.8E−02 |

[1] defined as $-^{10}\log IC_{50}$ (in M)
[2] one-side student T-test, heteroscedastic
[3] referring to CTNNB1 gene In order to verify that the presence of a mutated CTNNB1 gene copy is sufficient to confer increased sensitivity to TTK inhibitors, proliferation assays were carried out with parental HCT116 cells (S45del/+) and an isogenic derivative lacking mutated CTNNB (−/+). Table 5 summarizes the difference in sensitivity of a number of representative TTK inhibitors from different chemical classes in the isogenic cell line in comparison to parental HCT116 cells. A negative $\Delta pIC_{50}$ or a negative Δefficacy indicates that HCT116 parental cells, expressing mutant CTNNB1 (S45del/+) are more sensitive to the inhibitor than the isogenic derivative, in which the mutated CTNNB1 gene has been removed (−/+). Thus, inhibitors with a negative ΔpIC50 or a negative Δefficacy better inhibit the cell line where mutant CTNNB1 signaling is present.

TABLE 5

Difference in sensitivity for TTK inhibitors in HCT116 cells expressing either a mutated copy of the CTNNB1 gene or not.

| | $\Delta pIC_{50}$ | Δefficacy |
|---|---|---|
| Example 5 | −0.17 | −26 |
| Example 8 | −0.29 | −11 |
| Example 12 | −0.14 | −18 |
| Example 13 | −0.01 | −27 |
| Example 17 | −0.12 | −16 |
| Example 20 | −0.20 | −34 |

The invention claimed is:

1. A method for treating a tumor in a human individual or an animal that is susceptible to treatment with a TTK inhibitor, the method comprising:

determining that the tumor is susceptible to treatment with the TTK inhibitor when the presence of a mutated CTNNB1 gene having a mutation located in exon 3 has been detected in a tumor sample from the human individual or animal; and treating, with the TTK inhibitor, the human individual or animal whose tumor is determined to be susceptible to treatment with the TTK inhibitor, wherein the TTK inhibitor is a chemical compound belonging to the class of compounds according to Formula I:

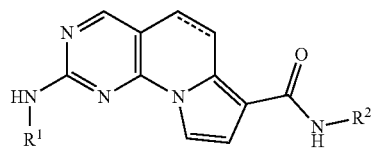

Formula I wherein:

$R^1$ is selected from the group consisting of:

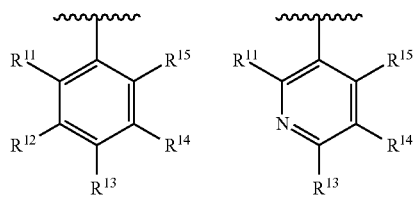

-continued

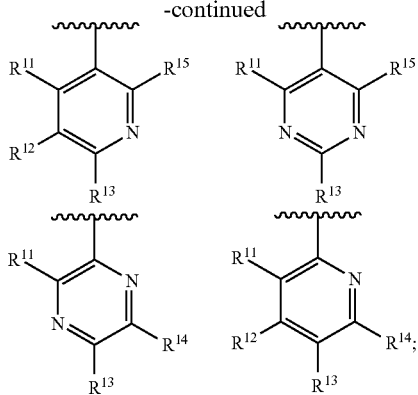

$R^{11}$ is H, halogen, (1-2C)alkyl, (2-3C)alkenyl, (2-3C)alkynyl, (1-2C)alkoxy or $OC_2H_3$, all alkyl and alkoxy groups optionally being substituted with one or more halogen;

$R^{12}$ is H, halogen, (1-2C)alkyl or (1-2C)alkoxy;

$R^{13}$ is $R^{131}CH_2$, $R^{132}O$, $R^{133}R^{134}N$, $R^{135}C(O)$, $R^{136}S$, $R^{136}S(O)$, $R^{136}S(O)(NH)$, $R^{137}SO_2$, (2-7C)heterocycloalkyl, or (1-5C)heteroaryl each heterocycloalkyl or heteroaryl optionally being substituted with (1-2C)alkyl, fluoro, hydroxyl, oxo, (1-2C)alkoxy, (1-6C)alkylcarbonyl, (1-6C)alkylsulfonyl, (1-5C)alkoxycarbonyl, (1-6C)alkylaminocarbonyl, (3-6C)cycloalkylcarbonyl, (2-7C)heterocycloalkylcarbonyl or di[(1-2C)alkyl]amino, each alkylcarbonyl, alkylsulfonyl, alkoxycarbonyl, alkylaminocarbonyl, cycloalkylcarbonyl or heterocycloalkylcarbonyl optionally being substituted with (1-2C)alkyl, fluoro, hydroxyl, cyano, oxo or (1-2C)alkoxy;

$R^{131}$ is (1-6C)alkylcarbonylamino, (3-6C)cycloalkylcarbonylamino or (2-7C)heterocycloalkylcarbonylamino each optionally substituted with one or more groups selected from (1-2C)alkyl, fluoro, hydroxyl or (1-2C)alkoxy;

$R^{132}$ is (1-6C)alkyl, (3-6C)cycloalkyl, (2-7C)heterocycloalkyl, (6-10C)aryl or (1-5C)heteroraryl each optionally substituted with one or more groups selected from (1-2C)alkyl, halogen, hydroxyl, (1-2C)alkoxy, di[(1-2C)alkyl]amino or (2-7C)heterocycloalkyl;

$R^{133}$ is (1-6C)alkyl, (3-6C)cycloalkyl, (2-7C)heterocycloalkyl (1-6C)alkylcarbonyl, (1-5C)alkoxycarbonyl, (3-6C)cycloalkylcarbonyl or (2-7C)heterocycloalkylcarbonyl, each optionally substituted with one or more groups selected from (1-2C)alkyl, halogen, hydroxyl or (1-2C)alkoxy, di[(1-2C)alkyl]amino or (2-7C)heterocycloalkyl;

$R^{134}$ is hydrogen or (1-2C)alkyl;

$R^{135}$ is (2-7C)heterocycloalkyl, (1-6C)alkylamino, di[(1-6C)alkyl]amino, (2-7C)heterocycloalkylamino or (3-6C)cycloalkylamino each optionally substituted with one or more groups selected from (1-2C)alkyl, fluoro, hydroxyl, (1-2C)alkoxy, di[(1-2C)alkyl]amino, (2-7C)heterocycloalkyl, oxo, cyano or amino;

$R^{136}$ is (1-6C)alkyl, (3-6C)cycloalkyl, (2-7C)heterocycloalkyl each optionally substituted with one or more groups selected from (1-2C)alkyl, fluoro, hydroxyl or (1-2C)alkoxy;

$R^{137}$ is (1-6C)alkyl, (3-6C)cycloalkyl, (2-7C)heterocycloalkyl, (1-6C)alkylamino, di[(1-6C)alkyl]amino, (2-7C)heterocycloalkylamino or (3-6C)cycloalkylamino, each optionally substituted with one or more groups selected from (1-2C)alkyl, fluoro, hydroxyl or (1-2C)alkoxy;

$R^{14}$ is H, halogen, (1-2C)alkyl or (1-2C)alkoxy; and $R^{15}$ is H, halogen;

in the above Formula I, $R^2$ is selected from the group consisting of:

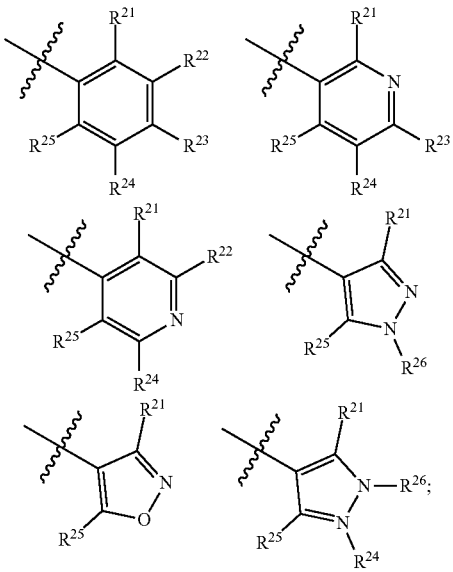

$R^{21}$ is H, halogen, (1-3C)alkyl, (1-2C)alkoxy, hydroxy(1-2C)alkyl, (3-4C)cycloalkyl, (2-3C)alkenyl or cyano;

$R^{22}$ is H, halogen, (1-2C)alkyl or (1-2C)alkoxy;

$R^{23}$ is H, halogen, (1-2C)alkyl, (1-2C)alkoxy, cyano or hydroxy;

$R^{24}$ is H, halogen, (1-2C)alkyl or (1-2C)alkoxy;

$R^{25}$ is H, halogen, (1-3C)alkyl, (1-2C)alkoxy, hydroxy(1-2C)alkyl, (3-4C)cycloalkyl, (2-3C)alkenyl or cyano;

$R^{26}$ is H, (1-6C)alkyl, (3-6C)cycloalkyl, (2-5C)heterocycloalkyl, (1-2C)alkoxy[(2-4C)alkoxy]$_n$(1-6C)alkyl, wherein n represents an integer of 1,2,3 or 4, all alkyl, heterocycloalkyl and (1-2C)alkoxy[(2-4C)alkoxy]$_n$, (1-6C)alkyl groups optionally substituted with one or more groups selected from (1-2C)alkyl, (1-2C)alkoxy, hydroxyl, oxo, amino, (3-6C)cycloalkyl, di[(1-2C)alkyl]amino or (2-5C)heterocycloalkyl; and wherein in the above Formula I only one of $R^{21}$ and $R^{25}$ in $R^2$ can be H.

2. The method according to claim 1, wherein the mutation is a missense mutation or a deletion of the serine residue corresponding to codon 33 of CTNNB1.

3. The method according to claim 1, wherein the mutation is a missense mutation or a deletion of the threonine residue corresponding to codon 41 of CTNNB1.

4. The method according to claim 1, wherein the mutation is a missense mutation or a deletion of the serine residue corresponding to codon 45 of CTNNB1.

5. The method according to claim 1, wherein the presence of the mutated CTNNB1 gene has been detected in tumor DNA in the tumor sample.

6. The method according to claim 1, wherein the presence of the mutated CTNNB1 gene has been detected in tumor mRNA in the tumor sample.

7. The method according to claim 1, wherein the presence of the mutated CTNNB1 gene has been detected by analyzing the amino acid sequence or phosphorylation of β-catenin in the tumor sample.

8. The method according to claim 1, wherein the tumor sample is taken from a tumor biopsy.

9. The method according to claim 1, wherein the tumor sample is taken from circulating tumor cells.

10. The method according to claim 5, wherein the tumor DNA is taken from a tumor biopsy.

11. The method according to claim 5, wherein the tumor DNA is derived from circulating tumor DNA.

12. A method for treating a tumor in a human individual or an animal, the method comprising:
    detecting whether a mutated CTNNB1 gene having a mutation located in exon 3 is present in a tumor sample from the human individual or animal;
    diagnosing the human individual or animal as being susceptible to treatment with a TTK inhibitor when the presence of the mutated CTNNB1 gene in the tumor sample is detected; and
    treating the diagnosed human individual or animal with the TTK inhibitor,
    wherein the TTK inhibitor is a chemical compound belonging to the class of compounds according to Formula I:

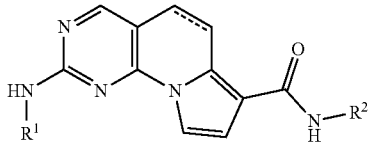

Formula I wherein:
$R^1$ is selected from the group consisting of:

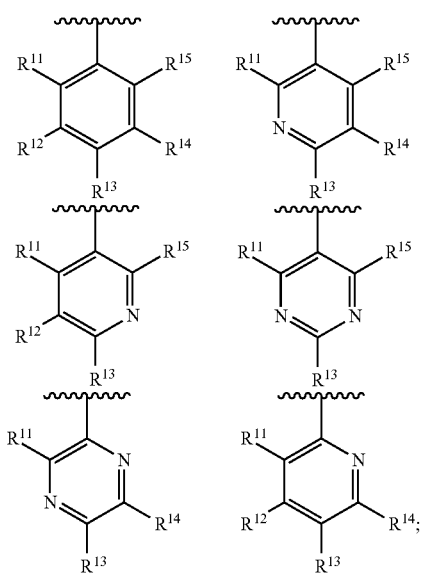

$R^{11}$ is H, halogen, (1-2C)alkyl, (2-3C)alkenyl, (2-3C) alkynyl, (1-2C)alkoxy or $OC_2H_3$, all alkyl and alkoxy groups optionally being substituted with one or more halogen;

$R^{12}$ is H, halogen, (1-2C)alkyl or (1-2C)alkoxy;

$R^{13}$ is $R^{131}CH_2$, $R^{132}O$, $R^{133}R^{134}N$, $R^{135}C(O)$, $R^{136}S$, $R^{136}S(O)$, $R^{136}S(O)(NH)$, $R^{137}SO_2$, (2-7C)heterocycloalkyl, or (1-5C)heteroaryl each heterocycloalkyl or heteroaryl optionally being substituted with (1-2C)alkyl, fluoro, hydroxyl, oxo, (1-2C)alkoxy, (1-6C)alkylcarbonyl, (1-6C)alkylsulfonyl, (1-5C) alkoxycarbonyl, (1-6C)alkylaminocarbonyl, (3-6C) cycloalkylcarbonyl, (2-7C)heterocycloalkylcarbonyl or di[(1-2C)alkyl]amino, each alkylcarbonyl, alkylsulfonyl, alkoxycarbonyl, alkylaminocarbonyl, cycloalkylcarbonyl or heterocycloalkylcarbonyl optionally being substituted with (1-2C)alkyl, fluoro, hydroxyl, cyano, oxo or (1-2C)alkoxy;

$R^{131}$ is (1-6C)alkylcarbonylamino, (3-6C)cycloalkylcarbonylamino or (2-7C)heterocycloalkylcarbonylamino each optionally substituted with one or more groups selected from (1-2C)alkyl, fluoro, hydroxyl or (1-2C) alkoxy;

$R^{132}$ is (1-6C)alkyl, (3-6C)cycloalkyl, (2-7C)heterocycloalkyl, (6-10C)aryl or (1-5C)heteroaryl each optionally substituted with one or more groups selected from (1-2C)alkyl, halogen, hydroxyl, (1-2C)alkoxy, di[(1-2C)alkyl]amino or (2-7C)heterocycloalkyl;

$R^{133}$ is (1-6C)alkyl,(3-6C)cycloalkyl, (2-7C)heterocycloalkyl (1-6C)alkylcarbonyl, (1-5C)alkoxycarbonyl, (3-6C)cycloalkylcarbonyl or (2-7C)heterocycloalkylcarbonyl, each optionally substituted with one or more groups selected from (1-2C)alkyl, halogen, hydroxyl or (1-2C)alkoxy, di[(1-2C)alkyl] amino or (2-7C)heterocycloalkyl;

$R^{134}$ is hydrogen or (1-2C)alkyl;

$R^{135}$ is (2-7C)heterocycloalkyl, (1-6C)alkylamino, di[(1-6C)alkyl]amino, (2-7C)heterocycloalkylamino or (3-6C)cycloalkylamino each optionally substituted with one or more groups selected from (1-2C) alkyl, fluoro, hydroxyl, (1-2C)alkoxy, di[(1-2C)alkyl]amino, (2-7C)heterocycloalkyl, oxo, cyano or amino;

$R^{136}$ is (1-6C)alkyl, (3-6C)cycloalkyl, (2-7C)heterocycloalkyl each optionally substituted with one or more groups selected from (1-2C)alkyl, fluoro, hydroxyl or (1-2C)alkoxy;

$R^{137}$ is (1-6C)alkyl, (3-6C)cycloalkyl, (2-7C)heterocycloalkyl, (1-6C)alkylamino, di[(1-6C)alkyl]amino, (2-7C)heterocycloalkylamino or (3-6C)cycloalkylamino, each optionally substituted with one or more groups selected from (1-2C)alkyl, fluoro, hydroxyl or (1-2C)alkoxy;

$R^{14}$ is H, halogen, (1-2C)alkyl or (1-2C)alkoxy; and $R^{15}$ is H, halogen;

in the above Formula I, $R^2$ is selected from the group consisting of:

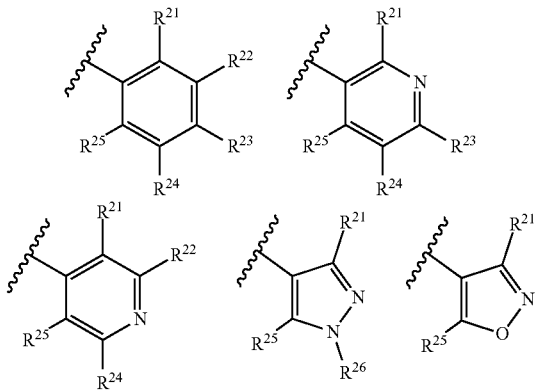

-continued

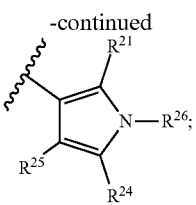

R²¹ is H, halogen, (1-3C)alkyl, (1-2C)alkoxy, hydroxy(1-2C)alkyl, (3-4C)cycloalkyl, (2-3C)alkenyl or cyano;
R²² is H, halogen, (1-2C)alkyl or (1-2C)alkoxy;
R²³ is H, halogen, (1-2C)alkyl, (1-2C)alkoxy, cyano or hydroxy;
R²⁴ is H, halogen, (1-2C)alkyl or (1-2C)alkoxy;
R²⁵ is H, halogen, (1-3C)alkyl, (1-2C)alkoxy, hydroxy(1-2C)alkyl, (3-4C)cycloalkyl, (2-3C)alkenyl or cyano;
R²⁶ is H, (1-6C)alkyl, (3-6C)cycloalkyl, (2-5C)heterocycloalkyl, (1-2C)alkoxy[(2-4C)alkoxy]$_n$(1-6C)alkyl, wherein n represents an integer of 1,2,3 or 4, all alkyl, heterocycloalkyl and (1-2C)alkoxy[(2-4C)alkoxy]$_n$(1-6C)alkyl groups optionally substituted with one or more groups selected from (1-2C)alkyl, (1-2C)alkoxy, hydroxyl, oxo, amino, (3-6C)cycloalkyl, di[(1-2C)alkyl]amino or (2-5C)heterocycloalkyl; and wherein in the above Formula I only one of R²¹ and R²⁵ in R² can be H.

13. The method according to claim 1, wherein said mutation results in a substitution of one or more serine or threonine residues in the corresponding CTNNB1-encoded protein, or wherein said mutation is a deletion of one or more serine or threonine residues in the corresponding CTNNB1-encoded protein.

14. The method according to claim 1, wherein in Formula I:
R¹ is

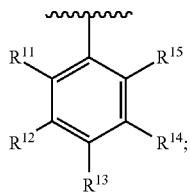

R¹¹ is H, halogen, (1-2C)alkyl, (2-3C)alkenyl, (2-3C)alkynyl, (1-2C)alkoxy or OC₂H₃, all alkyl and alkoxy groups optionally being substituted with one or more halogen;
R¹² is H, halogen, (1-2C)alkyl or (1-2C)alkoxy;
R¹³ is R¹³²O, R¹³⁵C(O), (2-7C)heterocycloalkyl, or (1-5C)heteroaryl each heterocycloalkyl or heteroaryl optionally being substituted with (1-2C)alkyl, fluoro, hydroxyl, oxo, (1-2C)alkoxy, (1-6C)alkylcarbonyl, (1-6C)alkylsulfonyl, (1-5C)alkoxycarbonyl, (1-6C)alkylaminocarbonyl, (3-6C)cycloalkylcarbonyl, (2-7C)heterocycloalkylcarbonyl or di[(1-2C)alkyl]amino, each alkylcarbonyl, alkylsulfonyl, alkoxycarbonyl, alkylaminocarbonyl, cycloalkylcarbonyl or heterocycloalkylcarbonyl optionally being substituted with (1-2C)alkyl, fluoro, hydroxyl, cyano, oxo or (1-2C)alkoxy;
R¹³² is (1-6C)alkyl, (3-6C)cycloalkyl, (2-7C)heterocycloalkyl, (6-10C)aryl or (1-5C)heteroraryl each optionally substituted with one or more groups selected from (1-2C)alkyl, halogen, hydroxyl, (1-2C)alkoxy, di[(1-2C)alkyl]amino or (2-7C)heterocycloalkyl;
R¹³⁵ is (2-7C)heterocycloalkyl, (1-6C)alkylamino, di[(1-6C)alkyl]amino, (2-7C)heterocycloalkylamino or (3-6C)cycloalkylamino each optionally substituted with one or more groups selected from (1-2C)alkyl, fluoro, hydroxyl, (1-2C)alkoxy, di[(1-2C)alkyl]amino, (2-7C)heterocycloalkyl, oxo, cyano or amino;
R¹⁴ is H, halogen, (1-2C)alkyl or (1-2C)alkoxy; and
R¹⁵ is H, halogen;
R² is selected from the group consisting of:

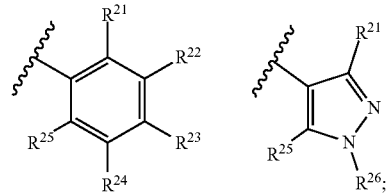

R²¹ is H, halogen, (1-3C)alkyl, (1-2C)alkoxy, hydroxy(1-2C)alkyl, (3-4C)cycloalkyl, (2-3C)alkenyl or cyano;
R²² is H, halogen, (1-2C)alkyl or (1-2C)alkoxy;
R²³ is H, halogen, (1-2C)alkyl, (1-2C)alkoxy, cyano or hydroxy;
R²⁴ is H, halogen, (1-2C)alkyl or (1-2C)alkoxy;
R²⁵ is H, halogen, (1-3C)alkyl, (1-2C)alkoxy, hydroxy(1-2C)alkyl, (3-4C)cycloalkyl, (2-3C)alkenyl or cyano;
R²⁶ is H, (1-6C)alkyl, (3-6C)cycloalkyl, (2-5C)heterocycloalkyl, (1-2C)alkoxy[(2-4C)alkoxy]$_n$(1-6C)alkyl, wherein n represents an integer of 1,2,3 or 4, all alkyl, heterocycloalkyl and (1-2C)alkoxy[(2-4C)alkoxy]$_n$(1-6C)alkyl groups optionally substituted with one or more groups selected from (1-2C)alkyl, (1-2C)alkoxy, hydroxyl, oxo, amino, (3-6C)cycloalkyl, di[(1-2C)alkyl]amino or (2-5C)heterocycloalkyl; and wherein in the above Formula I only one of R²¹ and R²⁵ in R² can be H.

15. The method according to claim 1, wherein in Formula I:
R¹ is

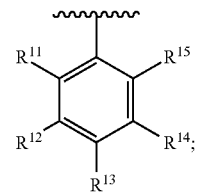

R¹¹ is (1-2C)alkoxy, the alkoxy optionally being substituted with one or more halogen;
R¹² is H;
R¹³ is R¹³²O, R¹³⁵C(O), (2-7C)heterocycloalkyl, or (1-5C)heteroaryl each heterocycloalkyl or heteroaryl optionally being substituted with (1-2C)alkyl, (1-6C)alkylcarbonyl, or (2-7C)heterocycloalkylcarbonyl, each alkylcarbonyl or heterocycloalkylcarbonyl optionally being substituted with (1-2C)alkyl or (1-2C)alkoxy;
R¹³² is (2-7C)heterocycloalkyl, optionally substituted with one or more groups selected from (1-2C)alkyl;

R¹³⁵ is (2-7C)heterocycloalkyl or (2-7C)heterocycloalkylamino, each optionally substituted with one or more groups selected from (1-2C)alkyl;
R¹⁴ is H; and
R¹⁵ is H;
R² is selected from the group consisting of:

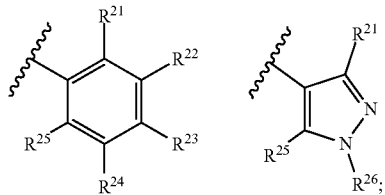

R²¹ is (1-3C)alkyl;
R²² is H;
R²³ is H;
R²⁴ is H;
R²⁵ is (1-3C)alkyl;
R²⁶ is H, (1-6C)alkyl, or (1-2C)alkoxy[(2-4C)alkoxy]ₙ(1-6C)alkyl, wherein n represents an integer of 1, 2, 3 or 4.

16. The method according to claim 13, wherein said mutation results in a substitution of one or more serine or threonine residues in the corresponding CTNNB1-encoded protein at a position selected from S33, S37, S45 and T41, or wherein said mutation is a deletion of one or more serine or threonine residues in the corresponding CTNNB1-encoded protein at a position selected from S33, S37, S45 and T41.

17. The method according to claim 15, wherein said mutation results in a substitution of one or more serine or threonine residues in the corresponding CTNNB1-encoded protein, or wherein said mutation is a deletion of one or more serine or threonine residues in the corresponding CTNNB1-encoded protein.

18. The method according to claim 17, wherein said mutation results in a substitution of one or more serine or threonine residues in the corresponding CTNNB1-encoded protein at a position selected from S33, S37, S45 and T41, or wherein said mutation is a deletion of one or more serine or threonine residues in the corresponding CTNNB1-encoded protein at a position selected from S33, S37, S45 and T41.

19. The method according to claim 15, wherein the mutation is a missense mutation or a deletion of the serine residue corresponding to codon 33 of CTNNB1.

20. The method according to claim 15, wherein the mutation is a missense mutation or a deletion of the threonine residue corresponding to codon 41 of CTNNB1.

21. The method according to claim 15, wherein the mutation is a missense mutation or a deletion of the serine residue corresponding to codon 45 of CTNNB1.

* * * * *

UNITED STATES PATENT AND TRADEMARK OFFICE
CERTIFICATE OF CORRECTION

PATENT NO. : 11,208,696 B2
APPLICATION NO. : 15/566583
DATED : December 28, 2021
INVENTOR(S) : De Roos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this
Eighteenth Day of April, 2023

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 781
<212> TYPE: PRT
<213> ORGANISM: Homo sapiens

<400> SEQUENCE: 1

```
Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
```

```
                85                  90                  95
Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
            115                 120                 125

Ser Gln Met Leu Lys His Ala Val Val Asn Leu Ile Asn Tyr Gln Asp
            130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
            210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
            290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
            325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
            370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
            405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
            450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
            485                 490                 495

Leu Leu His Pro Pro Ser His Trp Pro Leu Ile Lys Ala Thr Val Gly
            500                 505                 510
```

```
Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
        530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
                615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
            645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
        690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
770                 775                 780
```